(12) United States Patent
Romley

(10) Patent No.: US 10,531,865 B2
(45) Date of Patent: Jan. 14, 2020

(54) METHODS AND DEVICES FOR MANIPULATING AND FASTENING TISSUE

(71) Applicant: EndoGastric Solutions, Inc., Redmond, WA (US)

(72) Inventor: Richard Romley

(73) Assignee: EndoGastric Solutions, Inc., Redmond, WA (US)

( * ) Notice: Subject to any disclaimer, the term of this patent is extended or adjusted under 35 U.S.C. 154(b) by 247 days.

(21) Appl. No.: 15/430,113

(22) Filed: Feb. 10, 2017

(65) Prior Publication Data

US 2017/0150952 A1   Jun. 1, 2017

Related U.S. Application Data

(60) Division of application No. 13/791,886, filed on Mar. 8, 2013, now Pat. No. 9,572,571, which is a continuation-in-part of application No. 13/229,452, filed on Sep. 9, 2011, now Pat. No. 10,010,319.

(51) Int. Cl.
| | |
|---|---|
| *A61B 17/00* | (2006.01) |
| *A61B 17/068* | (2006.01) |
| *A61B 1/00* | (2006.01) |
| *A61B 17/064* | (2006.01) |
| *A61F 5/00* | (2006.01) |
| *A61B 17/04* | (2006.01) |
| *A61B 17/072* | (2006.01) |
| *A61B 17/30* | (2006.01) |

(52) U.S. Cl.
CPC .... *A61B 17/00234* (2013.01); *A61B 1/00094* (2013.01); *A61B 17/0401* (2013.01); *A61B 17/064* (2013.01); *A61B 17/068* (2013.01); *A61F 5/0086* (2013.01); *A61B 17/072* (2013.01); *A61B 17/07292* (2013.01); *A61B 2017/00243* (2013.01); *A61B 2017/00349* (2013.01); *A61B 2017/00353* (2013.01); *A61B 2017/00557* (2013.01); *A61B 2017/00818* (2013.01); *A61B 2017/00827* (2013.01); *A61B 2017/00862* (2013.01); *A61B 2017/0409* (2013.01); *A61B 2017/0649* (2013.01); *A61B 2017/306* (2013.01)

(58) Field of Classification Search
CPC ......... A61F 5/0003–0089; A61B 17/04–0401; A61B 17/0469–0485; A61B 17/072–07292; A61B 2017/0403–0464; A61B 2017/047–048; A61B 2017/07214–07285; A61B 2018/00494
See application file for complete search history.

(56) References Cited

U.S. PATENT DOCUMENTS

| | | | |
|---|---|---|---|
| 2002/0082621 A1* | 6/2002 | Schurr | A61B 17/0643 606/151 |
| 2007/0005082 A1* | 1/2007 | Kraemer | A61B 17/0401 606/153 |
| 2007/0129738 A1* | 6/2007 | Kraemer | A61B 17/0401 606/153 |

\* cited by examiner

*Primary Examiner* — Jonathan A Hollm
(74) *Attorney, Agent, or Firm* — Fulwilder Patton LLP

(57) ABSTRACT

Stomach tissue is manipulated and fastened with a tissue grasper and a tissue shaper to form folds in the stomach. The tissue grasper and the tissue shaper rotate and translate relative to one another. The tissue grasper has a plurality of vacuum orifices to adhere the tissue grasper to tissue.

12 Claims, 58 Drawing Sheets

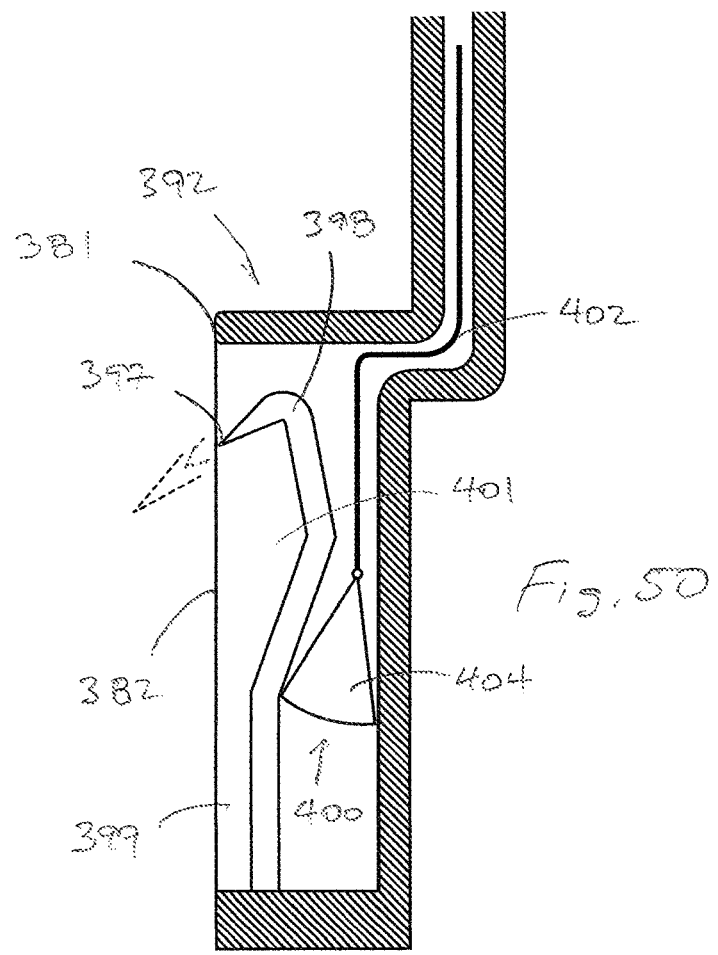

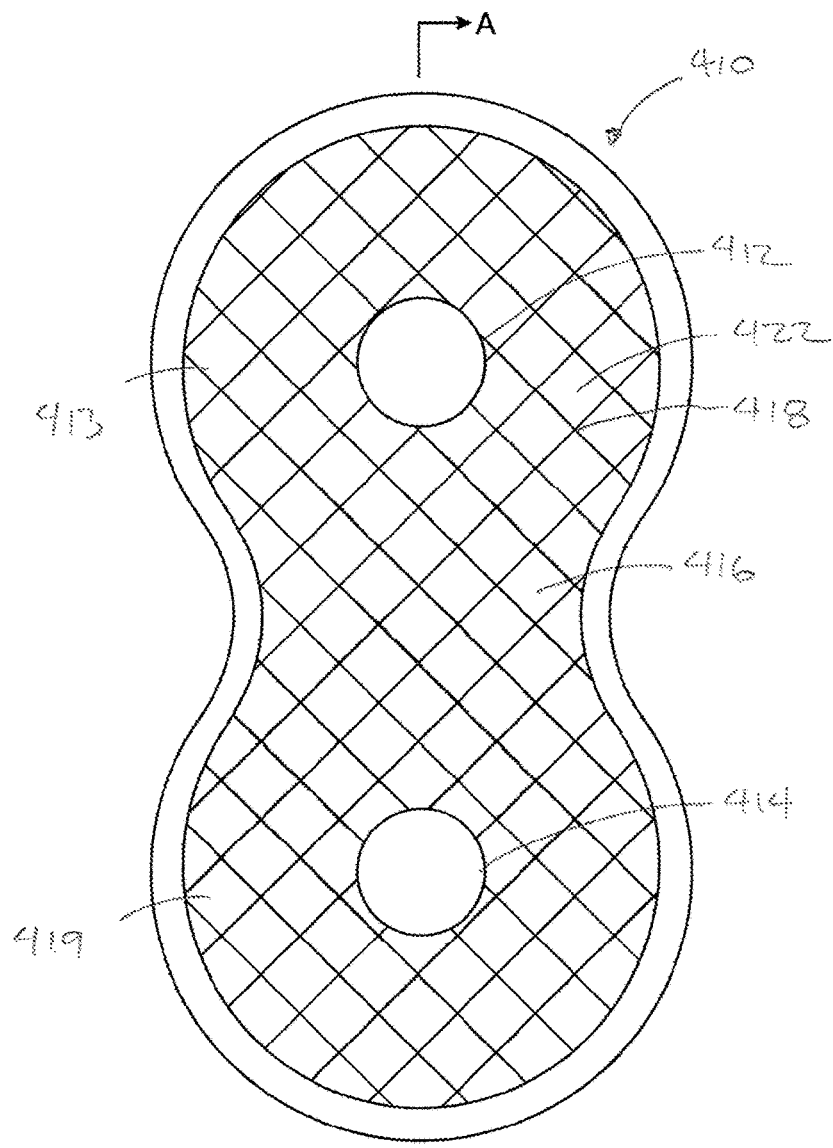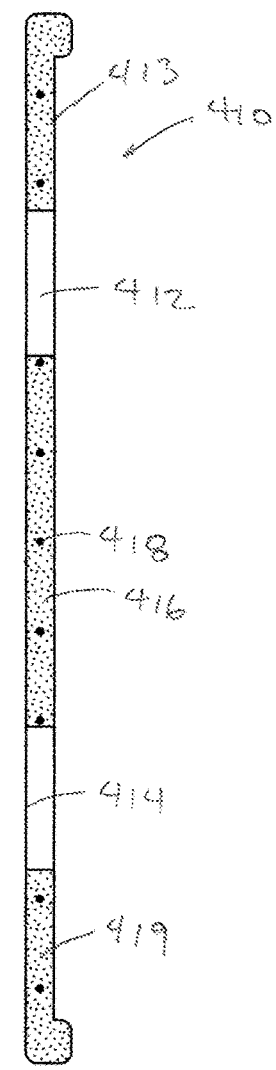
Fig. 51　　A-A Fig. 52

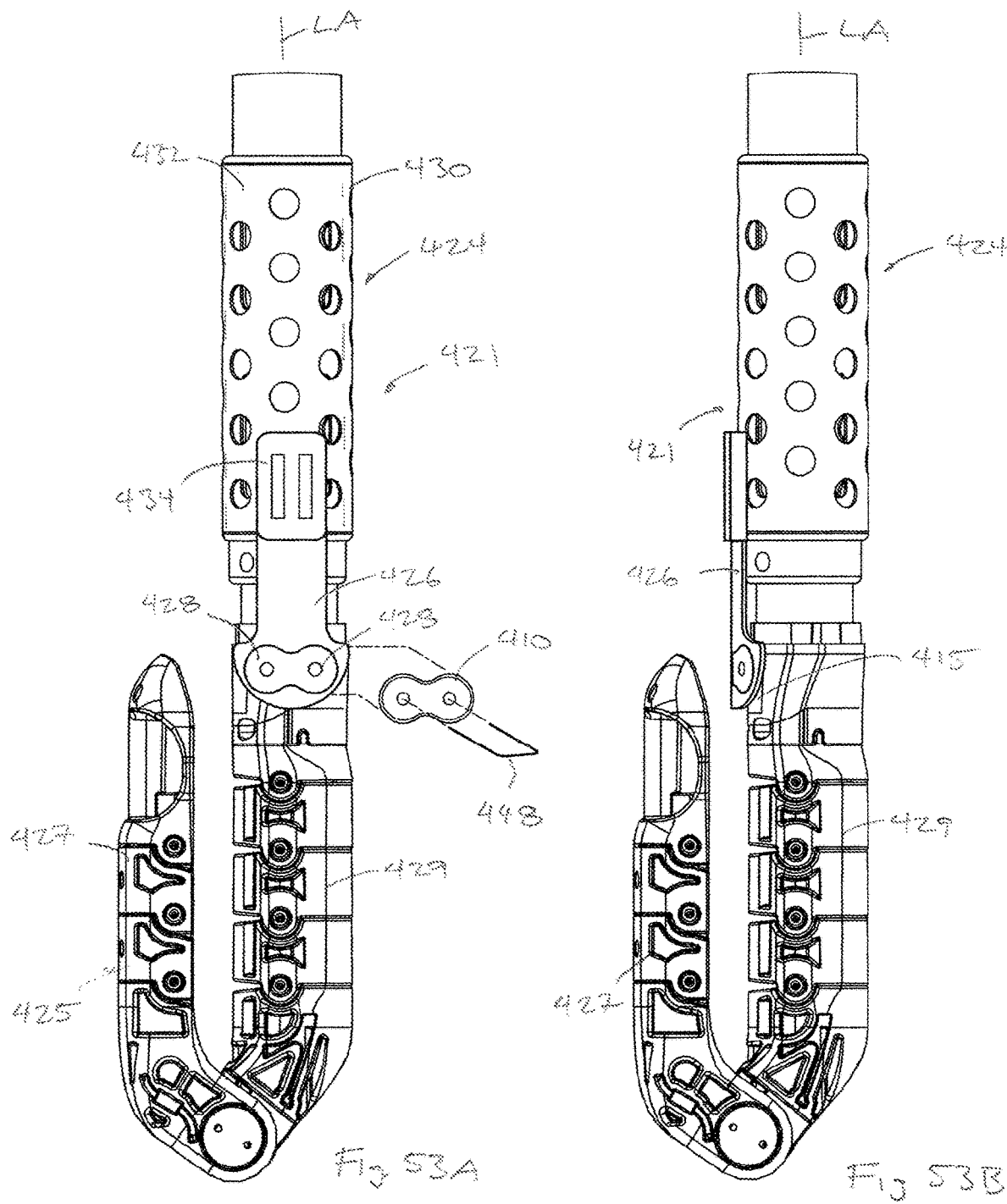

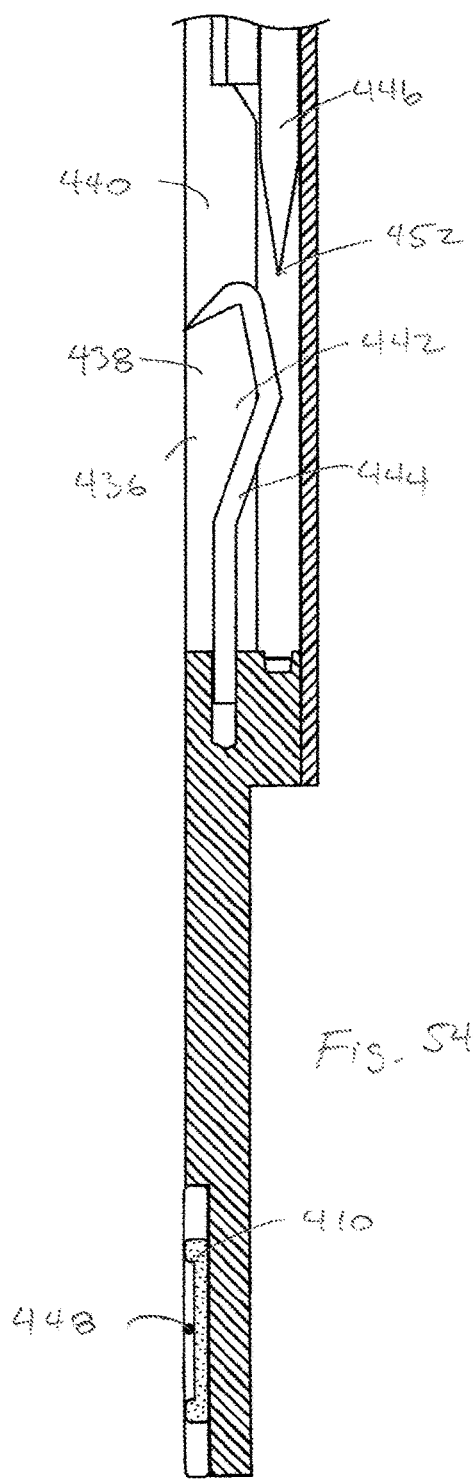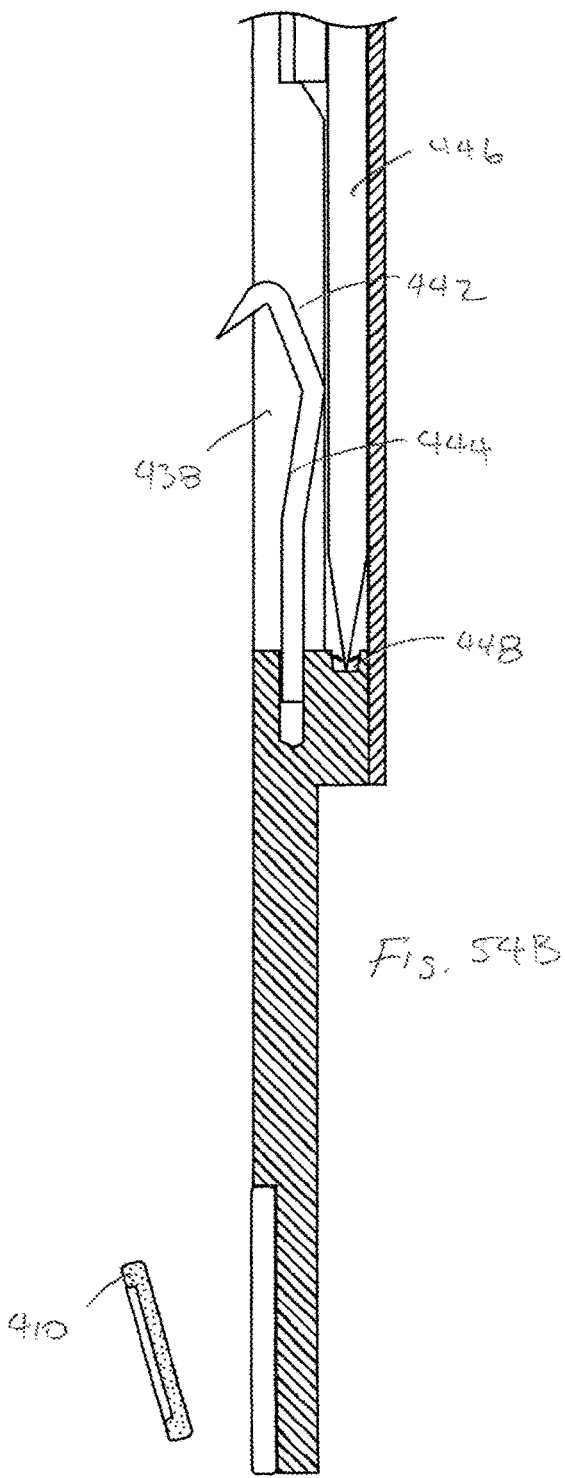

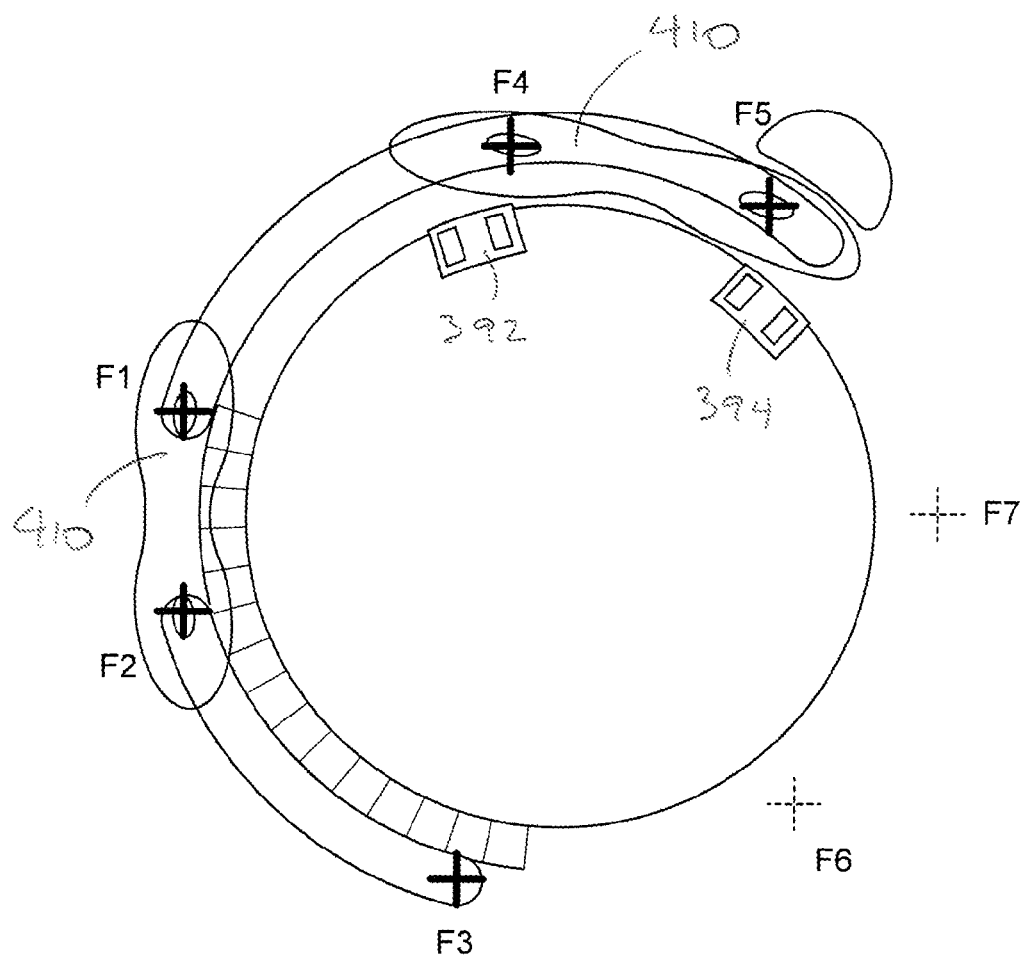

METHODS AND DEVICES FOR MANIPULATING AND FASTENING TISSUE

CROSS REFERENCE TO RELATED APPLICATIONS

The present application is a division of Ser. No. 13/791,886, filed Mar. 8, 2013, which will issue as U.S. Pat. No. 9,572,571 on Feb. 21, 2017, which is a continuation-in-part of U.S. application Ser. No. 13/229,452, filed Sep. 9, 2011 by Richard Romley. This application is also related to U.S. application Ser. No. 13/791,900, filed Mar. 8, 2013 and U.S. application Ser. No. 13/791,892, filed Mar. 8, 2013 both by Richard Romley et al., which are all hereby incorporated by reference.

BACKGROUND OF THE INVENTION

The present invention relates to methods and devices for manipulating and fastening tissue. In particular, the present invention may be useful in treating gastroesophageal reflux disease (GERD).

Referring to FIG. 2, a normal stomach and esophagus are shown with a disease state shown in the dotted line position. GERD develops in the disease state since the gastroesophageal flap valve at the junction or intersection between the esophagus and stomach has deteriorated so that stomach contents can splash into the esophageal tract resulting in GERD. The disease state is associated with a shorter esophageal tract and a somewhat enlarged stomach. The junction has also moved orally thereby effectively shortening the esophageal tract as well.

SUMMARY OF THE INVENTION

The present invention provides devices and methods for manipulating and fastening tissue together. The device includes numerous aspects, which may be practiced by themselves or in combination with other aspects of the invention. The device will be described in connection with treating GERD but shall have applications in other fields as well.

The device includes a shaft and a tissue displacing element coupled to the shaft. The tissue displacing element is configured to reshape stomach tissue. The stomach tissue is then fastened together to form a fold. When treating GERD the fold is formed at the intersection of the esophageal tract and stomach.

In one aspect of the invention, a plurality of tissue displacing elements are coupled to the shaft. The displacing elements are preferably individually and independently movable. The device may also include a common retractor, which is configured to displace the tissue displacing elements simultaneously. When used to recreate the junction between the esophagus and stomach, the common retractor may be moved distally along the shaft to lengthen the fold of tissue. The device may include a lock, which couples two tissue displacing elements together while maintaining the ability to independently move, or maintain stationary, the third element. In this manner, two of the tissue displacing elements may be simultaneously moved while at least one tissue displacing element remains stationary.

The tissue displacing element may include an elongate element, such as a wire, having an engaging element, such as a helical coil, at the distal end. Once the coil is rotated into tissue, the tissue is displaced by applying tension to the wire. The wire may have a curved distal portion so that rotation of the wire changes a position and angular orientation of the wire. A sheath may be slidable over the wire to cover and uncover the distal portion of the wire. The shape of the distal portion changes when the sheath covers and uncovers the wire thereby providing greater flexibility in directing the coil to engage a particular stomach location.

In another aspect of the invention, the device may include a tissue shaper coupled to the shaft. Tissue may be moved into the tissue shaper by simply moving the tissue displacing element to draw tissue into the tissue shaper. Alternatively, tissue may be moved into the tissue shaper by moving only the tissue shaper or the tissue shaper and the tissue displacing element simultaneously. The shaper has a cavity with an open proximal end leading to the cavity. Alternatively, the open end may be at the distal end leading to the cavity. The tissue displacing element may be movable within the cavity and to positions proximal and distal to the cavity. The tissue shaper may also be removable from the shaft and replaceable with another shaper. The shaft may include a primary shaft and a secondary shaft, which are slidable relative to one another, the tissue shaper being coupled to the primary shaft and the tissue displacing element being coupled to the secondary shaft.

The tissue shaper may also be partially or completely resilient so that the cavity may be expanded and to provide compression on tissue as tissue enters the cavity. The elastomeric portion may be positioned at the proximal open end of the cavity so that the proximal end may expand to accommodate tissue. The cavity may also include an elastomeric portion adjacent a midportion of the cavity. The flexibility of the tissue shaper may also be enhanced by providing a plurality of longitudinal slits in the tissue shaper. The device may also include a tension sensor coupled to the tissue displacing element. The tension sensor measures tension on the tissue displacing element developed during displacement of tissue.

The shaft may include a vacuum orifice configured to adhere the shaft to tissue. The vacuum orifice may be used to grasp the esophageal tract. The vacuum orifice may be used to stabilize tissue displaced by the tissue displacing element so that the tissue displacing element may be released and repositioned to displace another part of the stomach while the vacuum orifice holds previously displaced stomach tissue.

The device may also include a tissue shifting element configured to shift tissue held by the shaper. The tissue shifting element may be configured to engage a stomach side of the fold and displace the stomach side of the fold distally thereby moving the intersection of the fold distally. Alternatively, the tissue shifting element may displace both tissue layers such as the esophageal side and the stomach side when treating GERD. Another tissue shifting element may be provided for shifting the esophageal side (radially inner side) further into the tissue shaper either independently or simultaneously with the stomach side (radially outer side). The tissue shifting element displaces tissue to increase a length of the fold of tissue while the fold of tissue is positioned in the cavity. The tissue shifting element may also draw tissue into the shaper while shifting tissue already held by the shaper.

The device may include a fastener applier which is a separate device delivered down a fastener lumen in the shaft. The fastener applier may include a fastener cartridge containing a plurality of fasteners and may deliver a plurality of fasteners in a single actuation. The fastener cartridge may apply a compressive force to the fold of tissue prior to application of the fastener.

The common retractor may include a slot in which the tissue displacing element is positioned so that the central axis of the wire translates within the slot. Movement within the slot changes an angular position by at least 45 degrees with respect to the longitudinal axis of the shaft when moving within the slot. The change in angular position provided by the slot may be accomplished without moving the shaft.

The tissue shaper may also draw tissue through an open distal end for forming a fold at an intersection of the stomach and the esophagus adjacent the lesser curvature. The tissue shaper is positioned in the esophagus and the fold is released so that the stomach tissue positioned in the tissue shaper falls back into the stomach. The tissue shaper may have a convex side facing inward relative to the esophagus to create a convex side of the fold. The fastener is applied to the fold before release above the junction between the esophageal tract and the stomach along the greater curvature side and preferably at least 3 cm above.

In another aspect of the present invention, a tissue grasper is provided which has an elongate body that defines a longitudinal axis and has an outer surface. A plurality of vacuum orifices are positioned on the outer surface of the elongate body to form a sealing surface to adhere the outer surface of the elongate body to tissue using suction. The plurality of vacuum orifices may be separated into a first section and a second section with both sections both extending partially around the outer surface of the elongate body when viewed along the longitudinal axis. The first and second sections together form a circumferential sealing surface. For example, the first section may extend around 270 degrees while the second section extends around 90 degrees around the body.

The tissue grasper may also include a third section rotatable about the longitudinal axis relative to the first and second sections. The third section may extend less than 100 degrees around the outer surface when viewed along the longitudinal axis. A fourth section may also be provided similar to the third section and also rotatable (and may longitudinally translate as well) relative to the first, second and third sections. The third and fourth sections are also movable to the same longitudinal position and may be positioned to create a window in a gap between the third and fourth sections. The window may be placed at a fastener application site.

The tissue grasper may also have a tissue piercing element to help securely hold tissue. The tissue piercing element is contained in a recess extending below the outer surface of at least one of the plurality of vacuum orifices. The tissue piercing element is movable between a stored position and a working position. The piercing element has a sharp tip to pierce tissue when tissue is drawn into the recess through the at least one vacuum orifice using suction. The tissue piercing element moves out from the recess to engage tissue when moving from the stored position to the working position. In one aspect, the sharp tip extends no more than 4 mm from the outer surface of the elongate body when in the working position. The recess may be a slot having sidewalls that guide the tissue piercing element.

In still another aspect of the present invention, a reinforcing element is provided to reinforce the folds and, in particular, the posterior and anterior ends of the fold. The reinforcing element has a first side and a second side with one side attached to the anterior side and the other attached to the posterior side of the stomach on the lesser curvature side of the stomach. The reinforcing element may be mounted to the tissue grasper, or a separate delivery device, to expose the first and second sides for application of a fastener. The reinforcing element remains attached to the elongate body after the first (and/or second) side is attached to tissue for controlling the tissue attached to the reinforcing element using the tissue grasper. The reinforcing element may include a woven element having an interstitial space configured to receive a fastener. The reinforcing element may also include a reinforced polymer sheet. The reinforcing element may also include eyelets which receive the fasteners.

A first tissue shaper may be provided and coupled to the tissue grasper. The first tissue shaper has a first shaft rotatably coupled to the elongate body. The first tissue shaper is also longitudinally translatable relative to the elongate body. The first tissue shaper has a first tissue displacing element to draw tissue into a first cavity in the first tissue shaper. The first cavity may be formed by a mold that is pivotally coupled to the first shaft with the cavity being formed therebetween. A second tissue shaper may also be provided which has a second shaft extending through the elongate body. The second tissue shaper is also rotatable about the longitudinal axis relative to the first tissue shaper and the tissue grasper. The second tissue shaper forms a second cavity with a second mold that is pivotally coupled to the second shaft. A second cavity formed by the second tissue shaper is formed between the second mold and the first shaft.

These and other features and aspects of the invention will become apparent from the following description of the preferred embodiment, drawings and claims.

BRIEF DESCRIPTION OF DRAWINGS

FIG. 50 is a cross-sectional view of the tissue piercing element of the third and fourth sections of the tissue grasper.

FIG. 51 shows a reinforcing element.

FIG. 52 is a cross-sectional view of the reinforcing element.

FIG. 53A shows the reinforcing element mounted to the tissue grasper.

FIG. 53B is another view of the reinforcing element mounted to the tissue grasper.

FIG. 54A is a cross-sectional view of the tissue piercing element and the reinforcing element mounted to a collar.

FIG. 54B shows the reinforcing element released.

FIG. 61 illustrates another method of using the reinforcing element.

DESCRIPTION OF THE PREFERRED EMBODIMENTS

Figure 1:
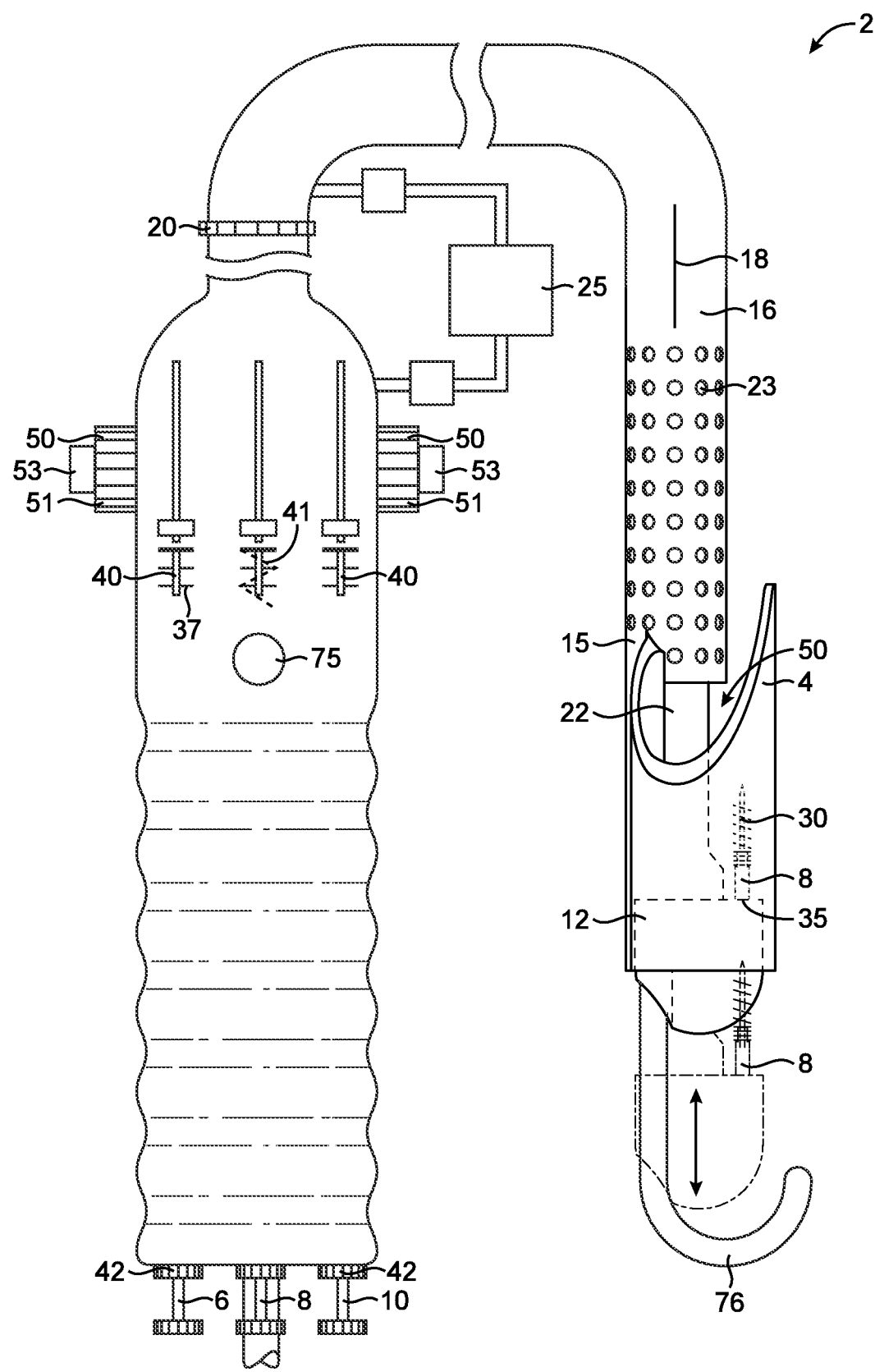
FIG. 1 shows a device for manipulating and fastening tissue of the present invention.
Figure 2:
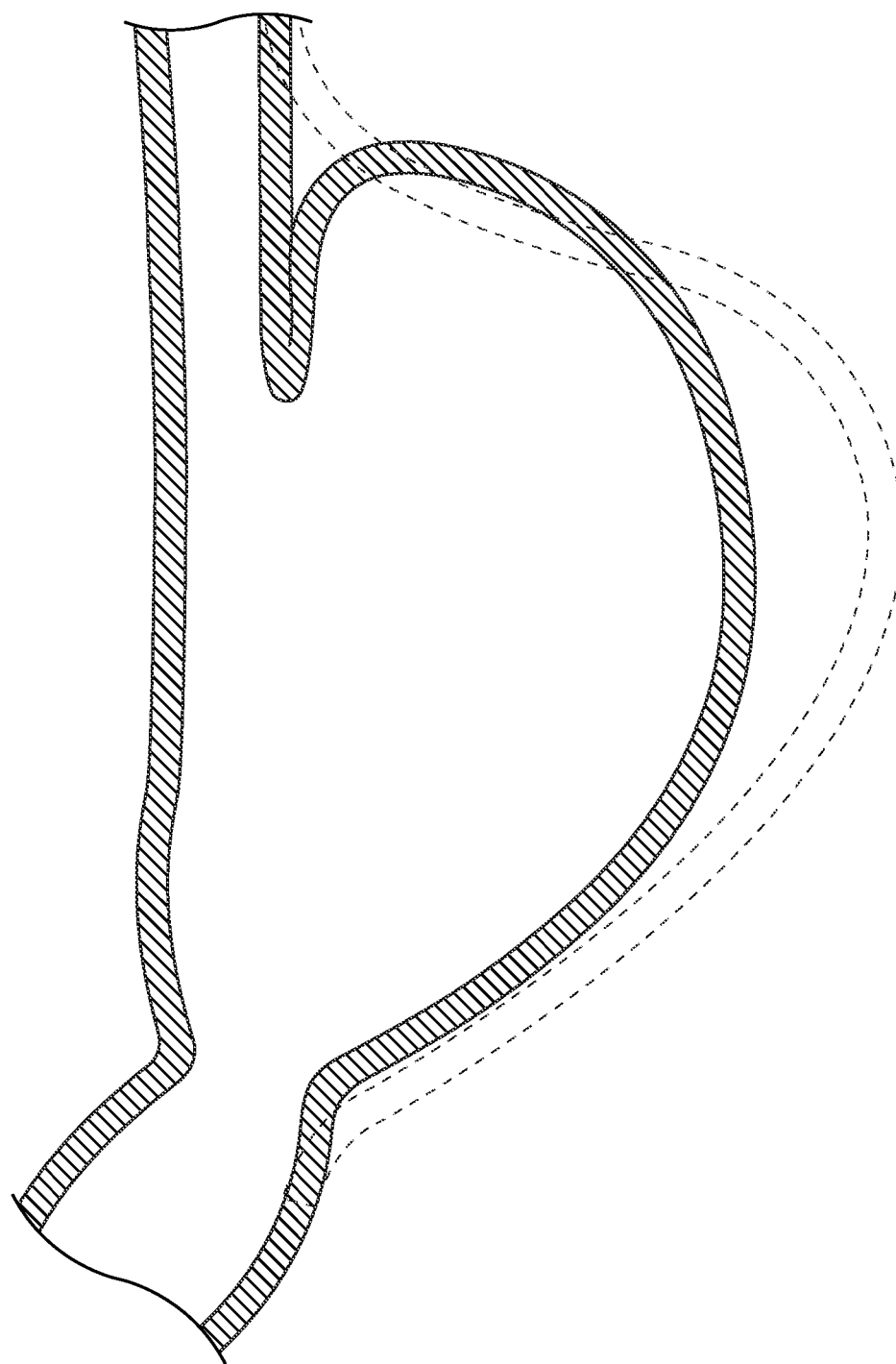
FIG. 2 shows a stomach and an outline of the stomach in a disease state.
Figure 4:
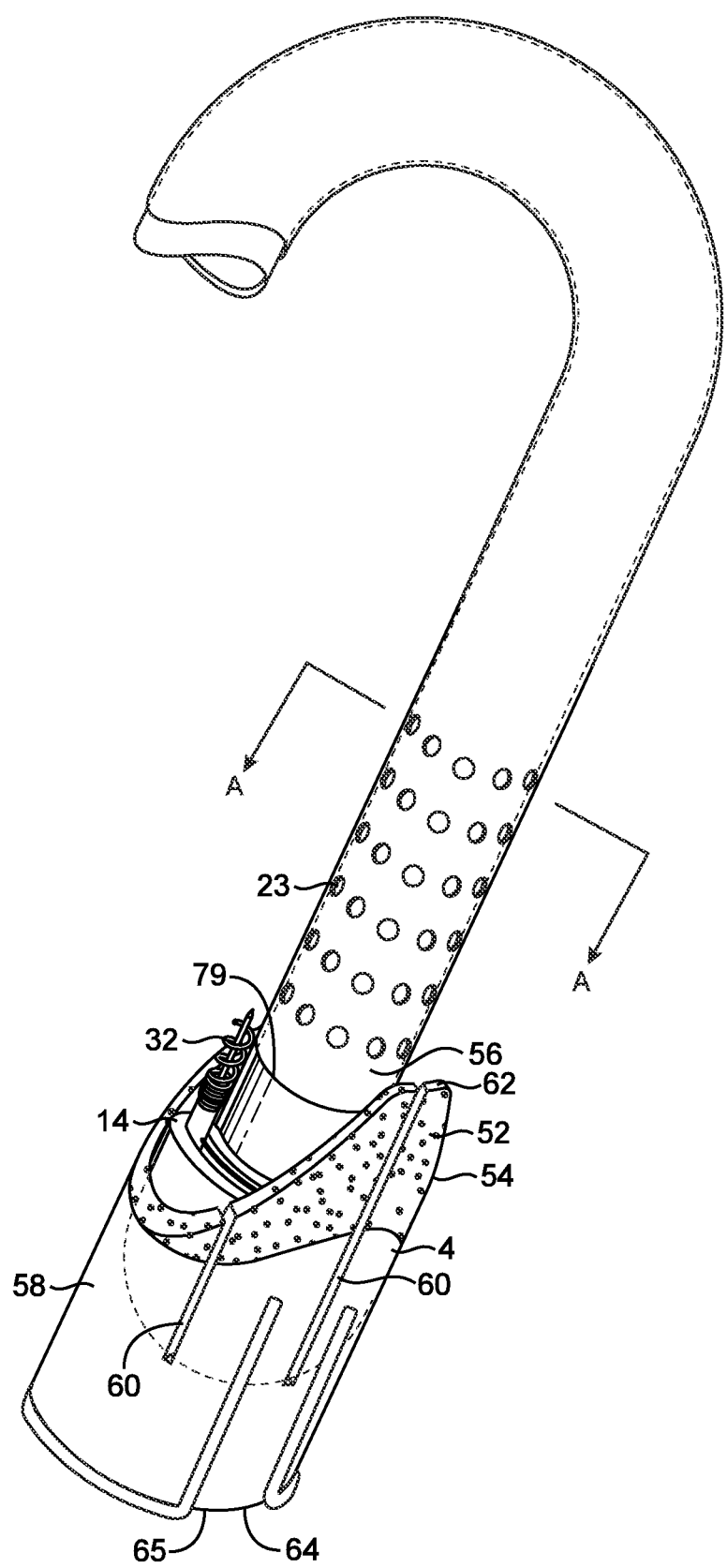
FIG. 4 shows a perspective view of the device.
Figure 5:
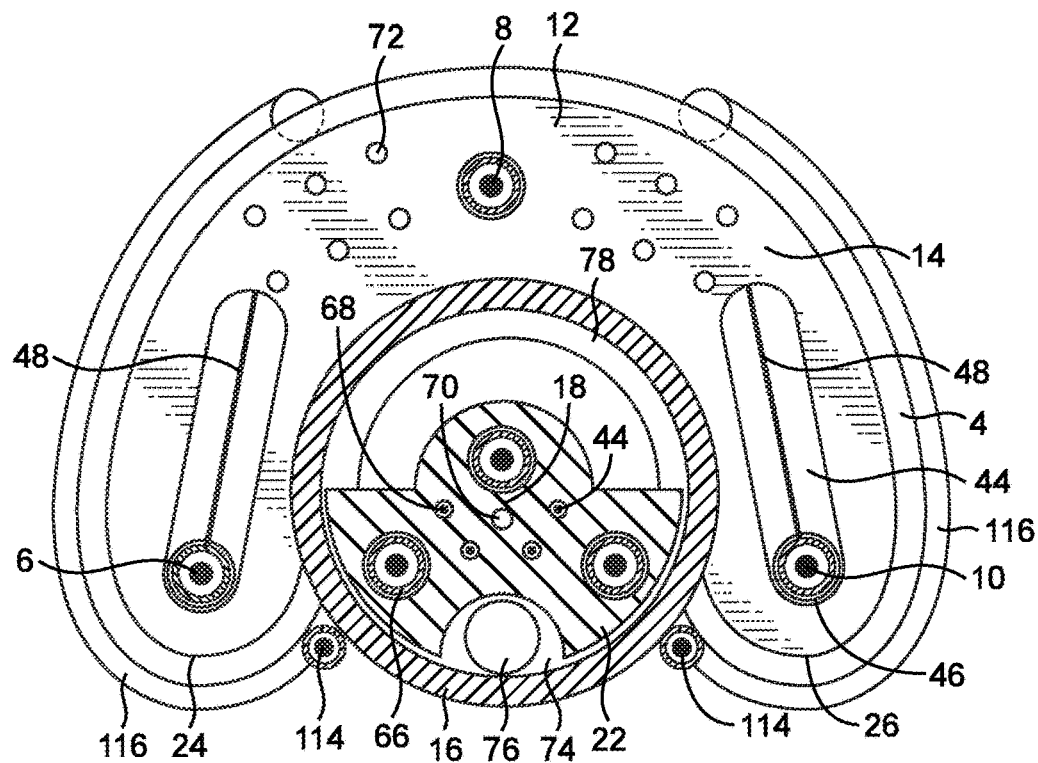
FIG. 5 is a cross-sectional view of the device at line A-A of FIG. 4.

Referring to FIGS. 1, 4 and 5, a device 2 for manipulating and fastening tissue is shown. The device 2 and various aspects thereof may be used to manipulate and fasten tissue anywhere in the body. In particular, the device 2 of the present invention may be used to manipulate stomach tissue to recreate the intersection between the stomach and the esophageal tract.

The device 2 includes a tissue shaper 4 which shapes tissue into a desired shape such as a gastroesophageal flap valve. The device 2 has first, second and third tissue displacing elements 6, 8, 10 which gather and manipulate tissue into a cavity 50 in the tissue shaper 4. The tissue displacing elements 6, 8, 10 are coupled to a common retractor 12 having a platform 14 which may be used to simultaneously move the tissue displacing elements 6, 8, 10 as described below. The tissue shaper 4 is coupled to a shaft 15 consisting of a flexible primary shaft 16 and a flexible secondary shaft 22 and may be releasably coupled to the shaft 15 as described below. The shaft 15 defines a longitudinal axis 18 and angular orientations and displacements are often defined and described herein as being relative to the longitudinal axis 18. For example, referring to FIG. 6, an angle B is defined between the first and second tissue displacing elements 6, 8 as defined relative to the longitudinal axis 18. The longitudinal axis 18 may be substantially straight or may be curved without departing from the scope of the invention so long as the longitudinal axis 18 generally follows and defines the orientation of the shaft 15. The primary shaft 16 terminates at the proximal end at a lock 20 which locks and seals the primary shaft 16 to the secondary shaft 22. When the lock 20 is unlocked, the primary and secondary shafts 16, 22 may be moved relative to one another. The primary and secondary shafts 16, 22 are movable relative to one another so that the common retractor 12 and platform 14 are movable as shown by the solid and dotted line positions of FIG. 1 although the common retractor 12 has greater range of motion than depicted in both directions. A plurality of vacuum orifices 23 are positioned on the primary shaft 16 to grasp tissue, such as the esophageal tract, as also described below. The vacuum orifices 23 are coupled to a suction source 25 through a space between the first and second shafts 16, 22.

Figure 6:
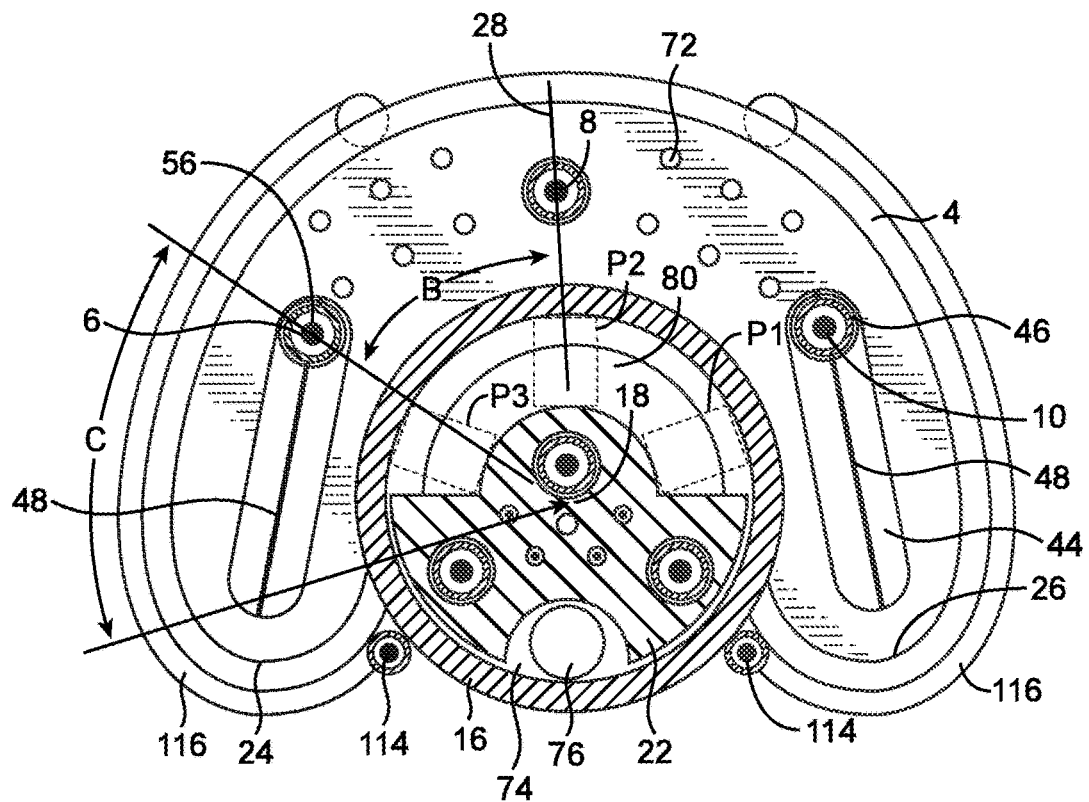
FIG. 6 is a cross-sectional view of the device of FIG. 5 with guide tubes moved within slots to translate the tissue displacing elements.

The tissue shaper 4 forms a fold of tissue which is substantially similar to a natural gastroesophageal flap valve. To this end, the tissue shaper 4 forms a generally tubular structure open on both ends, the esophagus on one side and the stomach on the other. The generally tubular structure may also have an open side proximate the esophagus or may be a substantially closed shape. Referring to FIGS. 5 and 6, the tissue shaper 4 has a generally curved cross-sectional shape terminating at a first end 24 and a second end 26. The curved cross-sectional shape forms an arc of at least 180 degrees relative to the longitudinal axis between the first and second ends 24, 26. The tissue shaper 4 also defines a central plane 28 (FIG. 6) which lies equidistant from the first and second ends 24, 26 and/or may define an axis of symmetry when viewed along the longitudinal axis 18. The second tissue displacing element 8 lies on the central plane 28 but may be offset from the plane 28 as well.

The tissue shaper 4 may, of course, take other suitable cross-sectional shapes such as oval, round, or V-shaped without departing from the scope of the invention and it is understood that these shapes also would have a central plane as defined herein. Furthermore, the tissue shaper 4 may also be omitted without departing from various aspects of the present invention. For example, the tissue displacing elements 6, 8, 10 alone may be used to displace stomach tissue and form a fold of tissue by simply displacing the tissue in a manner which forms the fold of tissue without requiring the tissue shaper 4. The tissue may be displaced into the shaper 4 without moving the shaper 4 and using only elements 6, 8 10, moving only the tissue shaper 4, or moving both the elements 6, 8, 10 and shaper together.

Figure 7:
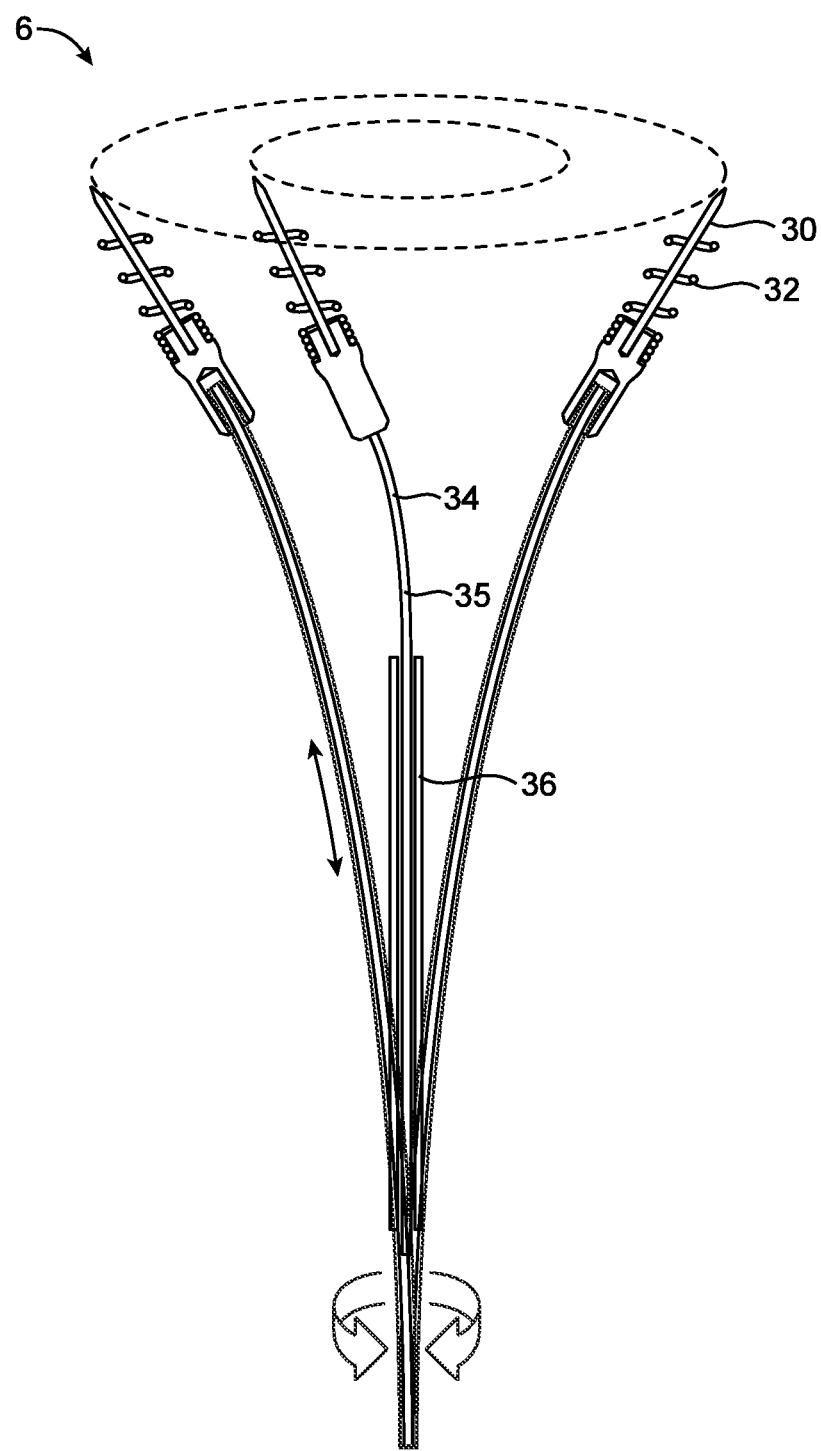
FIG. 7 shows the range of motion provided by the tissue displacing element and the range of motion provided when the sheath is used.

Referring to FIG. 7, the tissue displacing elements 6, 8, 10 each include a tissue engaging element 30, such as a helical coil 32, which is rotated to pierce and engage tissue as is known in the art. The coil 32 is coupled to an elongate element 34, such as a wire 35, and the elongate element 34 is covered by a retractable sheath 36. The elongate element 34 may have a curved shape which permits the user to direct the distal end in a desired direction by simply rotating element 30. The sheath 36 may be advanced over the wire 35 to change the shape of the distal portion to provide a broader range of motion to direct the coil 32 as desired. FIG. 7 shows the elongate element 34 bent further by the sheath 36, however, the sheath 36 could also straighten the elongate element 34. Furthermore, the elongate element 34 or sheath 36 may be substantially straight, rather than bent, without departing from the scope of the invention.

As will be described further below, the tissue engaging elements 6, 8, 10 may be used to displace tissue substantially longitudinally when the wire 35 is retracted. The elements 6, 8, 10 may be retracted into and extended from the shaft as shown throughout the Figures. The curved shape of the wire 35 may also provide an angular displacement (change in orientation) with respect to the longitudinal axis 18 of at least 45 degrees when the element 6, 8, 10 is retracted. Stated another way, the elements 6, 8, 10 may apply an angular displacement of at least 45 degrees relative to the ends 24, 26 of the tissue shaper 4 (in addition to longitudinal displacement) when the wire 35 is retracted. This aspect of the invention will be described in greater detail below. The angular displacements or change in angular orientation is accompanied by longitudinal displacement toward the patient's feet and into the stomach of at least 5 cm and is typically 2 to 6 cm.

Figure 3:
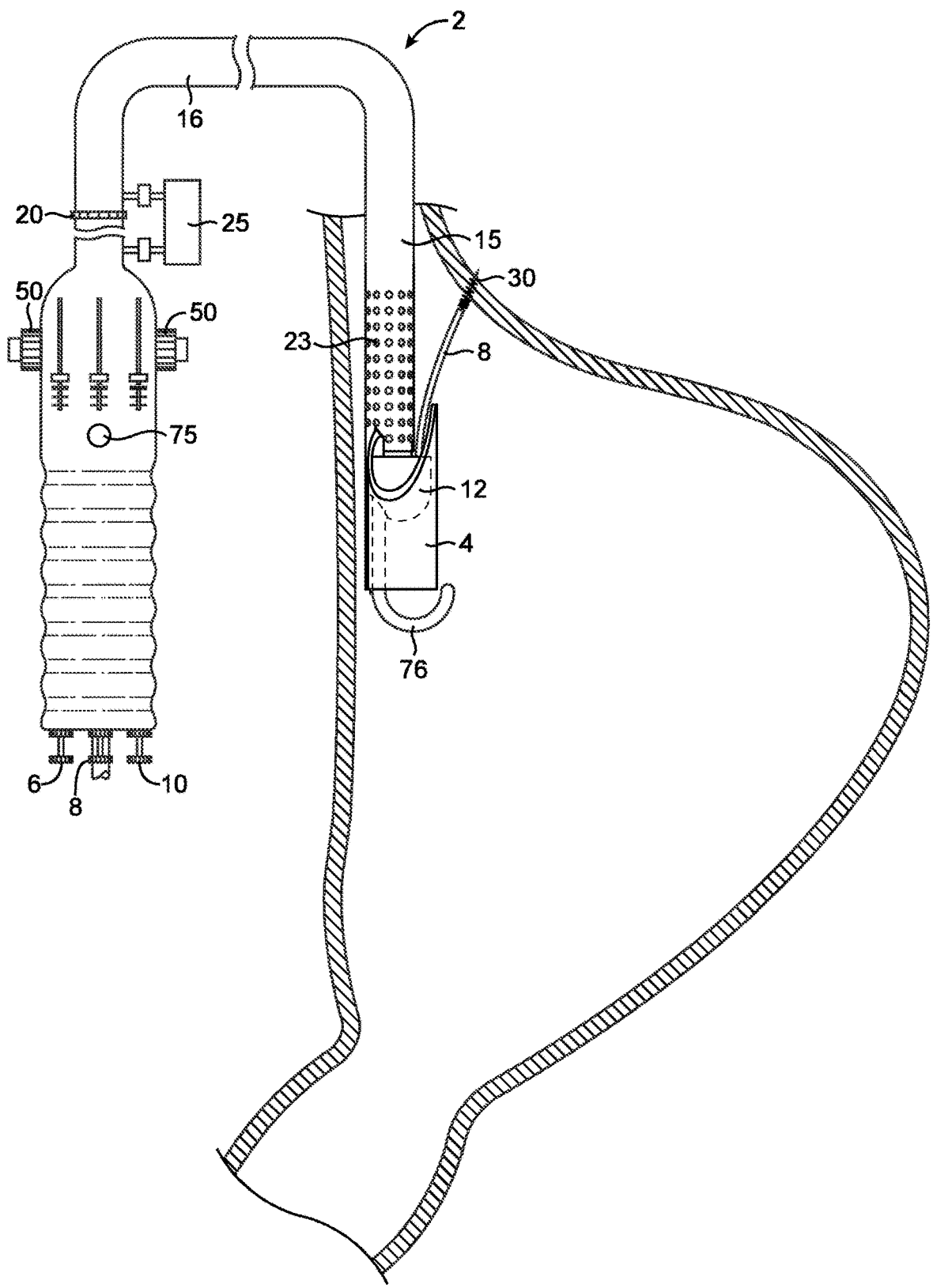
FIG. 3 shows the device inserted into the stomach and a tissue engaging element extended to engage stomach tissue.

Once the helical coil 32 has engaged tissue as shown in FIG. 3, tension is applied to the elongate element 34 to move the stomach tissue toward the tissue shaper 4. The elongate element 34 may be coupled to a tension sensing element, such as a simple spring element 41 shown in dotted line with only element 8, which displays an indication of tension on the elongate element at an indicator 40. Use of the tension indicators 40 is described below in connection with use of the device 2. The tissue engaging element 6, 8, 10 may grip tissue using any other suitable method including graspers or a suction gripper without departing from the scope of the invention. A twist lock 42 is provided to lock each of the tissue displacing elements 6, 8, 10 at any suitable position relative to the secondary shaft 22 and maintain tension on the elongate elements 34.

Figure 16:
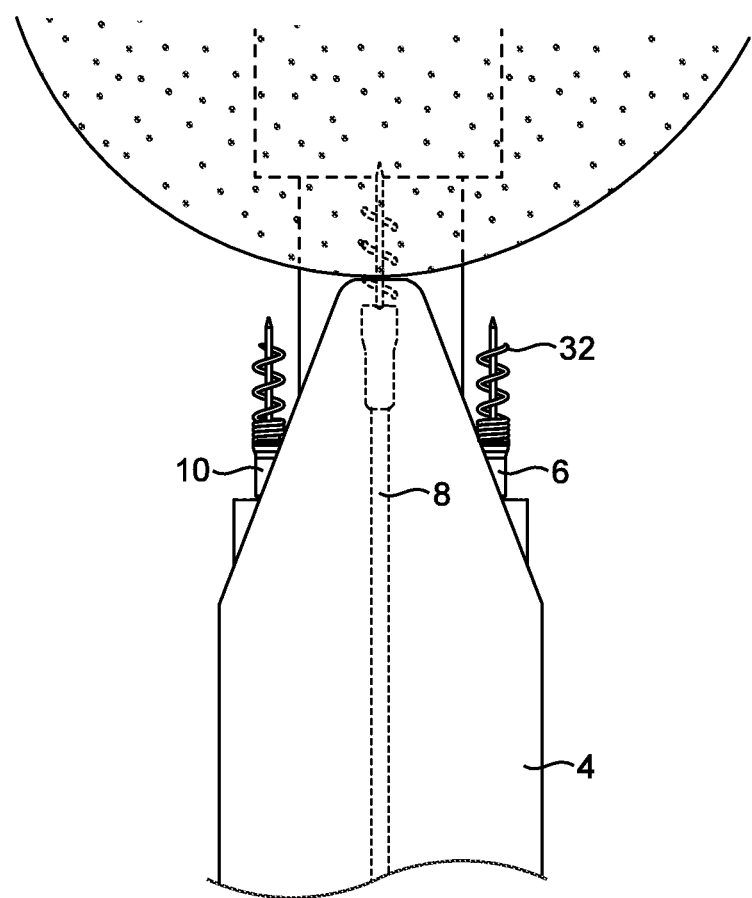
FIG. 16 shows a second tissue displacing element engaging stomach tissue.
Figure 17:
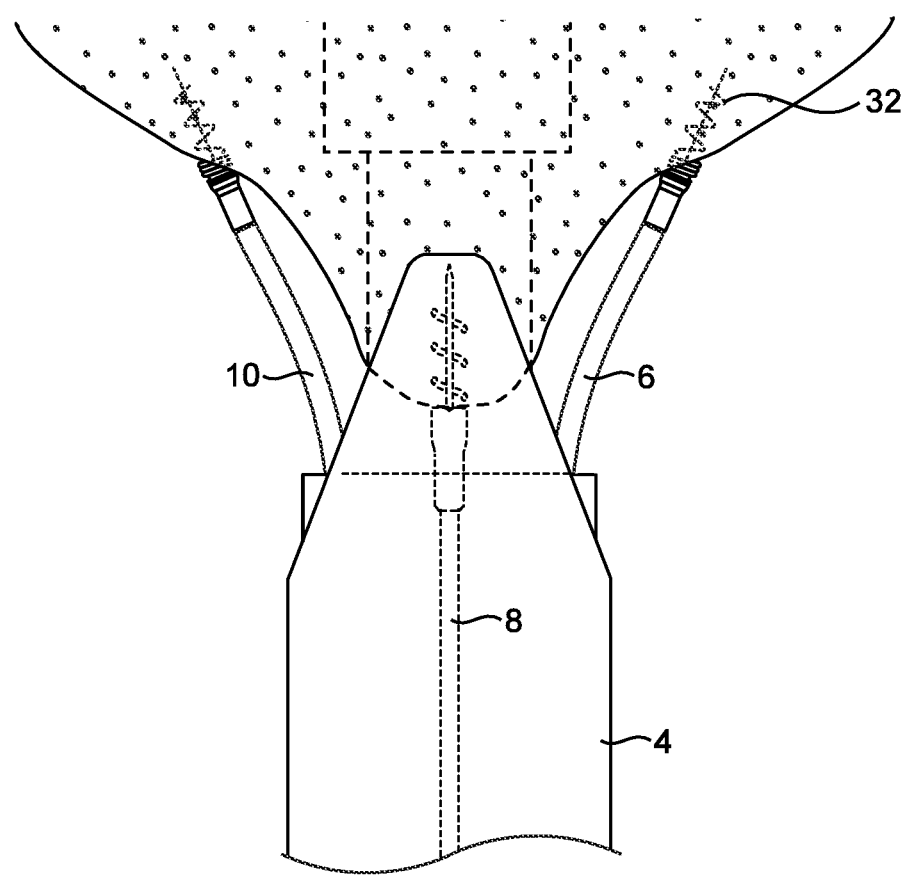
FIG. 17 shows the first and third tissue displacing elements engaging stomach tissue after retracting stomach tissue with the second tissue displacing element.
Figure 18:
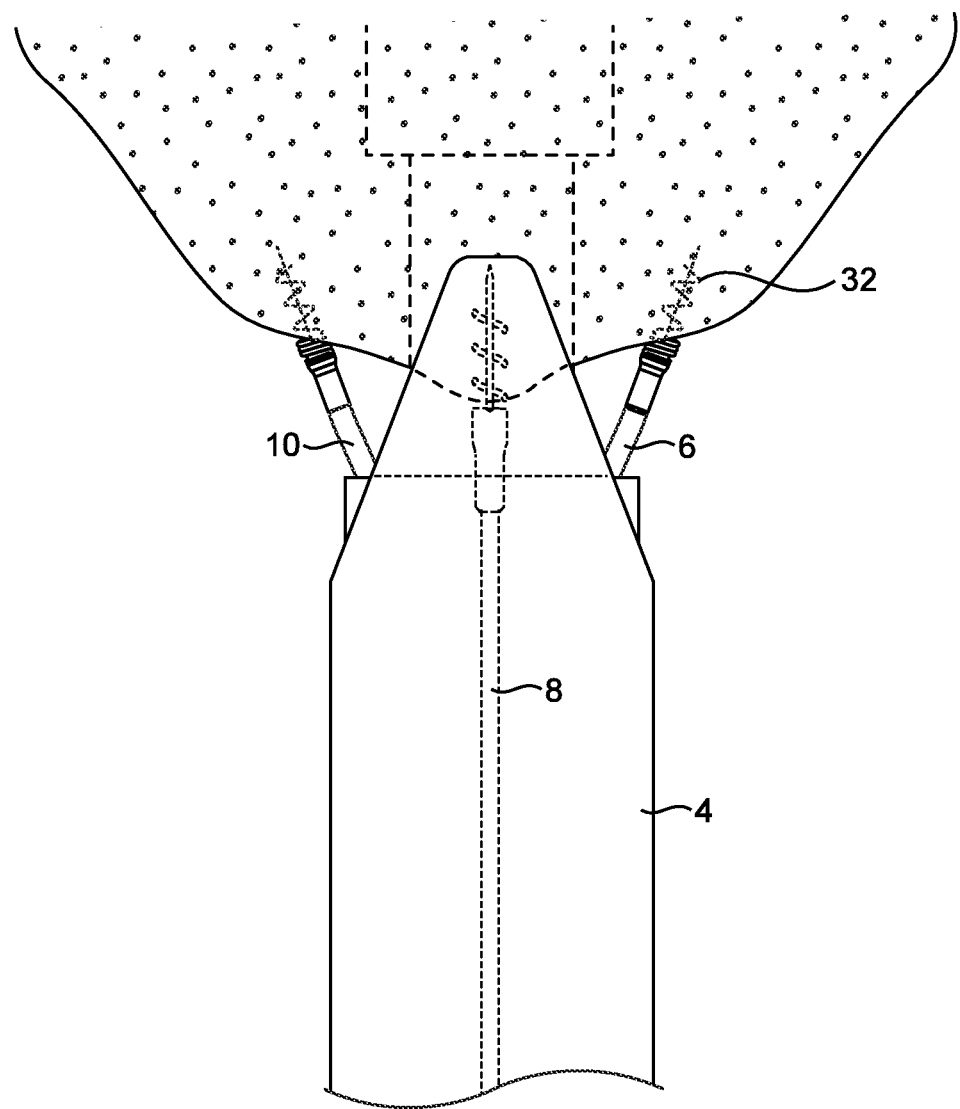
FIG. 18 shows the first and third tissue displacing elements retracting stomach tissue after engagement with tissue in FIG. 17.
Figure 19:
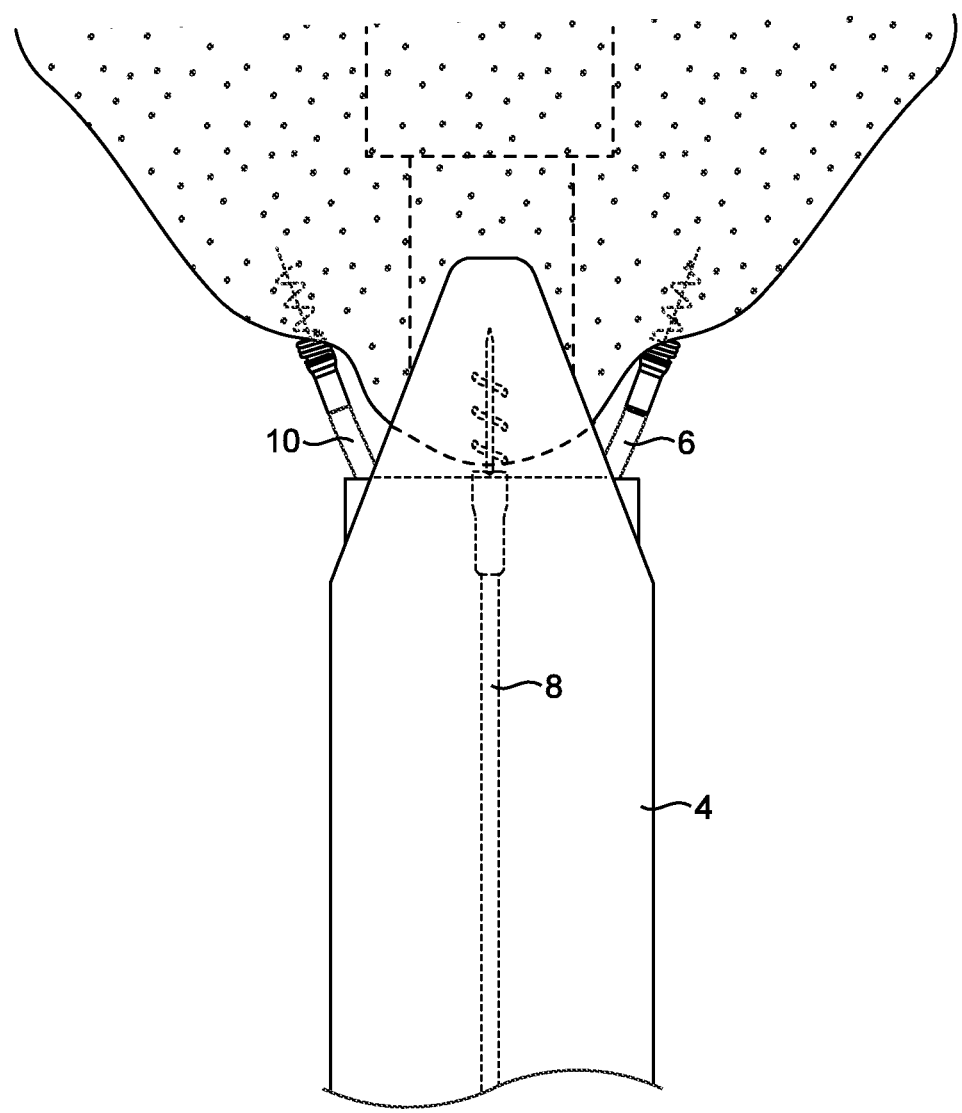
FIG. 19 shows the second tissue displacing element disengaged from stomach tissue, reengaged with stomach tissue and retracted again while the first and third tissue displacing elements maintain the tissue fold.

Referring to FIG. 16, in one aspect of the present invention, one of the tissue displacing elements 6, 8, 10, such as the second tissue displacing element 8, may be displaced until a threshold tension is reached at which time the user applies the appropriate lock 42 (see FIG. 1) to lock the tissue displacing element 8 as shown in FIG. 17. As also shown in FIG. 17, the user may manipulate another of the elements 6, 10 until another threshold tension or displacement is reached at which time the user again applies the appropriate lock 42 as shown in FIG. 18. The second tissue displacing element 8 may then be disengaged, moved, reengaged with tissue and retracted again as shown in FIG. 19. In this manner, the user may continue to individually displace each of the tissue displacing elements 6, 8, 10, while maintaining engagement with the other elements until the desired shape is achieved. The tension indicators 40 may be used with any method described herein even when not expressly described.

The first and third tissue displacing elements 6, 10 are also movable within elongate slots 44 in the platform between the position of FIG. 5 near the ends 24, 26 of the shaper 4 to the position of FIG. 6 closer to the second element 8. The sheath 36 and elongate element 34 are positioned in guide tubes 46 which are movable in the slots 44 by manipulating pull wires 48. The pull wires 48 are coupled to an actuator 50, such as a control knob 51, which is simply rotated to move both pull wires 48 thereby moving the guide tube 46 within the slot 44. A locking button 53 is provided to lock each of the control knobs 51 to fix the position of the pull wires 48 and therefore fix the position of the guide tube 46 anywhere along the slot 44.

The slot 44 permits the tissue displacing element 6, 10 to be moved so that a central axis 56 of the elongate element 34 is displaced at least 45 degrees relative to the longitudinal axis 18 when viewed along the longitudinal axis 18 as shown in FIG. 6 and represented by angle C. Stated another way, a portion 35 (FIG. 1) of the elongate element 34 positioned at the slot 44 which emerges from shaft 15 changes angular position by at least 45 degrees with respect to the longitudinal axis 18. Movement in this manner is typically not possible with conventional multi-link arms and graspers which have a base which may pivot but is fixed in translation relative to the shaft.

The slots 44 may also lie generally on a plane defined by the platform 14 which is substantially perpendicular to the longitudinal axis 18 of the primary shaft 16. Stated still another way, the slots 44 permit the tissue displacing elements 6, 8, 10 to change an angle B formed between each of the first and third tissue displacing elements 6, 10 and the second tissue displacing element 8, or the central plane 28, by at least 45 degrees relative to the longitudinal axis 18. In this manner, the slots 44 may be used to displace tissue toward and away from the ends 24, 26 of the tissue shaper 4. The elongate element 34 may be retracted into the guide tube 46 so that the helical coil 30 is positioned at the slot 44 (see FIGS. 27 and 28). When the coil 30 is positioned at the slot 44, translation of the coil 30 in the slot 44 shifts tissue without longitudinal displacement which is useful in various methods described below.

The tissue shaper 4 of FIG. 4 is configured to shape a fold of tissue to recreate a gastroesophageal flap valve. The tissue shaper 4 has a cavity 50 which receives the tissue. As mentioned above, the tissue can be moved into the cavity 50 by moving the elements 6, 8, 10 or shaper 4 alone or by moving the shaper 4 and elements 6, 8, 10 together.

Referring to FIG. 4, the tissue shaper 4 may include an elastomeric portion 52 on a proximal portion 54 of the tissue shaper 4 which permits the cavity 50 to expand to accommodate tissue. The elastomeric material 52 is positioned at a proximal opening 56 of the cavity 50 so that the opening 56 can elastically expand thereby facilitating introduction of a larger tissue volume while applying a modest compressive force to tissue at the opening 56. The tissue shaper 4 will also increase compression on tissue contained in the cavity 50 as the tissue volume increases. The tissue shaper 4 has an outer wall 58 which may have a plurality of slits 60 formed therein to further increase the flexibility of the tissue shaper 4 and permit expansion of the cavity 50. The slits 60 extend from the proximal end 62 and extend toward a distal end 64 of the tissue shaper 4. The distal end 64 of the tissue shaper 4 also has a distal opening 65 to permit the tissue to extend through the tissue shaper 4 as described below in connection with use of the device 2. The tissue shaper 4 may be a substantially fixed structure except for the elastomeric portion 52, however, the elastomeric portion 52 does provide some movability to the tissue shaper 4 in that the cavity 50 has a first volume during introduction which is less than a volume of the cavity 50 when tissue is introduced into the expandable cavity 50. As such, the tissue shaper 4 does change shape even though the tissue shaper 4 is not movable by the user. Although the tissue shaper 4 is shown as a structure, which is not moved by the user, the tissue shaper 4 may be movable by the user to close the tissue shaper 4 (not shown) around the fold of tissue without departing from numerous aspects of the present invention.

Figure 32:
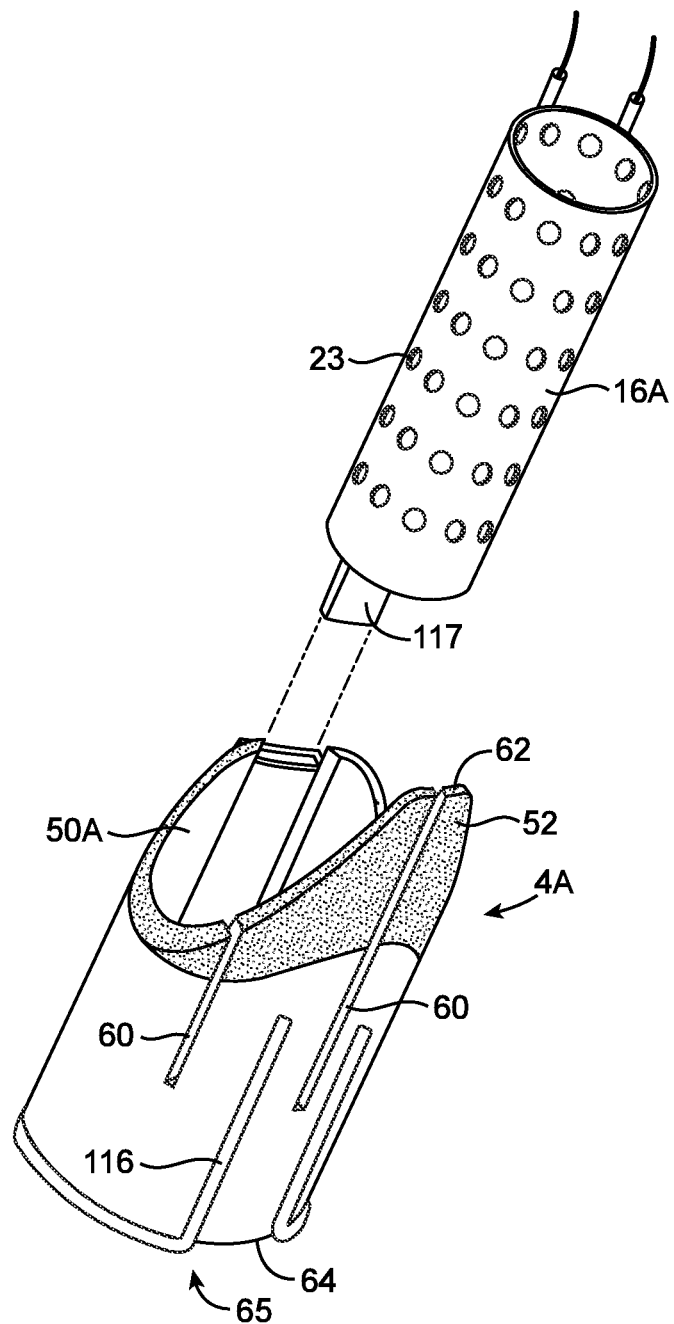
FIG. 32 shows the device with a removable tissue shaper attached to the shaft.
Figure 33:
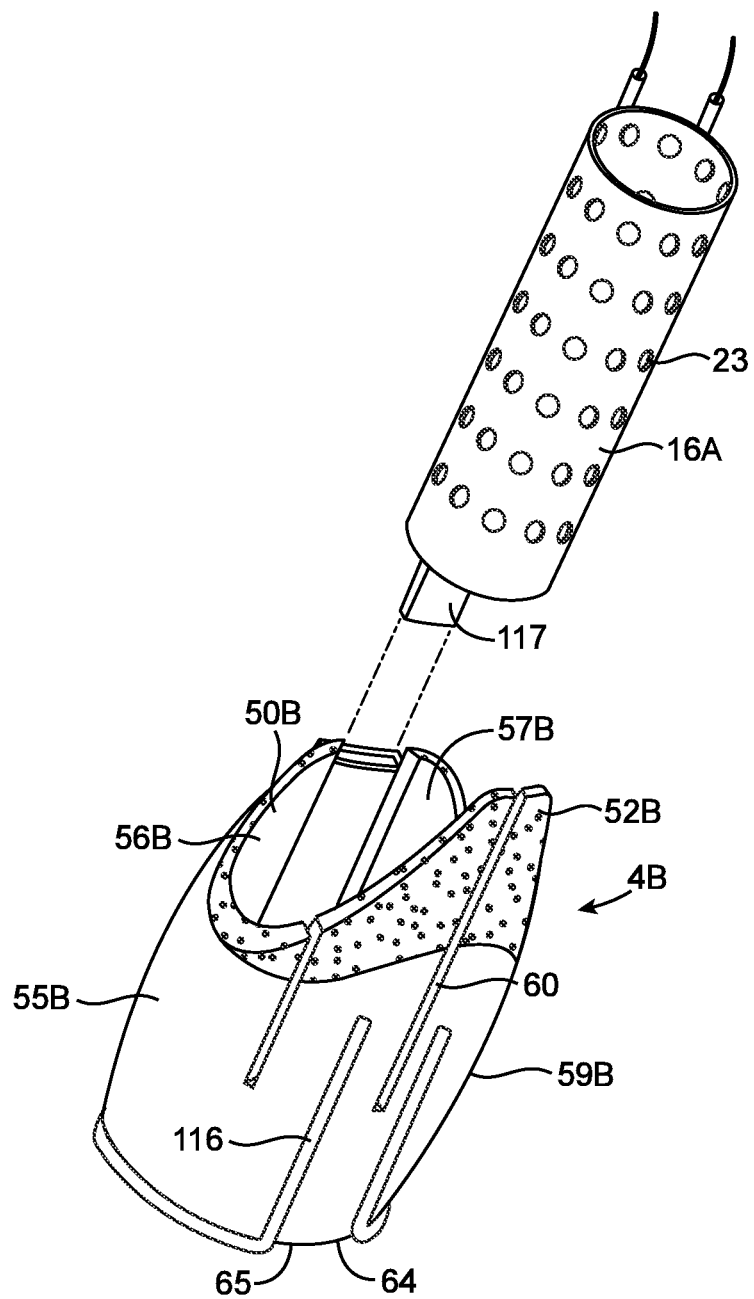
FIG. 33 shows the device with another tissue shaper attached to the shaft.
Figure 34:
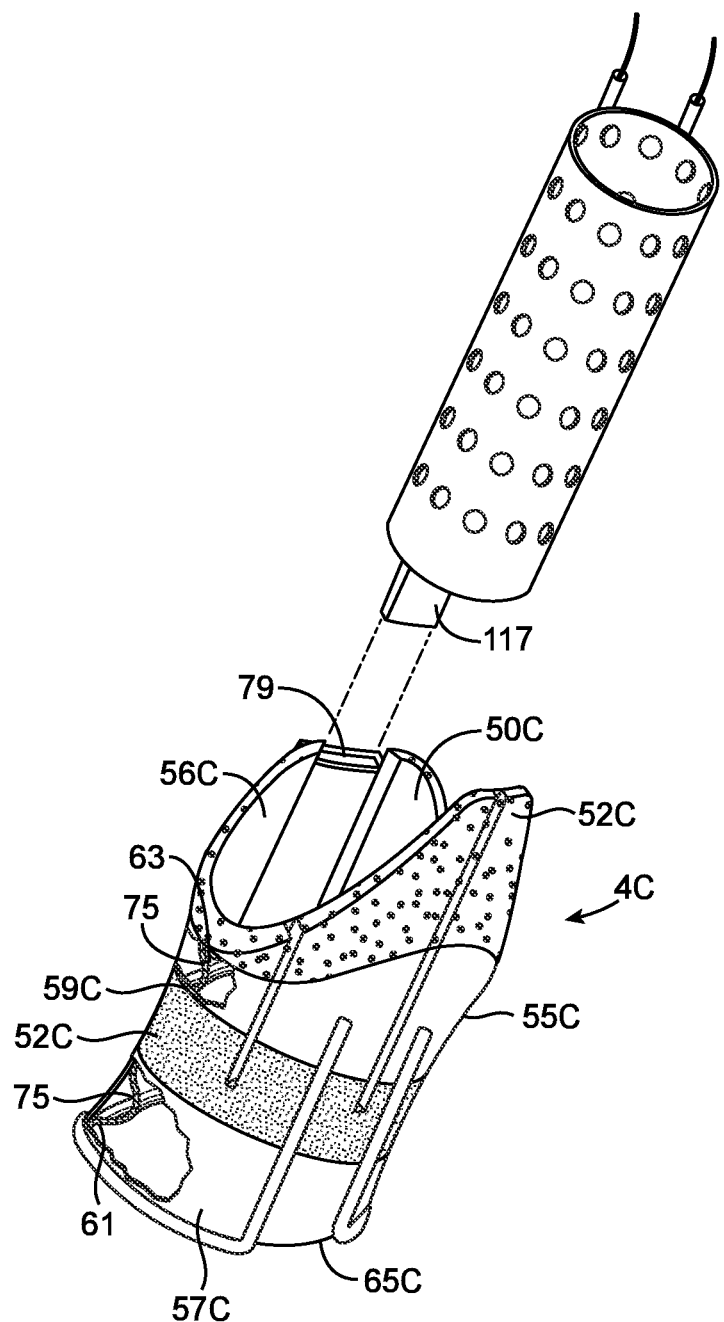
FIG. 34 shows the device with still another tissue shaper attached to the shaft.

Referring now to FIG. 32, a removable tissue shaper 4A is attached to a primary shaft 16A. The tissue shaper 4A may be removably attached to the shaft 15 in any suitable manner such as a simple snap-fit connection 117 or bayonette connection (not shown). Referring to FIGS. 33 and 34, two more tissue shapers 4B, 4C are shown with the tissue shapers 4A, 4B, 4C being interchangeable and usable in any manner that tissue shaper 4 is used. The user may decide upon which tissue shaper 4A, 4B, 4C to use prior to beginning the procedure and attach the appropriate tissue shaper 4A, 4B, 4C to the shaft 16A. Alternatively, the user may begin the procedure with one of the tissue shapers 4A, 4B, 4C and may decide to change to another shaper (different shape and/or size). The present invention provides the ability to change shapers 4A, 4B, 4C or select the appropriate shaper 4A, 4B, 4C from available shapes and sizes.

The tissue shaper 4, 4A may have substantially straight edges, forming an acute angle, symmetrically disposed about the longitudinal axis 18 (see FIG. 1 and FIG. 16). Alternatively, the profile edges could be convex or concave, or any combination of concave, convex or straight edged profiles as now discussed in connection with tissue shapers 4B, 4C of FIGS. 33 and 34. Referring to FIG. 33, for example, tissue shaper 4B has a convex outer wall 55B which creates a cavity 50B also having a convex outer wall 57B. A proximal opening 56B leading to the cavity 50B has a smaller cross-sectional shape than a midportion 59B of the cavity 50B. In this manner, the cavity 50B may be sized to hold the fold of tissue more loosely in the midportion 59B so that the tissue in the midportion 59B may be manipulated more easily within the cavity 50B while the tissue fold is still being firmly held by the proximal opening 56B. Use of elastomeric portion 52B may be particularly advantageous in holding tissue firmly at the proximal opening 56B.

Referring to FIG. 34, tissue shaper 4C has a concave outer wall 55C and a cavity 50C having a concave outer wall 57C. The cavity 50C has a proximal opening 56C, a distal opening 65C and a midportion 59C. The midportion 59C has the smallest cross-sectional shape throughout the cavity 50C so that tissue contained in the cavity 50C may be held more firmly by the midportion 59C. An elastomeric portion 52C of the shaper 4C may be adjacent the midportion 59C which provides the advantages described above in connection with tissue shaper 4. Holding tissue within the shaper 4C in this manner may facilitate gathering tissue using various methods described herein. For example, the tissue shaper 4C may hold the fold of tissue firmly at the midportion 59C so that tissue near the distal opening 65C and extending through the distal opening 65C may be manipulated.

The tissue shaper 4C also includes a first clamping element 61 and a second clamping element 63 (shown in dotted-line position). The first and second clamping elements 61, 63 may be elastic balloons 75 but may be any other suitable mechanism such as a pivoting jaw. FIG. 34 shows the balloons 75 partially inflated to clamp tissue contained in the tissue shaper 4C. The first clamping element 61 is positioned near the distal end and the second clamping element 63 is positioned along the midsection although any number of clamping elements (including only one) may be used. An inflation lumen 79 is coupled to the balloons 75 and extends through the connector 117 but may be a separate lumen as well. It is understood that the clamping elements 61, 63 may be incorporated into any of the other tissue shapers 4, 4A, 4B and use of the clamping elements 61, 63 with the any of the other tissue shapers 4, 4A, 4B is expressly incorporated here.

The clamping element 61, 63 may be used to hold tissue contained within the tissue shaper 4C and may be clamped and unclamped as desired. As such, the balloons 75 may be deflated during the tissue displacing steps and inflated to hold tissue after the displacing step. Thus, all methods described herein may include deflating the balloon 75 prior to displacing tissue and/or may include inflating the balloon 75 after each displacing step. The clamping elements 61, 63 may also be used to hold tissue during application of fasteners and, to this end, each method described herein may include the step of clamping the tissue fold together before fastening the fold together. The clamping element 61, 63 may be released and again reapplied before each fastening step as desired and, again, all methods described herein shall expressly provide for the clamping steps described herein.

As mentioned above, the common retractor 12 and platform 14 are coupled to the secondary shaft 22 so that the platform 14 may be moved relative to the shaper 4. Movement of the secondary shaft 22 and the platform 14 also moves all three of the tissue displacing elements 6, 8, 10 simultaneously. The secondary shaft 22 includes lumens 66 which receive the tissue displacing elements 6, 8, 10 and pull wire lumens 68 which receive the pull wires 44 for the guide tubes 46 (FIGS. 5 and 6). A suction lumen 70 may also be provided which is coupled to vacuum orifices 72 in the platform 14. The vacuum orifices 72 and vacuum orifices 23 in the primary shaft 16 are coupled to a suction source 71 as shown in FIG. 1 and are independently controllable as is known in the art.

A visualization lumen 74 is formed between the primary and secondary shafts 16, 22 in which a visualization device 76 may be positioned. The visualization device 76 may be any suitable device and suitable devices are described in U.S. Pat. No. 7,583,872, Compact Scanning Fiber Device and U.S. Pat. No. 6,275,255, Reduced Area Imaging Devices. In one aspect of the present invention, the lumen 74 which receives the visualization device 76 is no more than 10% of a total cross-sectional area of the shaft 15. In one embodiment, the visualization lumen 74 may have a diameter of about 5 mm and the primary shaft 16 has a cross-sectional area of about 255 mm2. A lock 75 is also provided to couple movement of the first and third tissue displacing elements 6, 10 together as described below in connection with various methods of the present invention.

The tissue, or parts, thereof, may be stabilized or engaged within the tissue shaper 4, or even outside the tissue shaper 4, using the tissue displacing elements 6, 8, 10, the vacuum orifices 72 in the platform 14 or the vacuum orifices 23 on the primary shaft 16. Furthermore, it is understood that stabilizing tissue between tissue manipulations or fastening steps with any one of these elements may be practiced with any of the methods described herein even if not specifically described. For example, some methods of the present invention describe stabilizing tissue with the second tissue displacing element 8 while moving tissue with the first and/or third tissue displacing elements 6, 10 and such methods may be practiced by stabilizing tissue with any other suitable element such as the vacuum orifices 23 on the primary shaft 16 or vacuum orifices 72 in the platform 14 and such methods are expressly included as part of the invention.

The tissue shaper 4 may be sized to firmly hold the fold of tissue once the fold of tissue has been drawn into the cavity 50 while still permitting some movement of the tissue within the tissue shaper 4. Shifting tissue within the tissue shaper 4, as used herein, shall mean that the tissue shaper 4 holds the fold of tissue so that at least part of the tissue is approximated and in contact with one another prior to fastening but are still held loosely enough to shift tissue within the tissue shaper 4 and/or draw tissue into the tissue shaper 4.

Figure 8:
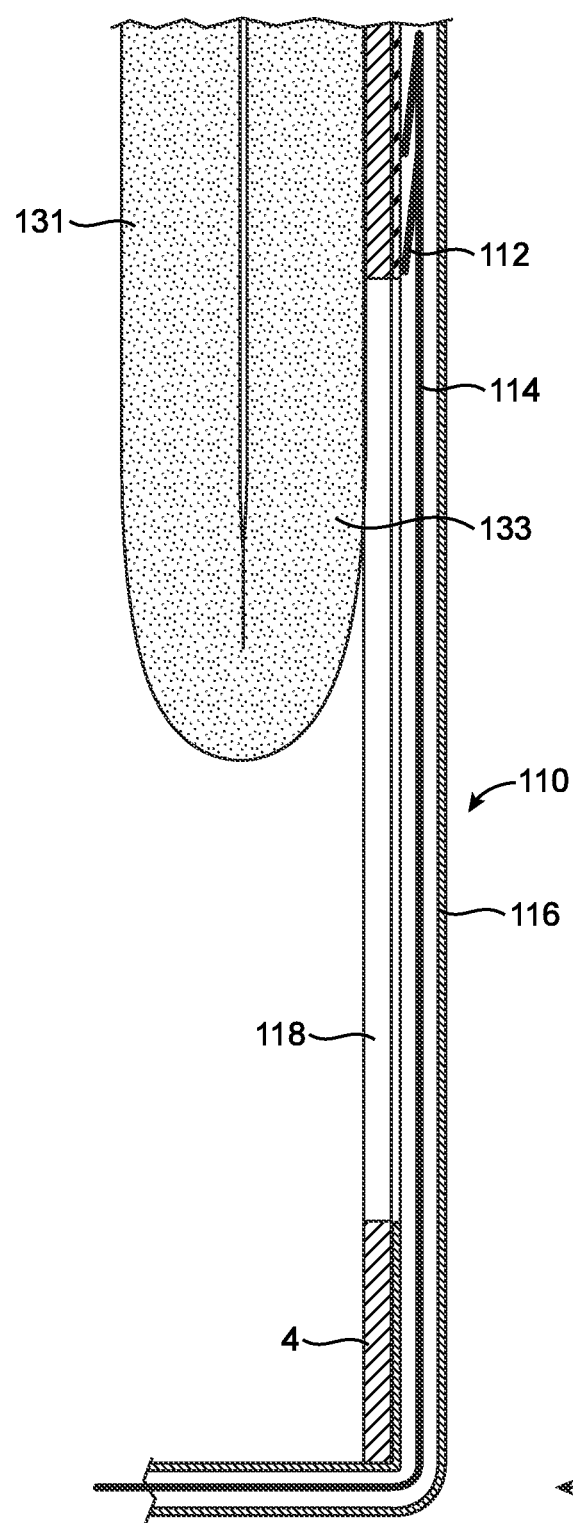
FIG. 8 shows a tissue shifting element in a stored position.
Figure 9:
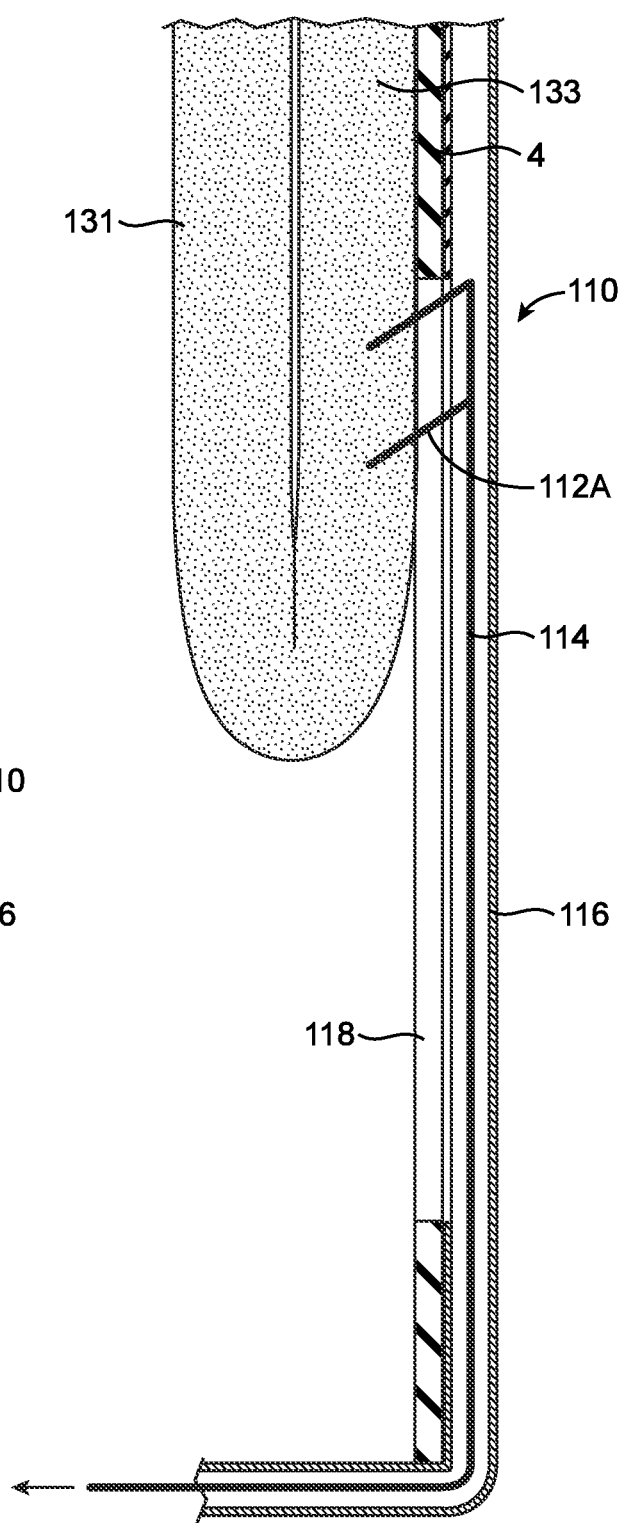
FIG. 9 shows the tissue shifting element engaging one tissue layer of the tissue fold.
Figure 10:
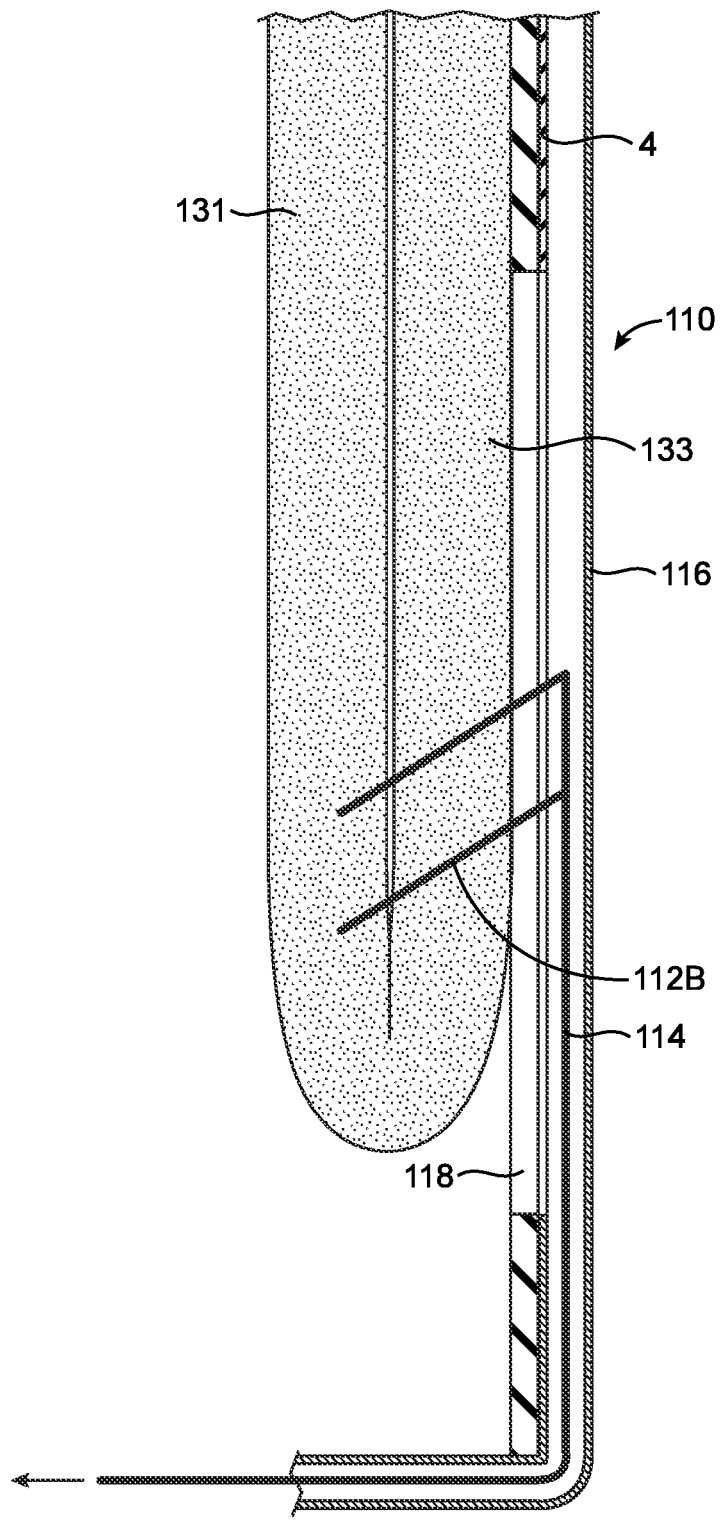
FIG. 10 shows the tissue shifting element engaging both tissue layers of the tissue fold.

Referring to FIGS. 8-10, one structure which may be used to move or shift tissue within the tissue shaper 4 is a tissue shifting element 110. The tissue shifting element 110 is coupled to the tissue shaper 4 and provides a mechanism for shifting tissue within the tissue shaper 4 without moving the tissue shaper 4 and preferably without moving the primary or secondary shafts 16, 22. The tissue shifting element 110 includes a pair of needles 112 mounted on a wire 114. The needles 112 may be coupled to the wire in any suitable manner; for example, the needles may pivotally engage the wire 114 or may have an integrally formed hinge with the wire 11. The device 2 may include two sets of needles 112. One set of needles 112A may pierce one tissue layer (FIG. 9) and the other set of needles 112 may penetrate both layers of the tissue fold (FIG. 10). Each wire 114 extends through a tube 116 having an open slit 118 through which the needles 112, 112A extend. When the wire 114 is advanced to the position of FIG. 8, the needles 112 are collapsed within the tube 116. When the wire 114 is moved proximally, the needles 112 naturally expand outwardly through the slit 118 and further proximal motion causes the needles 112, 112A to penetrate one or both tissue layers. The tissue shifting element 110 may engage the tissue with any other suitable mechanism including a movable suction port. Tissue may also be shifted within the tissue shaper 4 using elements 6, 8, 10 which may apply longitudinal and/or angular displacements as described herein. For example, the elements 6, 8, 10 may displace tissue further into the cavity 50 and displace tissue towards or away from the ends 24, 26 of the shaper 4 by moving the elements 6, 10 within slots 44. As such, the displacing elements 6, 8, 10 may also constitute tissue shifting elements for shifting tissue within the tissue shaper 4 as used herein. The tissue shifting element 110 is omitted for clarity in various drawings but all drawings including the tissue shaper 4 shall be interpreted to include the tissue shifting element 110.

Any suitable fastener may be used with the present invention and, in fact, numerous aspects of the present invention may be practiced with any other suitable fastening method such as adhesive or suture. Several suitable fastener appliers are described below in connection with FIGS. 11-14. Although the fastener applier is a separate device delivered down the fastener lumen 74, numerous aspects of the present invention may be practiced with the fastener applier being integrated into the device 2 rather than being a separate device. An advantage of providing a separate fastener applier is that the device 2 may be advanced down the patient's esophagus without the fastener applier positioned in the fastener lumen 74 which may provide a more flexible device for introduction than would a device having the fastener applier integrated into the device 2. The fastener lumen 78 includes a window 80 in the primary shaft 16 so that the fastener may be applied anywhere along an arc of at least 90 degrees, and may be at least 120 degrees, relative to the longitudinal axis 18 without moving the shaft 15 or the tissue shaper 4. The fastener lumen 74 may also include a ramp 80 which causes the fastener applier to be displaced radially outward from the longitudinal axis 18 to compress the fold of tissue prior to delivery of the fastener as described below and shown in FIG. 12.

Figure 11:
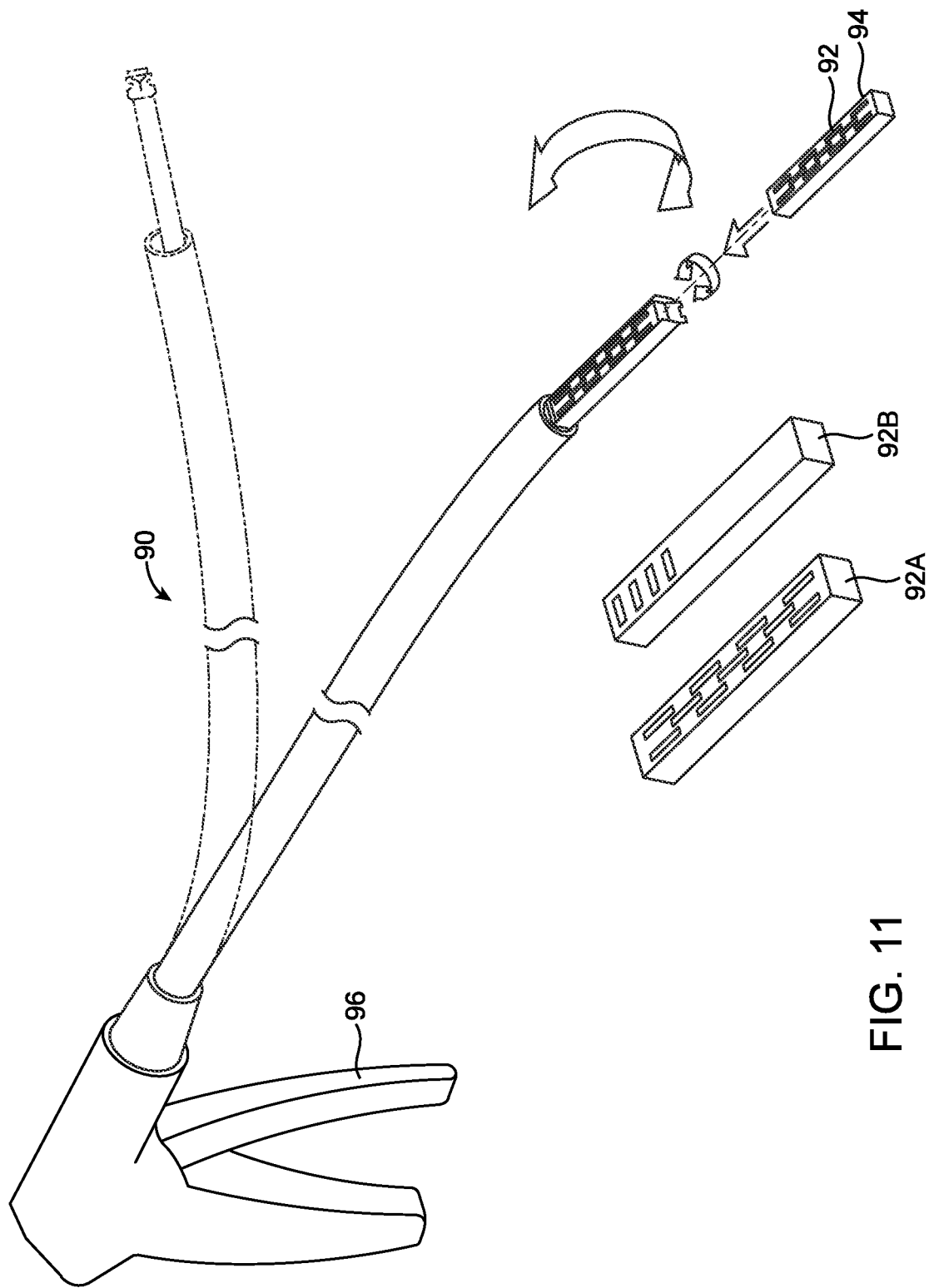
FIG. 11 shows a fastener applier, which may be used with the present invention.

Referring now to FIG. 11, a fastener applier 90 is shown. The fastener applier 90 includes a cartridge 92 containing a plurality of fasteners such as staples 94. An actuator 96 is coupled to a firing mechanism which is actuated to deploy the fasteners in any suitable fashion as is known in the art. The fastener applier 90 may be configured to deliver a plurality of staples 94 simultaneously and, in particular, in a longitudinal orientation. Different cartridges 92A, 92B may be provided to dispense a different number or orientation of staples 94 as desired and methods of the present invention may provide for sequential use of the cartridges 92, 92A, 92B. The fastener applier 90 may also be longitudinally movable with respect to the tissue shaper 4 and the primary shaft 16 so that the fastener applier 90 may be used at different longitudinal positions without moving the primary shaft 16 and/or the tissue shaper 4. Numerous aspects of the present invention may be carried out with the tissue fold being fastened in any suitable manner including use of an adhesive or conventional suture rather than discrete fasteners. Additional aspects of the fastener applier 90 are described in connection with use of the device.

Figure 12:
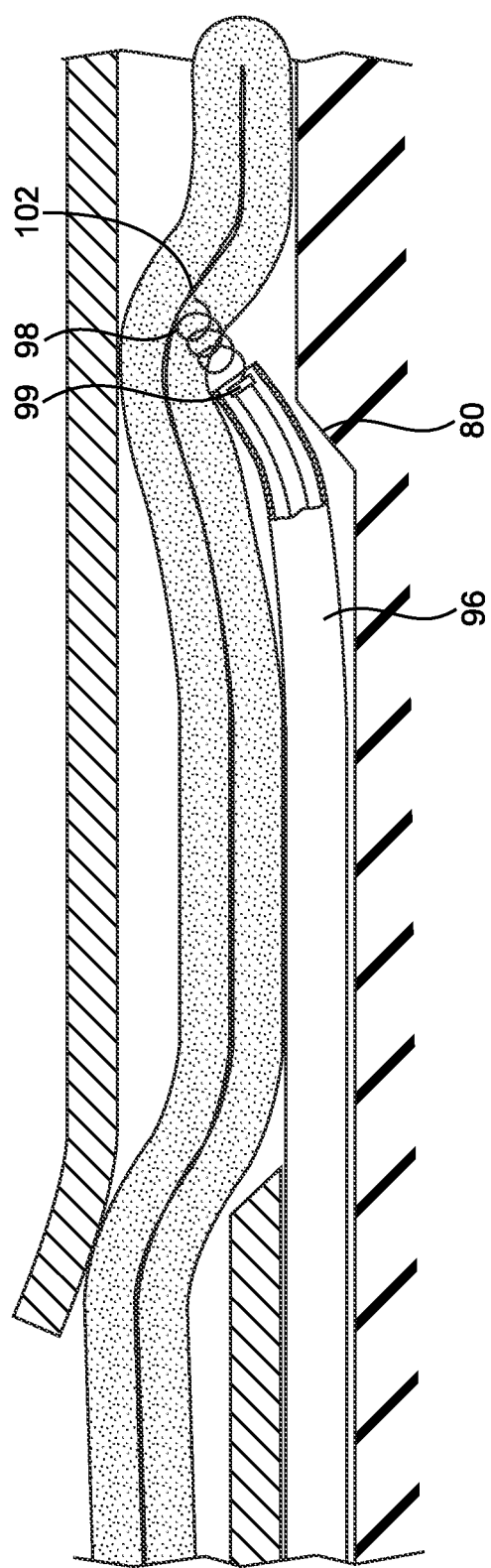
FIG. 12 shows another fastener applier.

Another fastener applier 96 is shown in FIG. 12. The fastener applier 96 contains a helical fastener 98 which is rotated into engagement with tissue using an actuator 99. The fastener applier 96 has an open distal end 100 which is directed toward the tissue by the ramp 80 to further compress the tissue fold prior to application of the fastener 98. The helical fastener 98 is rotated and advanced with the actuator 99 so that a sharp tip 102 penetrates and advances into the tissue fold. After application of the helical fastener 98, another fastener applier 96 is used or another fastener 98 is delivered down the same applier 96.

Figure 13A:
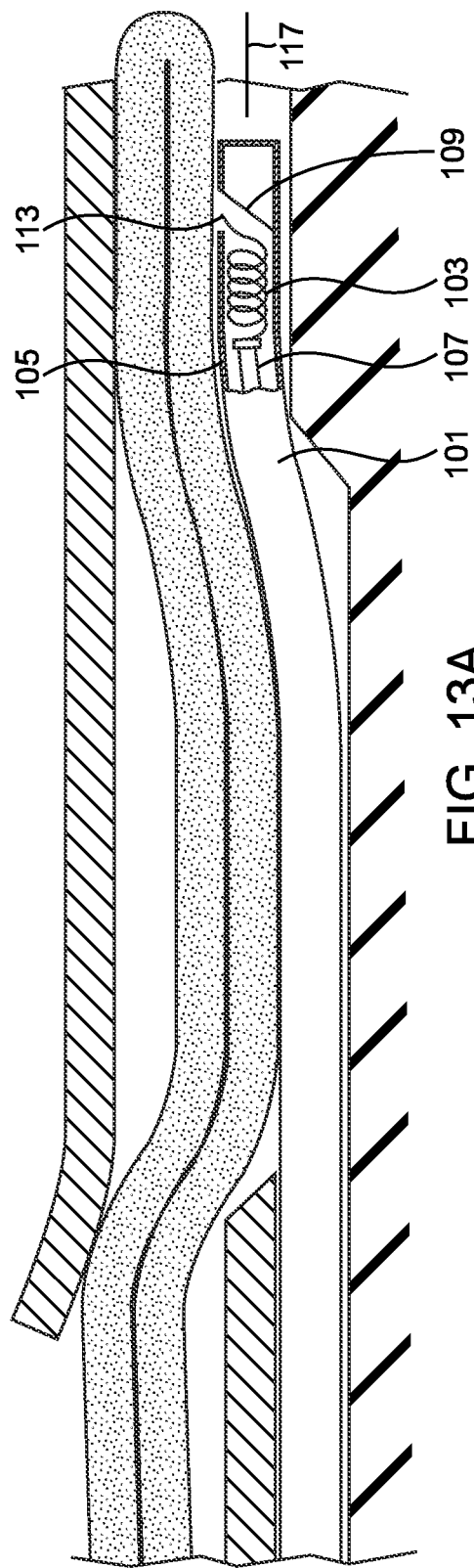
FIG. 13A shows another fastener applier prior to delivery of the fastener.
Figure 13B:
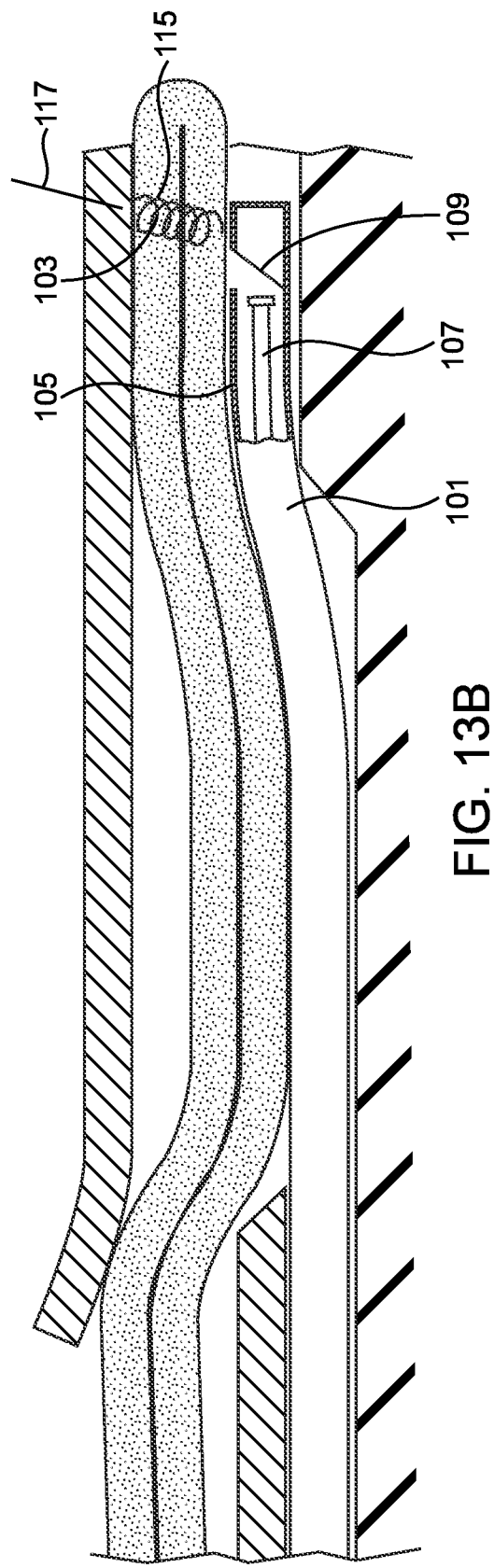
FIG. 13B shows the fastener of FIG. 13A delivered into the tissue fold.

Referring to FIGS. 13A and 13B, yet another fastener applier 101 is shown which delivers a helical fastener 103. The fastener 103 has a sharp tip 113 and form a number of coils 115 which define an axis 117. The fastener 103 is oriented longitudinally within a shaft 105 of the applier but is deployed in a manner which reorients the axis 117 upon deployment. An actuator 107 rotates and advances the helical fastener 103 which causes the helical fastener 103 to contact a deflecting element 109 which deflects the fastener 103 outwardly from the shaft 105 and into tissue. As the helical fastener 103 is deployed, the deflecting element 109 causes the axis 117 to be displaced at least 45 degrees from the stored position within the shaft to the deployed position outside the shaft 105.

Figure 14:
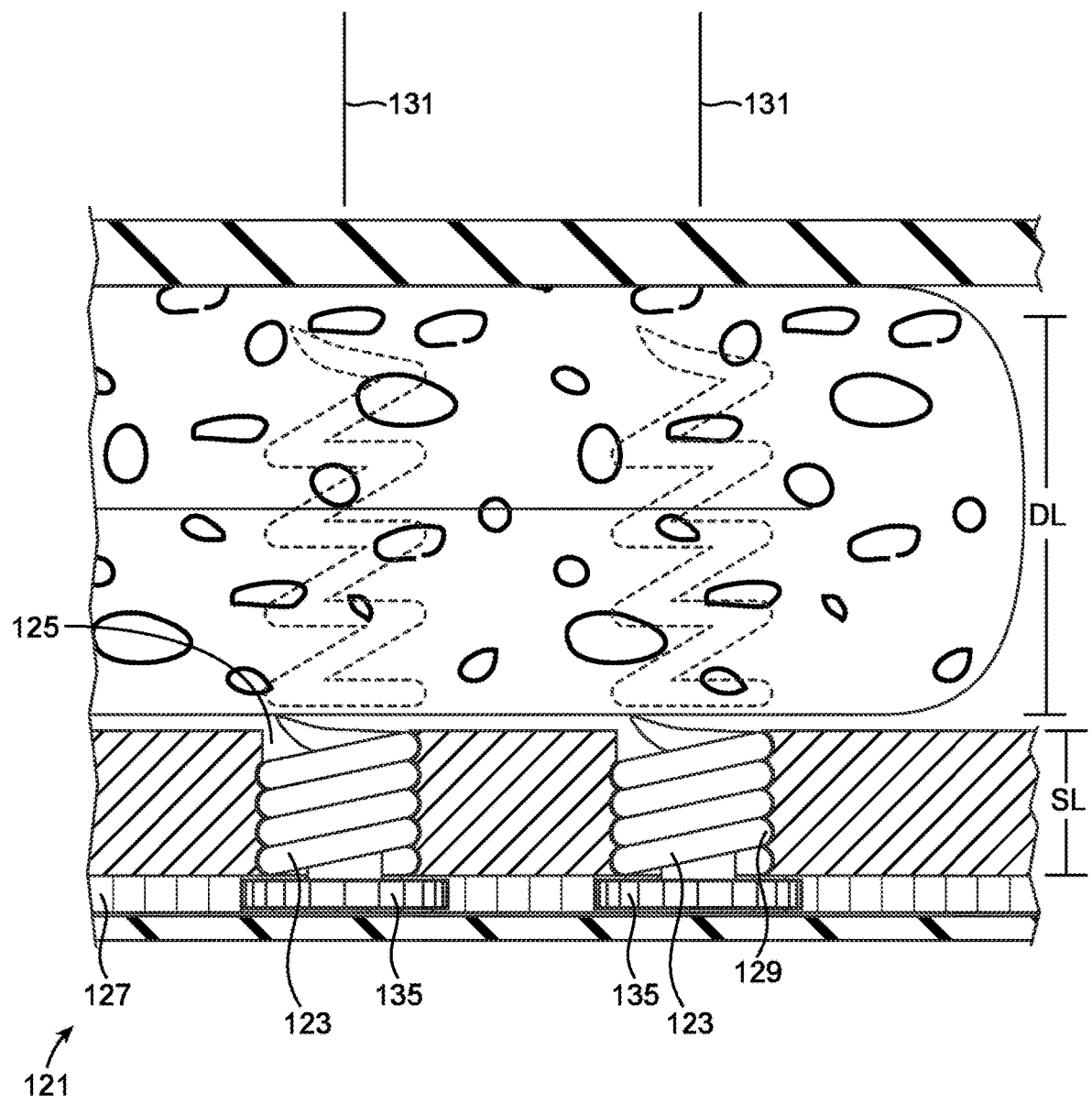
FIG. 14 shows still another fastener applier.

Referring to FIG. 14, still another fastener applier 121 is shown which delivers a plurality of helical fasteners 123. The fasteners can be delivered sequentially or simultaneously. The helical fasteners 123 forms a plurality of coils 129 which define an axis 131 and a length measured along the axis 131. The helical fasteners 123 are deployed through one or more side openings 125 upon movement of a rack 127 that rotates a gear 135 coupled to the fasteners 123 so that simple longitudinal motion of the rack 127 rotates all of the fasteners simultaneously. The fasteners 123 may be compressed in a stored position within the shaft 125 so that a natural unbiased length of the fastener 123 is at least 1.5 times, or even 2.0 times, a stored length (or compressed length) SL of the fasteners 123 within the shaft. As the fastener 123 is deployed, the fastener 123 naturally expands toward the natural unbiased length. In another aspect, the opening 125 may be oriented to direct the fastener 123 into an even larger length than the unbiased length by simply applying a greater pitch upon delivery through the opening. In this manner, the coils 129 are initially expanded so that tissue between the coils is compressed as the fastener 123 is deployed. For example, the fastener applier 121 may be configured to deploy the fastener 123 at a deployed length DL which is 2.5 times the stored length SL while the relaxed or unbiased length is 2.0 times larger than the stored or compressed length SL.

Methods of using the device 2 are now described. As will be appreciated, the present invention provides great flexibility in the manner in which the fold of tissue is formed and fastened together. As such, all methods of forming the fold shall be applicable to all methods of fastening the tissue together and such combinations are expressly included as part of the present invention even if not expressly described. Furthermore, all methods of manipulating tissue which are described in connection with moving tissue within or into the tissue shaper 4 may be practiced without the tissue shaper 4 or below the tissue shaper 4 and all such methods are expressly incorporated herein.

Figure 15:
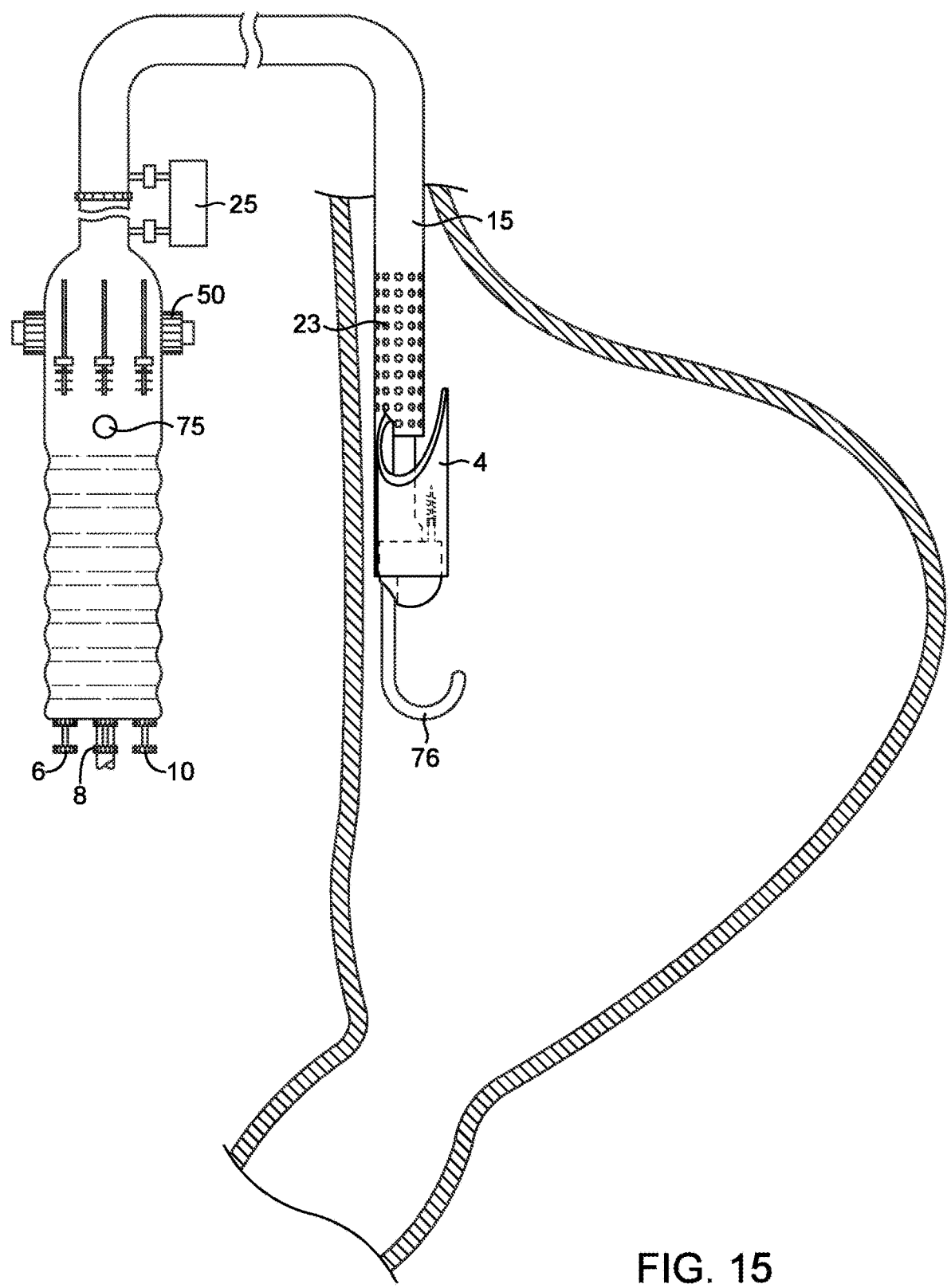
FIG. 15 shows the device delivered into the stomach and positioned in a desired location to recreate the intersection between the stomach and esophageal tract.

The device 2 is delivered down a patient's esophagus into the position of FIG. 15 so that the tissue shaper 4 is distal to the existing intersection between the esophageal tract and the stomach associated with a disease state. The visualization device 76 is used to view the stomach and orient the tissue shaper 4 within the stomach so that the tissue shaper 4 is positioned to create the fold of tissue in the desired position. An advantage of the present invention is that the user may not need to reposition the tissue shaper 4 once the desired position has been chosen. Of course, numerous aspects of the present invention may be practiced while moving the tissue shaper 4 between different positions without departing from the scope of the invention. For example, the tissue shaper 4 could be used to gather and fasten tissue into a fold and could be rotated to another position to create another fold.

Figure 20:
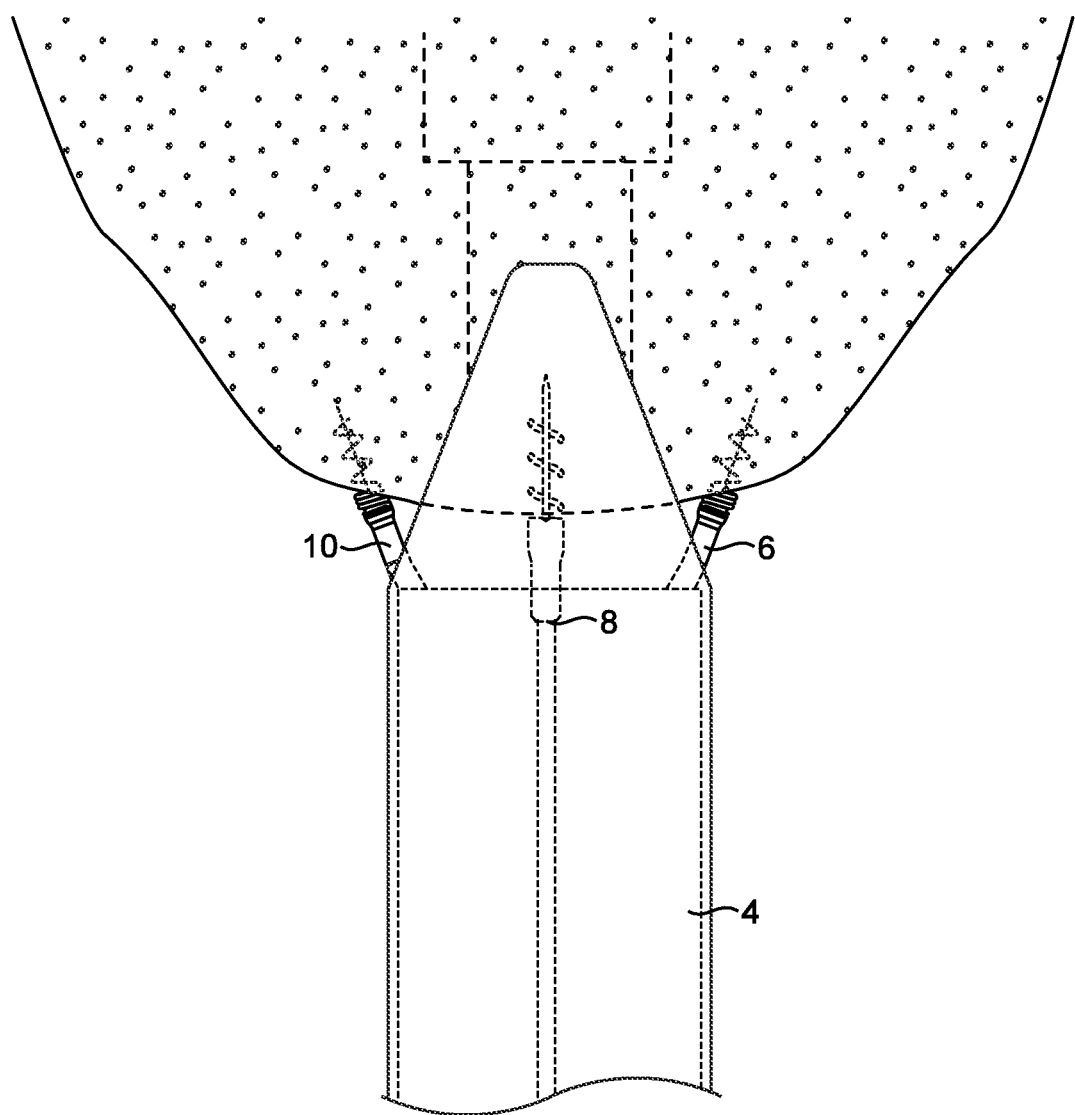
FIG. 20 shows all three tissue displacing elements engaged with tissue and positioned proximate a common retractor.

At least one of the tissue displacing elements 6, 8, 10, such as the second tissue displacing element 8, is then extended outwardly to engage stomach tissue as shown in FIG. 3. The sheath 36 may be extended to cover the wire 35 to change the shape of the wire 35 to provide a different shape to facilitate engaging the desired stomach tissue location (see FIG. 7). The coil 32 is then rotated to engage the stomach tissue. Referring to FIGS. 1, 3 and 16, the second tissue displacing element 8 may then be pulled to draw stomach tissue toward the tissue shaper 4 which increases tension on the elongate element 34 and registers at the tension indicator 40. The user may refer to the tension indicator 40 to assist in assessing formation of the fold and the forces which may be required to maintain the fold. The user may retract the tissue displacing element 8 until a threshold tension is reached at which time the lock 42 is applied to maintain tension as shown in FIG. 17. The user may then engage stomach tissue with another of the elements 6, 10, such as the first element 6, and retract tissue until another threshold tension is reached, or desired displacement is achieved, and the appropriate lock 42 is applied as shown in FIG. 18. This process may be repeated until the stomach tissue has been displaced a desired amount by each of the tissue displacing elements 6, 8, 10 (see FIGS. 19 and 20).

An advantage of the present invention is that a stepwise displacement of tissue is possible since the plurality of elements 6, 8, 10 permit one of the elements 6, 8, 10 to be disengaged from tissue while the other two elements 6, 8, 10 substantially maintain the shape of the previously displaced tissue. In this manner, one of the elements 6, 8, 10, such as the second element 8, may be disengaged, repositioned to engage stomach tissue and displaced again as shown in FIGS. 18 and 19. The displaced stomach tissue may also be held by the vacuum orifices 23 in the primary shaft 16 (FIG. 1), the vacuum orifices 72 in the platform 14 (FIG. 5) and/or the tissue shaper 4 in addition to, or as a substitute for, the first and third tissue displacing elements 6, 10 which hold the tissue in a displaced state of FIG. 18. During displacement of stomach tissue, the elements 6, 8, 10 may displace the tissue by simply applying tension to the wire 35 and/or moving them within the slots 44 (FIGS. 5 and 6). For example, the first tissue displacing element 6 may be retracted until the coil 32 is proximate to the platform 14 followed by movement within the slot 44 to change the angular orientation as described herein.

Figure 21:
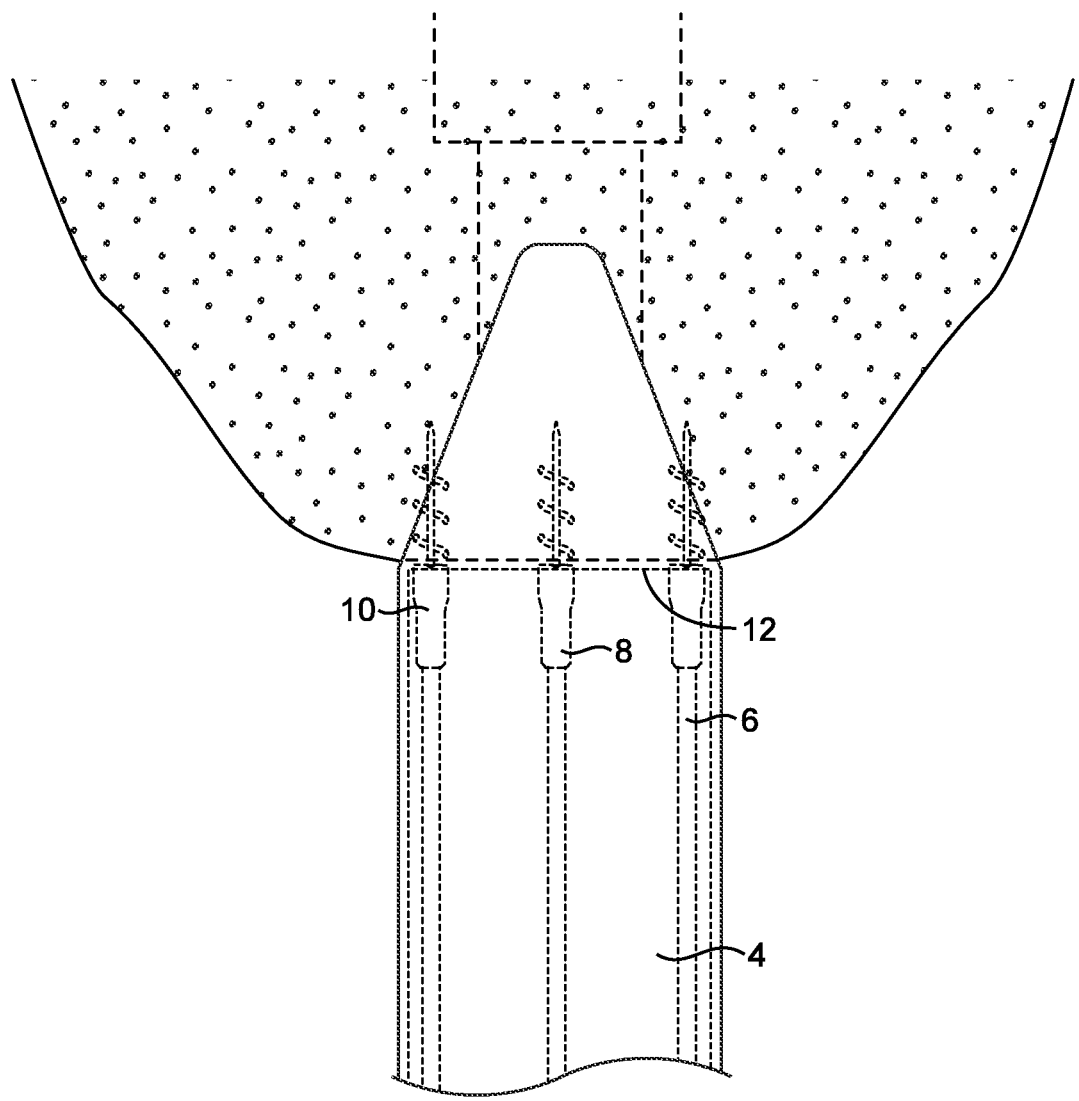
FIG. 21 shows all three tissue displacing elements engaged with tissue and retracted to the common retractor.
Figure 22:
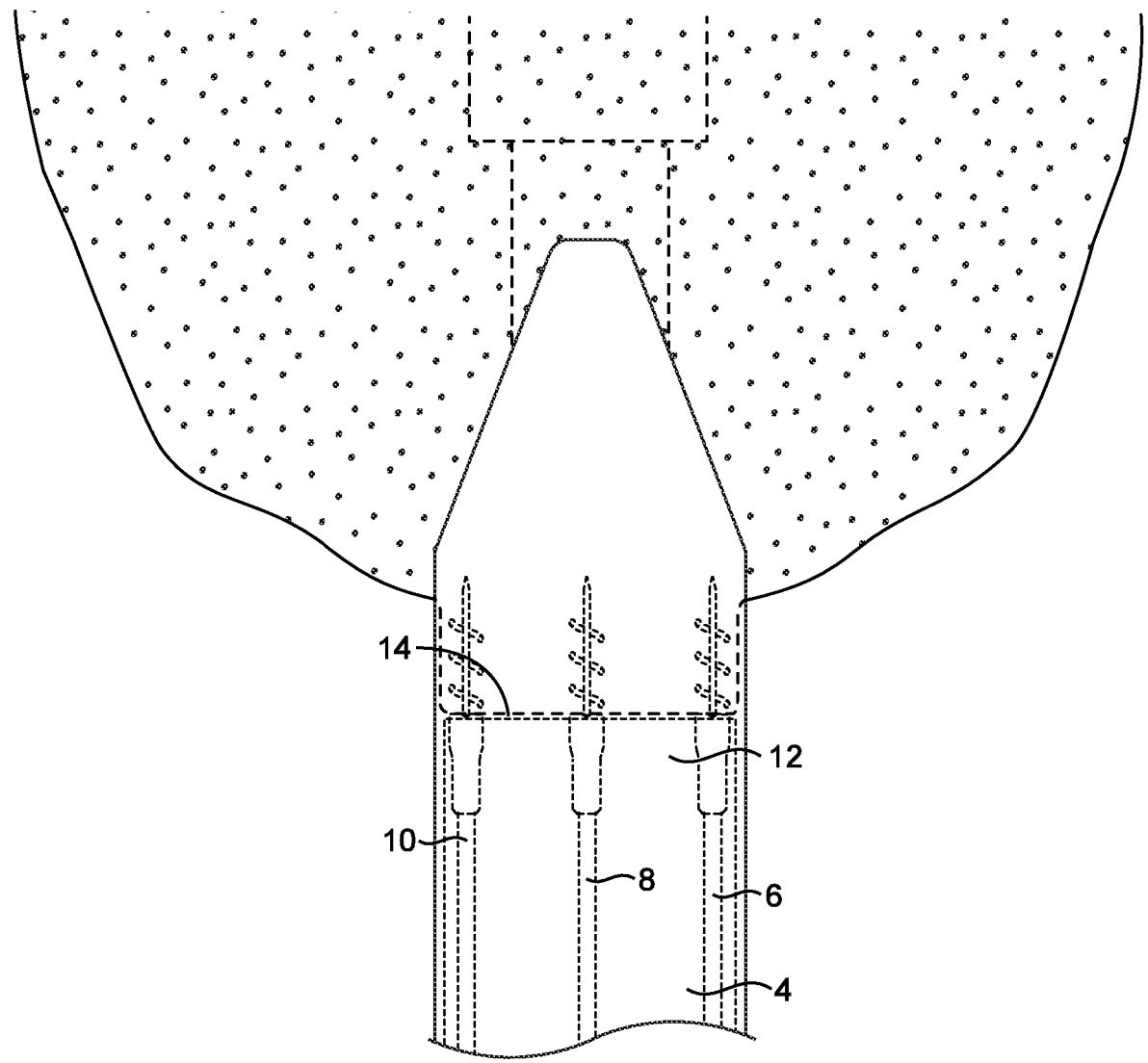
FIG. 22 shows three tissue displacing elements simultaneously displaced into the tissue shaper using the common retractor.
Figure 23:
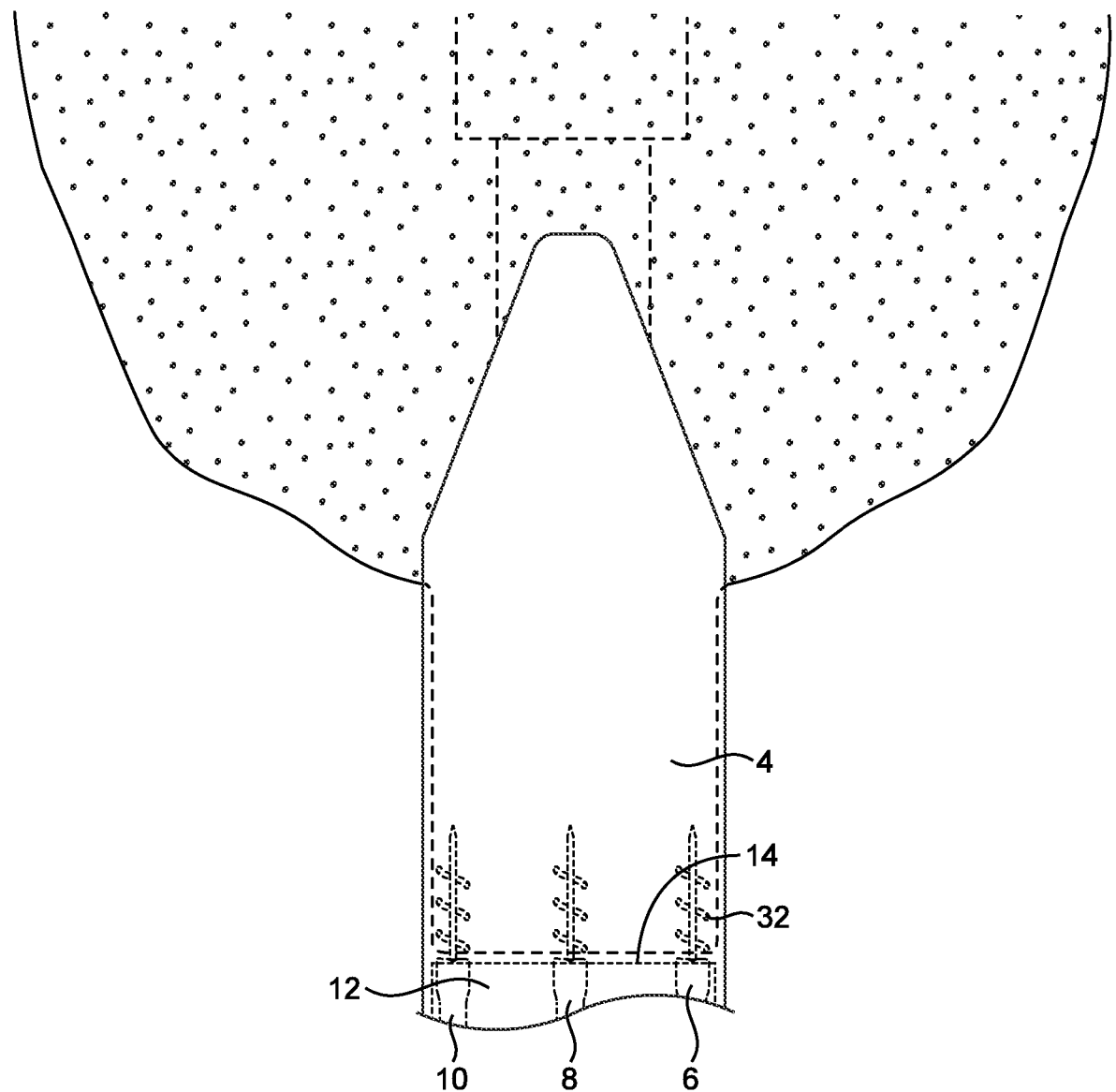
FIG. 23 shows all three tissue displacing elements retracted further by the common retractor.

Once the user has engaged tissue with each of the tissue displacing elements 6, 8, 10 and displaced each of the tissue displacing elements 6, 8, 10 as desired, the user may simultaneously displace all of the tissue displacing elements 6, 8, 10 using the common retractor 12 (see FIG. 21) to draw all three tissue displacing elements 6, 8, 10 into the tissue shaper 4 (see FIGS. 22 and 23). Suction may be applied to the orifices 72 in the platform 14 (FIG. 5) which may assist in drawing the tissue into the tissue shaper 4 as the common retractor 12 is moved into the tissue shaper 4. Of course, the tissue displacing elements 6, 8, 10 may be used to individually draw tissue into the tissue shaper 4, rather than using the common retractor 12 to simultaneously move all tissue displacing elements 6, 8, 10, without departing from the present invention. This may be accomplished by simply positioning the platform 14 in the cavity or even distal to the shaper 4 so that tissue is drawn into the tissue shaper 4 by the tissue displacing elements 6, 8, 10 alone (see FIG. 31).

Referring again to FIG. 8, the fold of tissue is shown contained within the tissue shaper 4. The fold of tissue forms the intersection between the esophageal tract and the stomach and has an esophageal side 131 and a stomach side 133 although at least some of the tissue on the esophageal side 131 may be characterized as stomach tissue prior to creation of the fold due to the disease state as described above. The tissue shaper 4 is sized to hold the fold of tissue and may be adapted to expand to a larger volume to accommodate the fold tissue due to the elastomeric portion 52 and the slits 60 (FIG. 4). Once the tissue is contained within the tissue shaper 4, the fold may be manipulated as now described or any other manner described herein.

The fold of tissue in the shaper 4 may be manipulated using the tissue shifting element 110 as shown in FIGS. 8-10. The needle 112 and/or needle 112A pierce one or both layers of the tissue fold and the wire 114 is then pulled proximally thereby moving the needles 112 downward to draw more tissue into the tissue shaper 4 and shift tissue downward within the shaper 4. The tissue shifting element 110 may also change a position of the intersection between the stomach and the esophageal tract to increase a length of the esophageal tract. When only one tissue layer is engaged as shown in FIG. 9, the tissue shifting element 110 displaces only the stomach side 133 of the fold while the esophageal side 131 is held stationary by the vacuum orifices 23 on the primary shaft 15 (see FIG. 1). The tissue may also be shifted within the tissue shaper 4 using the elements 6, 8, 10. In this manner, the tissue displacing elements 6, 8, 10 serve as tissue shifting elements in accordance with the present invention. For example, the tissue displacing elements 6, 8, 10 may be used to displace the tissue further into the cavity 50 or through the open distal end 65 of the tissue shaper 4 (see FIG. 31). The tissue displacing elements 6, 8, 10 may also be moved within the slots 44 to shift and displace tissue within the tissue shaper 4 in any manner described herein. The tissue displacing elements 6, 8, 10 may all be used to apply longitudinal displacement as well as a change in angular position relative to the longitudinal axis similar to use of the slots 44.

Figure 24:
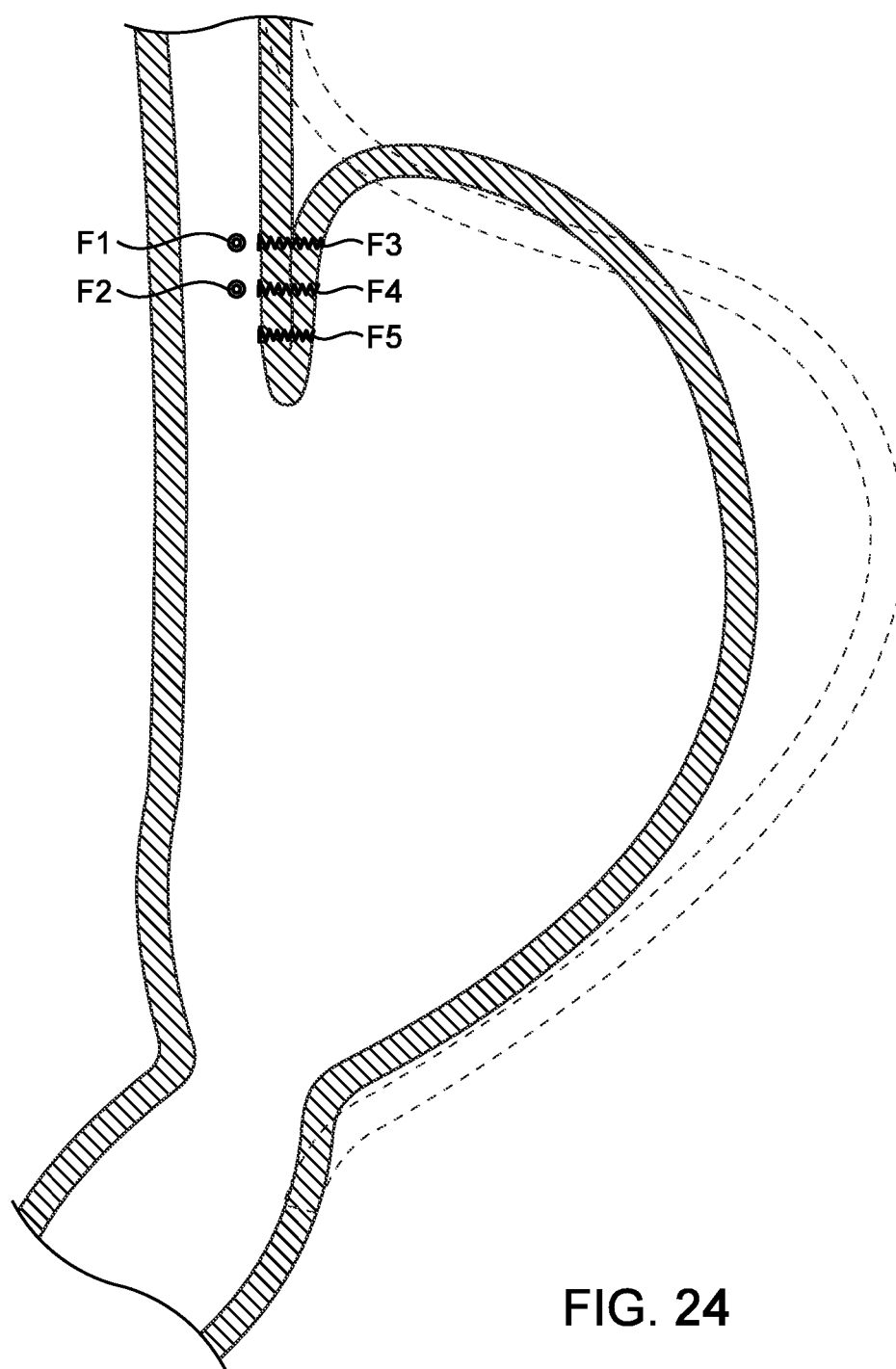
FIG. 24 shows fasteners applied to the stomach to create a tissue fold in accordance with the present invention.
Figure 25:
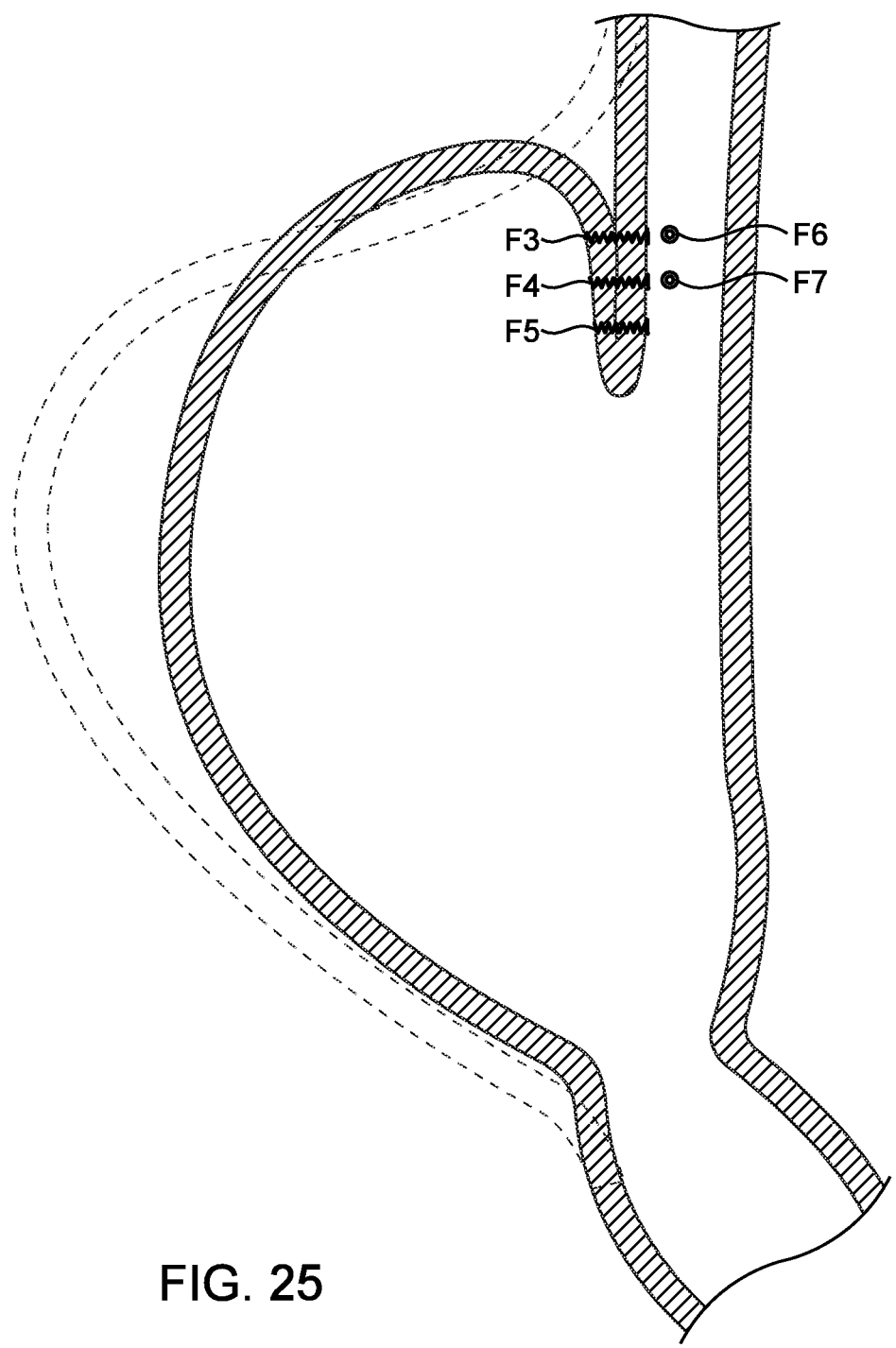
FIG. 25 show another view of the stomach where additional fasteners have been applied to the tissue fold.

Methods of fastening the fold of tissue together and additional methods of manipulating the tissue are now described. Each of the fastening methods may be used with any of the methods of manipulating tissue and forming the fold described herein. For the purpose of describing these methods, fasteners F1, F2, F3, F4, F5, F6, F7 are shown in FIGS. 24 and 25. Fasteners F1, F2 are longitudinally aligned at one end of the tissue fold (formed near the end 24 of the tissue shaper 4) and F6, F7 are at the other end of the tissue fold (and formed near the other end 26 of the tissue shaper 4). Fasteners F3-F5 are longitudinally aligned along a central portion of the fold of tissue. Of course, more or fewer fasteners may be applied and any of the fastener appliers described herein or any other suitable fastener applier may be used with or integrated with the device 2. As mentioned above, the clamping elements 61, 63 may be used to clamp the fold of tissue during application of fasteners and all methods described herein may include application of the clamping elements 61, 63 during each fastening step. The clamping elements 61, 63 may be released if further tissue displacing steps are carried out followed by application of the clamping elements 61, 63 before applying another fastener.

In one aspect of the present invention, the fastener applier 90 of FIG. 11 is used to deliver a plurality of fasteners, such as the staples 94, simultaneously. Once the fold of tissue is held in the desired shape, as shown in FIG. 23 for example, the fasteners F1, F2 may be applied simultaneously with the fastener applier 90 positioned at position P1 of FIG. 6. Fasteners F3, F4, F5 are applied at position P2 and fasteners F6, F7 are applied at position P3. Three separate fastening appliers 90 may be used to simultaneously apply each row of fasteners or one fastener applier 90 may be used to apply all of the fasteners in three separate steps using different preselected cartridges 92, 92A, 92B. When only one fastener applier 90 is used, the fastener cartridge 92 may be changed after each row of fasteners is applied. If the fastener applier has enough fasteners, the fastener applier 90 is simply rotated within the window 80 to the next appropriate location and the next set of fasteners 94 is applied. The fastener cartridge may be adapted to dispense the necessary amount of fasteners 94 at each application.

The fasteners 1-7 may be applied after all tissue manipulations have been completed. Alternatively, some of the fasteners F1-F7 may be applied and the tissue is further manipulated with the elements 6, 8, 10 or shifting element 110 followed by application of more fasteners F1-F7. This process may be repeated until all of the fasteners F1-F7 are applied while the user manipulates tissue between each fastening step as desired. The vacuum orifices 23 in the shaft 15 or the vacuum orifices 72 in the platform 14 may be used to further stabilize the fold of tissue between the fastening steps. The tissue shaper 4 itself may also help to firmly hold the fold of tissue (particularly if the elastomeric portion 52 is used) yet still permits shifting of tissue within the tissue shaper 4 and still permits tissue to be drawn into the tissue shaper 4. Various methods of manipulating tissue with the device 2 may include holding selected parts of the tissue fold stationary while tissue is manipulated with another part of the device 2. To this end, the vacuum orifices 23 in the shaft 15, the vacuum orifices 72 in the common retractor 23, the tissue displacing elements 6, 8, 10 and even the tissue shifting elements 110 may be used to hold parts of the tissue stationary while other parts of the device 2 are used to further displace the tissue in any manner described herein.

Figure 26:
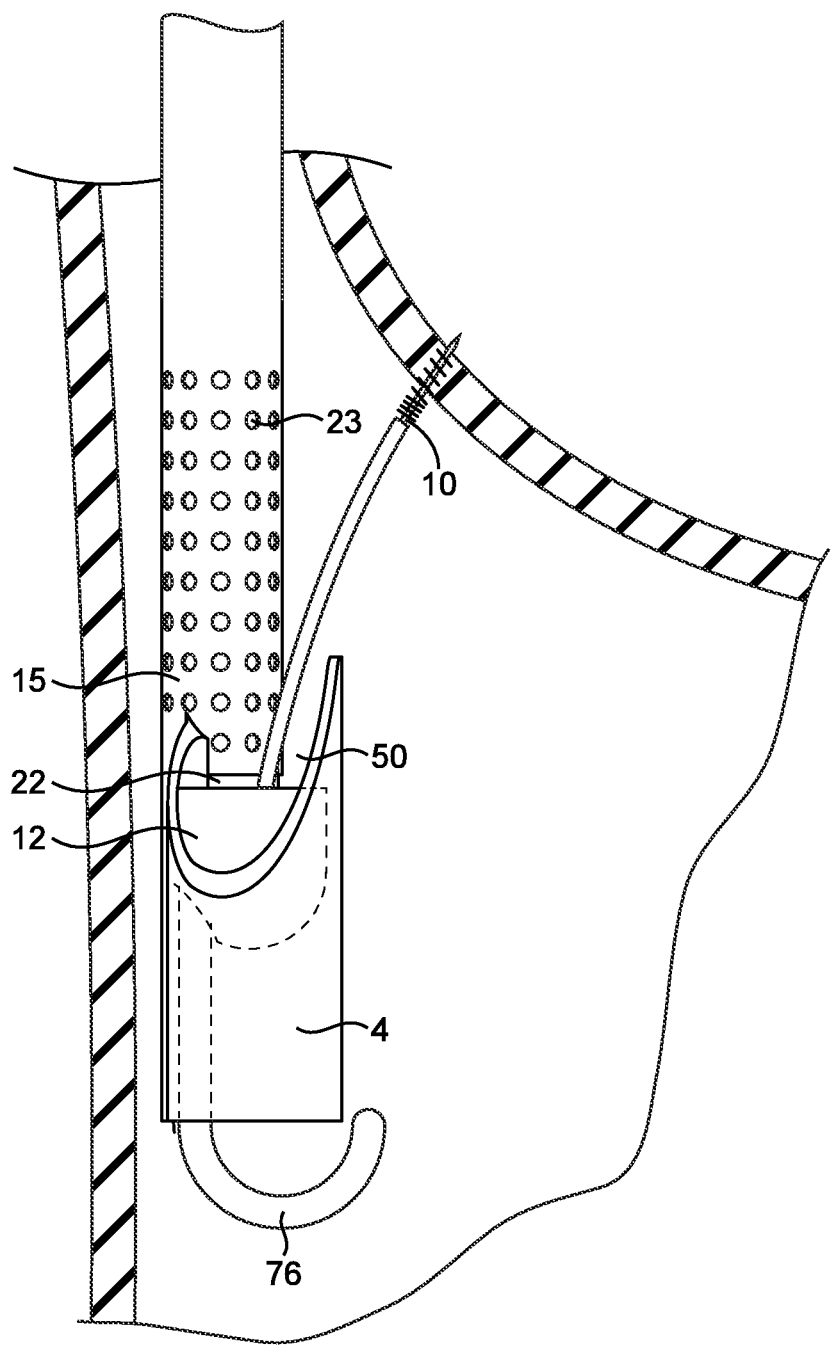
FIG. 26 shows the tissue displacing element engaged with stomach tissue.
Figure 27:
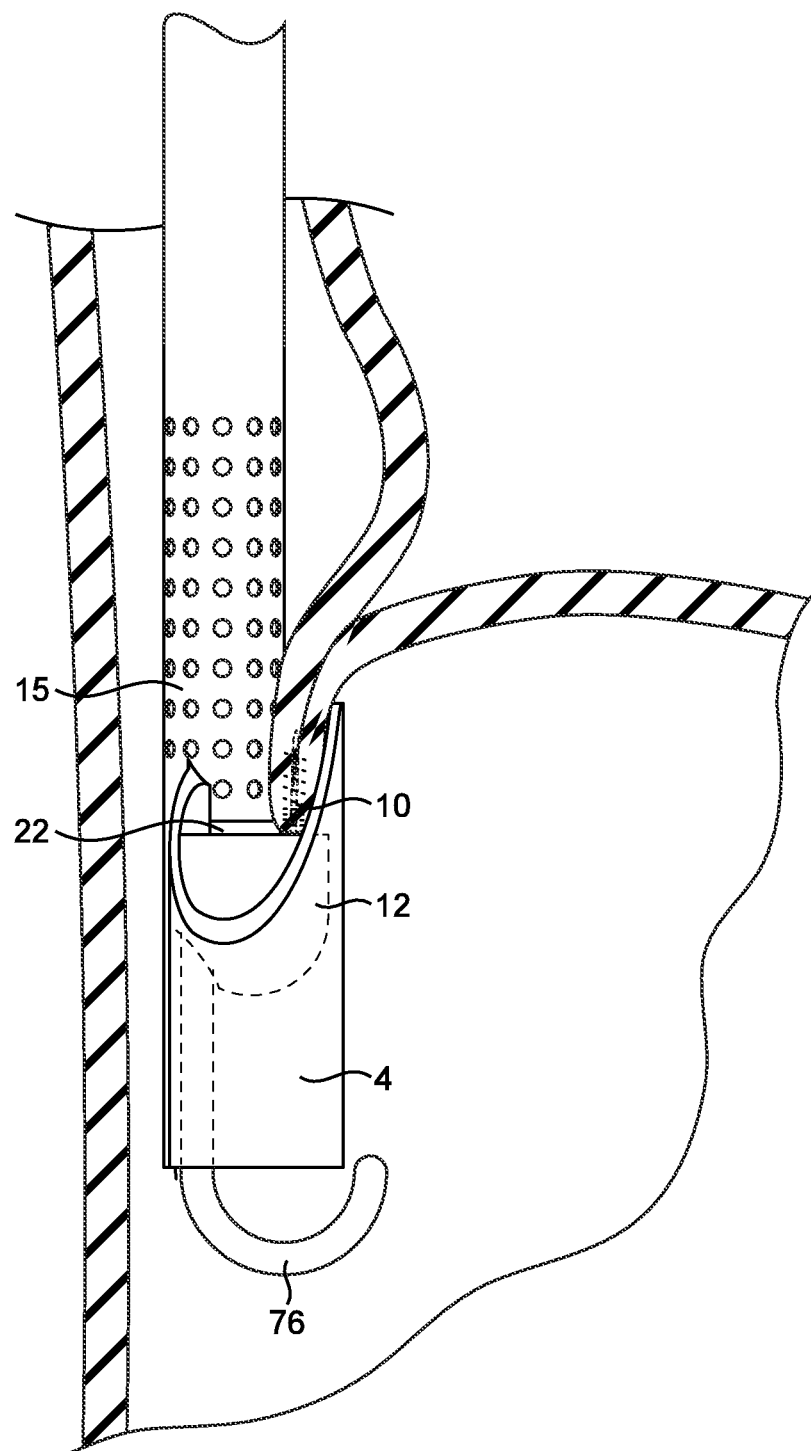
FIG. 27 shows the tissue displacing element retracted to displace tissue toward the tissue shaper.
Figure 28B:
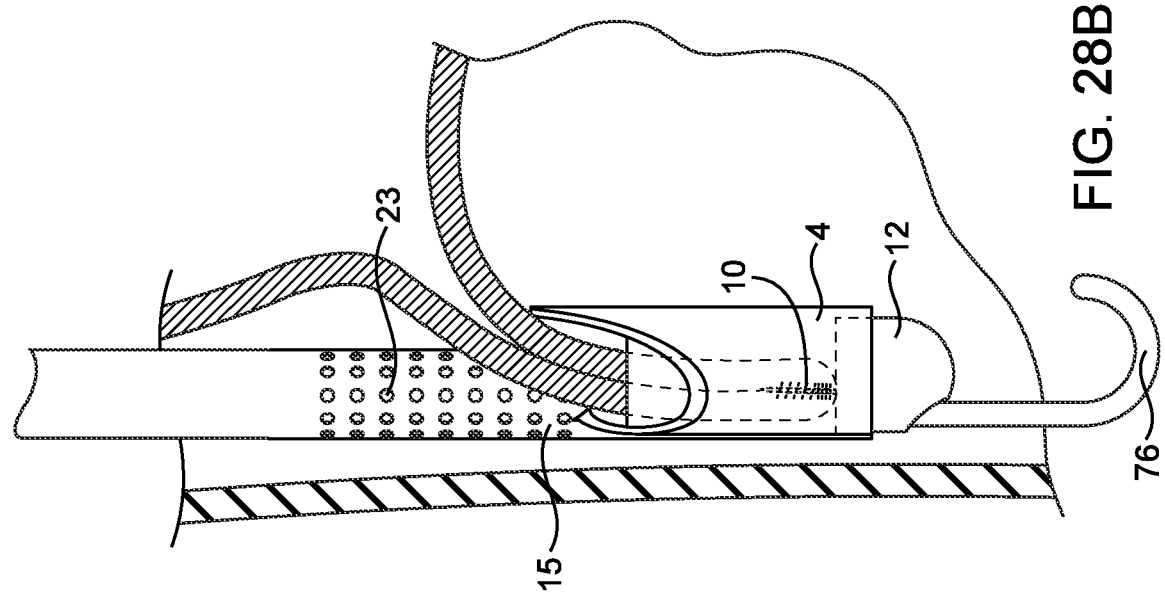
FIG. 28B shows the tissue displacing element of FIG. 28A moved into the tissue shaper.
Figure 28A:
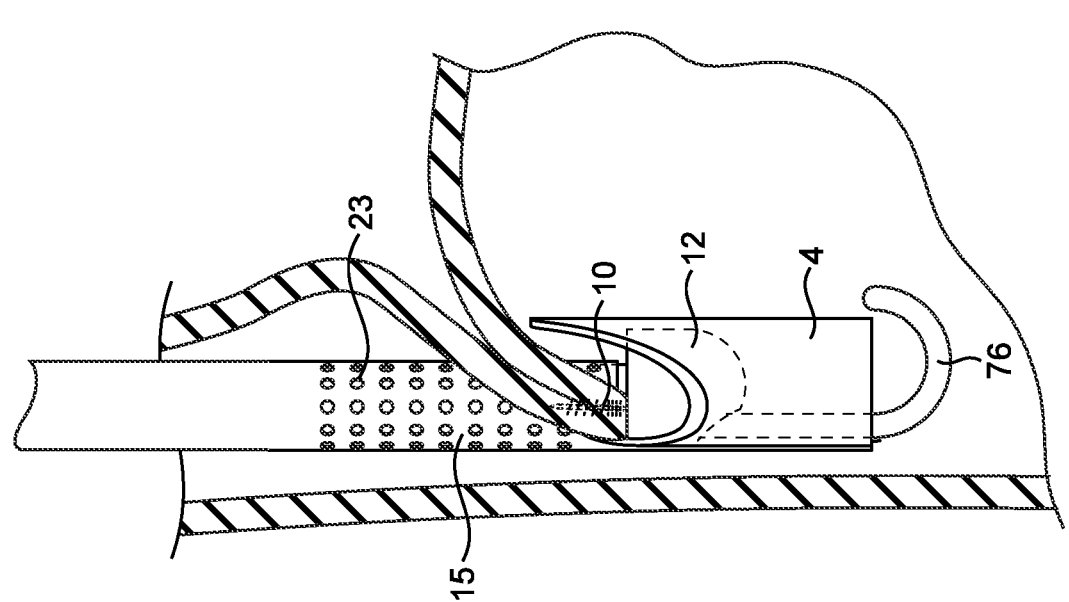
FIG. 28A shows the tissue displacing element moved within the slot to displace tissue toward an end of the tissue shaper.

In one example of a procedure having a number of fastening and tissue manipulation steps, fasteners 1, 2 and fasteners 6, 7 at the ends 24, 26 of the tissue shaper 4 are applied first followed by application of fasteners 3, 4, 5 along the central portion of the tissue shaper 4. In this manner, the tissue fold is created at the ends 24, 26 of the tissue shaper 4 first followed by formation of the central portion of the fold. Referring to FIGS. 26-28, the third tissue displacing elements 10 (and the first tissue displacing element 6 in similar fashion on the opposite side) extends outwardly to provide for longitudinal and an angular displacement upon retraction as described herein. The first and third tissue displacing elements 6, 10 may also be manipulated within the slots 44, such as toward the ends 24, 26 of the tissue shaper 4, as shown in FIGS. 27-28. In this manner, tissue has been drawn towards the ends 24, 26 of the tissue shaper 4. The tissue is the drawn into the shaper 4 by moving the first and third displacing elements in any manner described herein to the dotted line position of FIG. 28. The fasteners 1, 2 and 6, 7 may then be applied near the ends 24, 26 of the tissue shaper 4.

Figure 29:
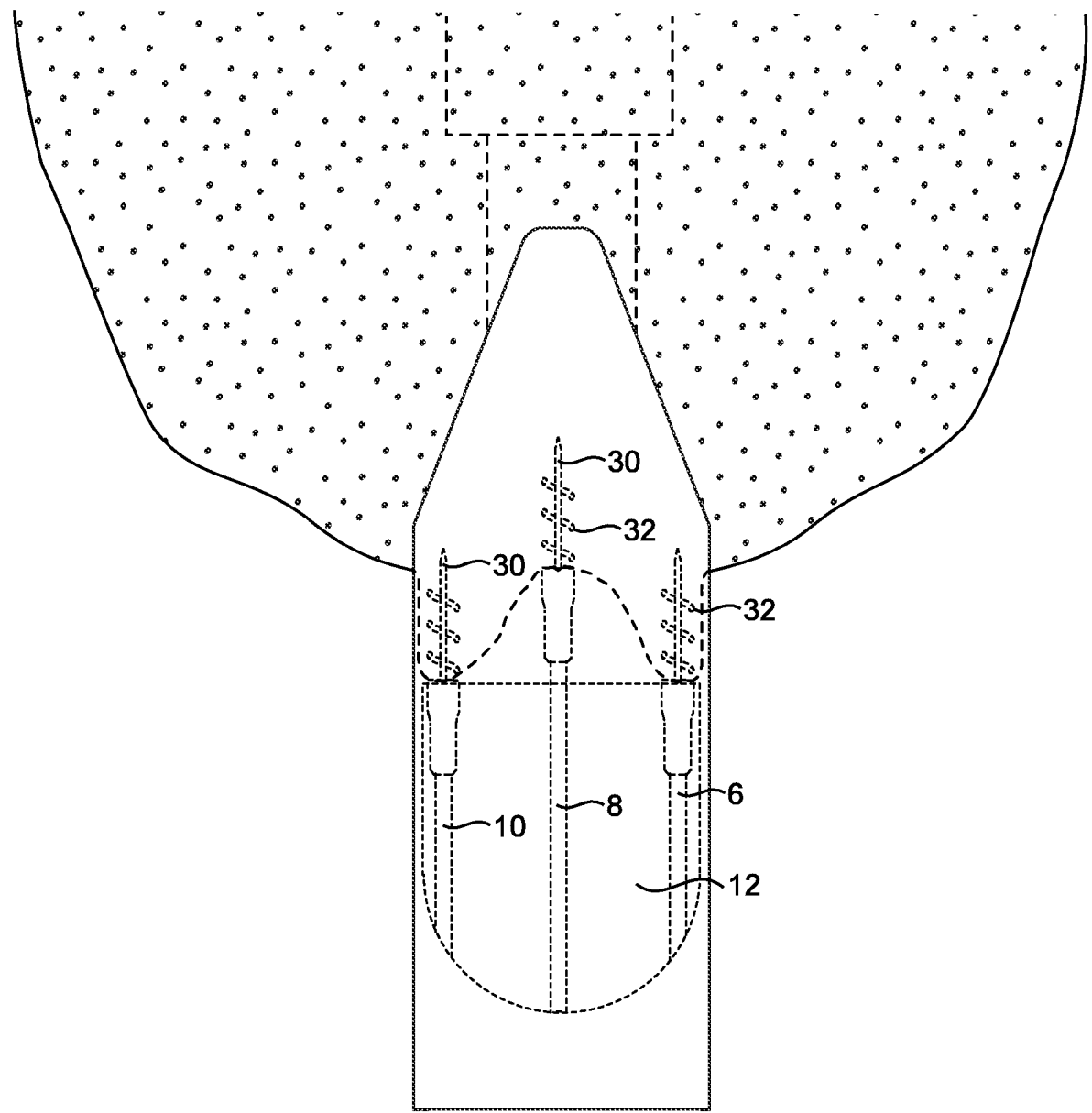
FIG. 29 shows the second tissue displacing element engaged with tissue after displacement in accordance with FIGS. 26, 27, 28A and 28B

The second tissue displacing element 8 may then be used to engage stomach tissue in the central portion of the tissue shaper 4 as shown in FIG. 29. The tissue is then pulled down by the second tissue displacing element 8 and fasteners 3, 4, 5 may then be applied simultaneously or may be applied one at a time between manipulations of the second tissue displacing element 8. When moving the first and third tissue displacing elements 6, 10, the lock 75 may be used to lock the first and third tissue displacing elements together 6, 10 and simultaneously move the first and third tissue displacing elements 6, 10.

Figure 30:
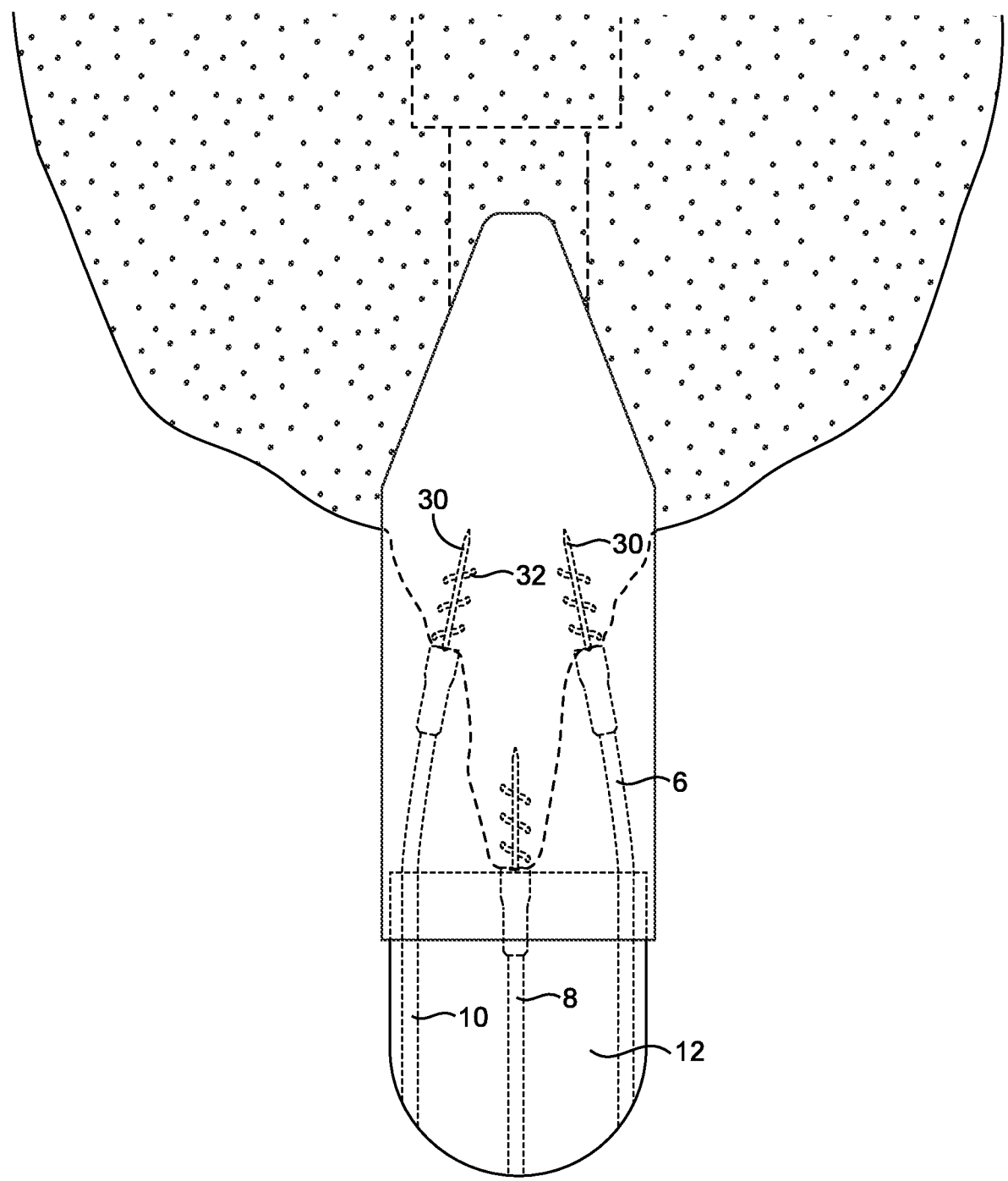
FIG. 30 shows the second tissue displacing element moving tissue with the first and third tissue displacing elements prior to displacement towards the ends of the shaper.

In another example of the present invention, fasteners 3, 4, 5 along the middle of the tissue shaper 4 (and along the middle of the tissue fold being created) are applied first and tissue is then manipulated prior to application of fasteners 1,2 and 6, 7 at the ends 24, 26 of the tissue shaper 4. Tissue may be manipulated between fastening steps by engaging tissue with the first and third tissue displacing elements 6, 10 and/or tissue shifting element 110 to tighten or loosen the fold, to lengthen the ends of the fold or to longitudinally stretch the fold as deemed necessary and as described herein. For example, the second tissue displacing element 8 is used to displace the central portion of the tissue fold downward and the first and third tissue displacing elements 6, 10 may then be engaged with tissue as shown in FIG. 30. The first and third tissue displacing elements 6, 10 are then retracted to pull tissue downward and also to move tissue towards the ends of the tissue shaper 4. To this end, the tissue displacing elements 6, 10 may impart displacements in any manner described herein. For example, the first and third tissue displacing elements 6, 10 may pull tissue towards the ends 24, 26 of the mold followed by displacement within the slots 4 toward the ends 24, 26 in a manner similar to the displacements shown in FIGS. 26-28 but in the opposite direction. In this manner, the tissue fold is created from the central portion towards the ends 24, 26 of the tissue shaper 4.

In yet another method of applying the fasteners F1-F7, the fastener applier may be held in a substantially stationary position and the tissue is manipulated after each fastener application. Referring again to FIGS. 22 and 23, an example of such a method is shown. Fastener F3 is applied in the position of FIG. 22. The tissue is then pulled further into the tissue shaper 4 using the tissue displacing elements 6, 8, 10 (or the common retractor to displace all three tissue displacing elements 6, 8, 10 simultaneously) and fastener F4 is then applied without moving the fastener applier from the position in which fastener F3 was applied. In this manner, the fastener applier may stay in a single, stationary position for several fastening steps while the tissue is manipulated between fastening steps. Fastener F5 may then be applied after further displacement of tissue to complete a row of fasteners near the central plane. Rather than completing the row of fasteners, the user may rotate the fastener applier to apply fasteners F1 and/or F6.

Figure 31:
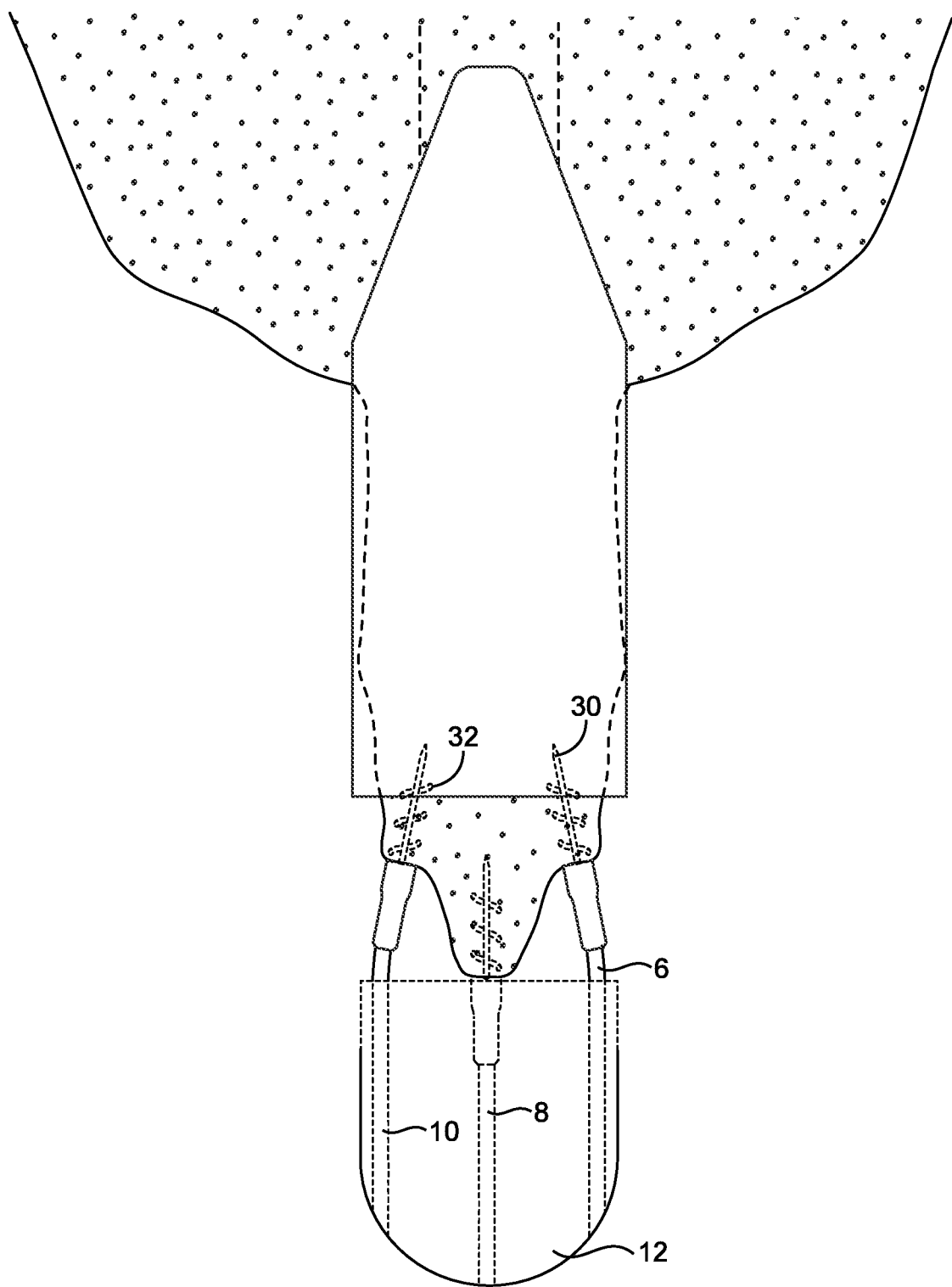
FIG. 31 shows tissue extending through an open distal end of the shaper for manipulation by the tissue displacing elements.

Referring now to FIG. 31, the tissue may also be manipulated through the open end 65 of the tissue shaper 4 and all methods described above may be practiced in this manner. For example, the method of applying the fasteners F1-F7 just described may be useful when the fold of tissue extends through the open end 65 of the tissue shaper 4. The user may clearly see how the formation of the fold is progressing as each fastener F1-F7 is applied and the fold becomes exposed through the open end 65 of the tissue shaper 4. As such, all methods of manipulating and fastening tissue described herein shall be applicable to methods of gathering and fastening tissue which partially extends through the open end 65 of the tissue shaper 4.

Figure 35:
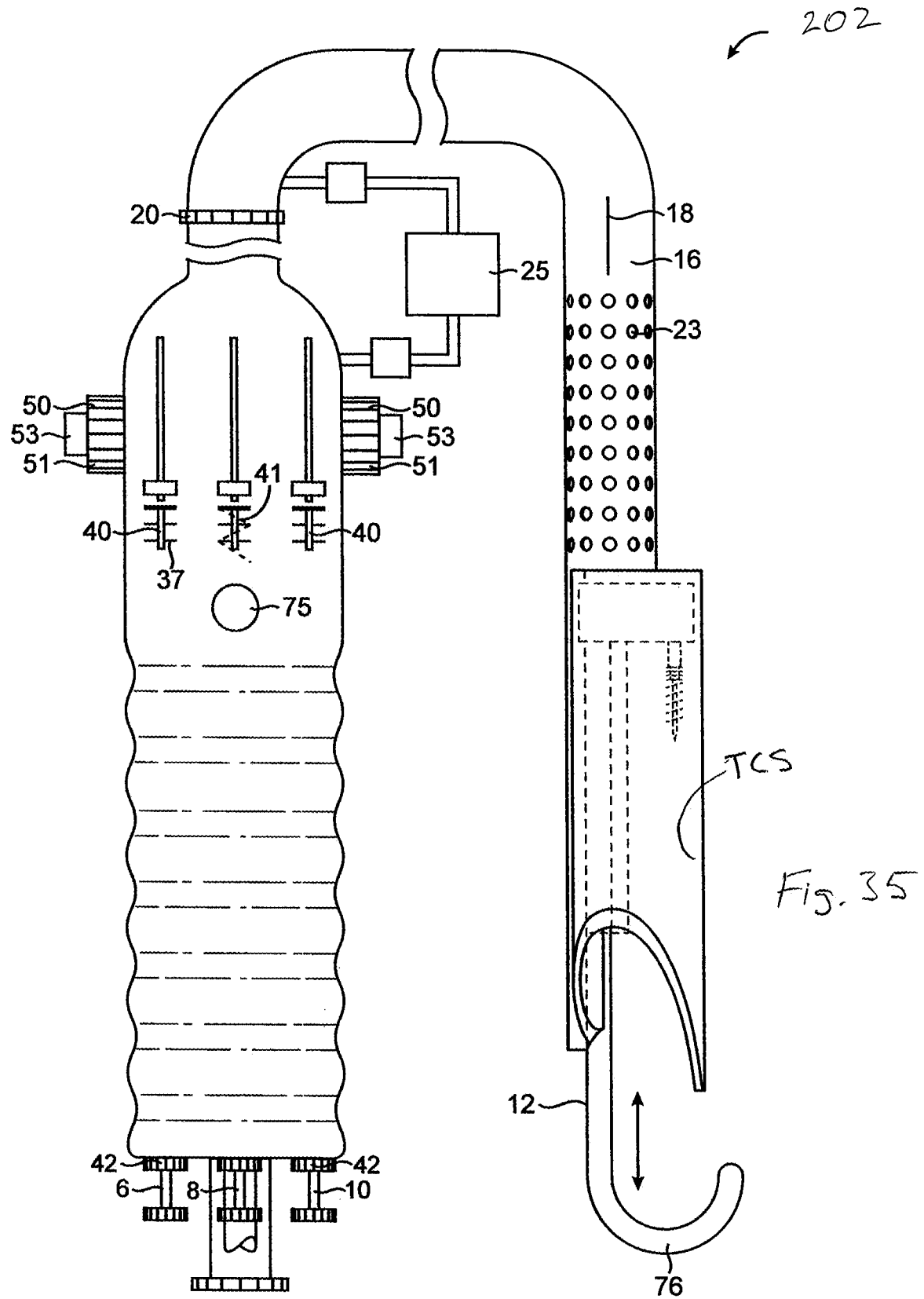
FIG. 35 shows another device for manipulating and fastening tissue.
Figure 36:
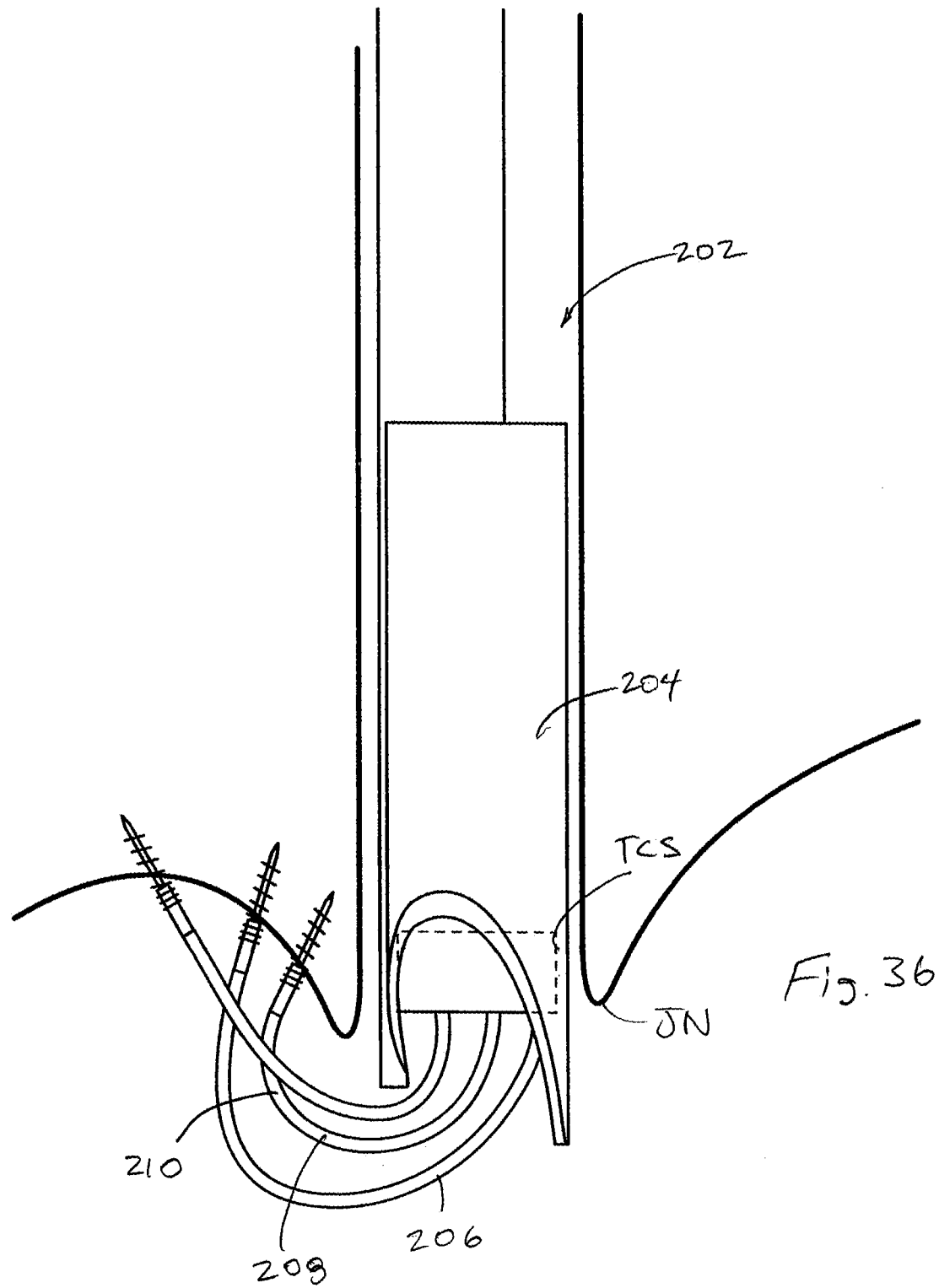
FIG. 36 shows the tissue shaper positioned in the esophageal tract.
Figure 37:
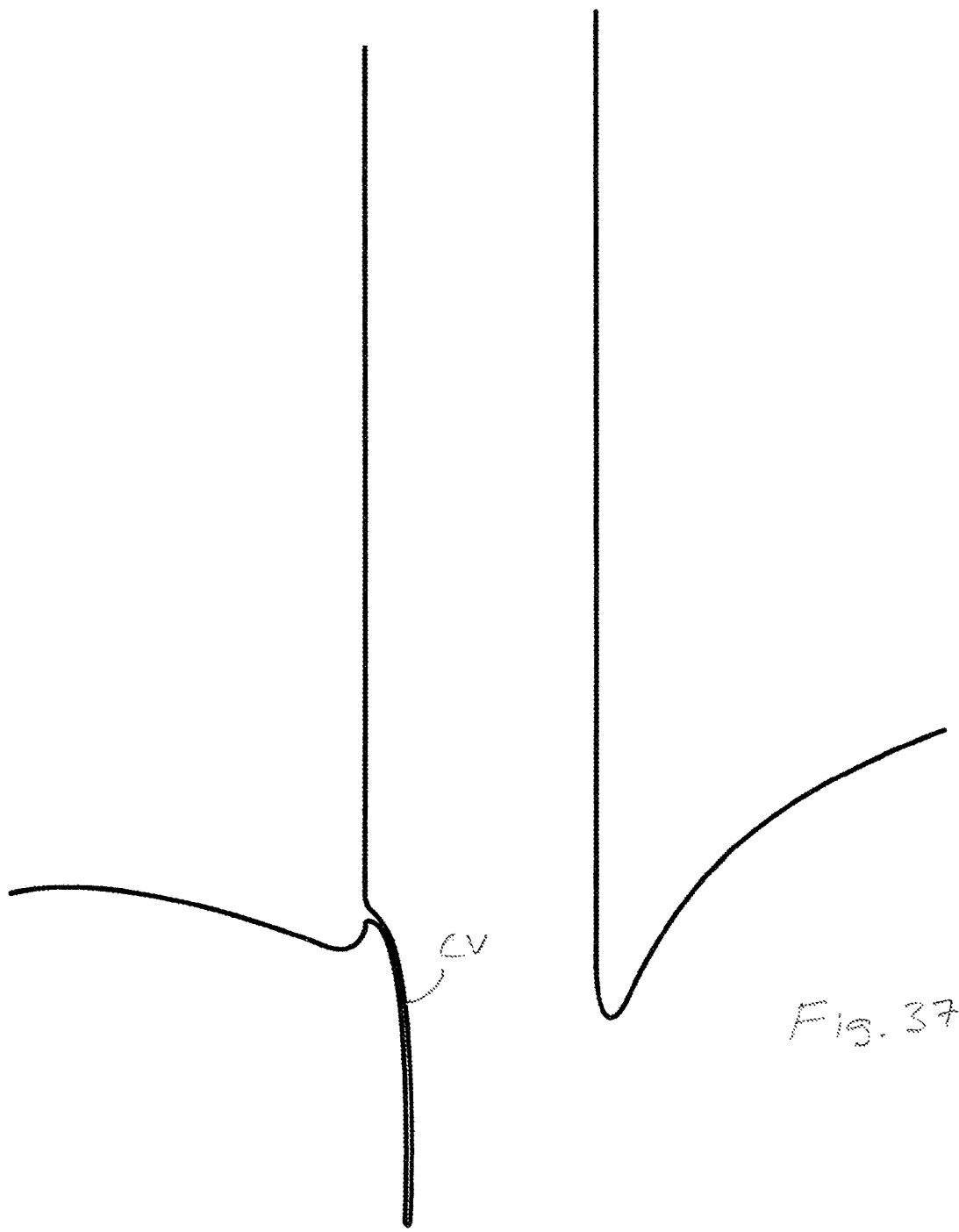
FIG. 37 shows a fold formed with the device of FIG. 35.

Referring to FIGS. 35-37, another device 202 is shown for displacing and fastening tissue wherein the same or similar reference numbers refer to the same or similar structure of FIGS. 1-34 with the difference being the orientation of a tissue shaper 204. All methods, uses and characteristics of the devices of FIG. 1-34 are applicable and incorporated here for device 202 with the designations proximal and distal being substituted for one another as necessary for the orientation of the tissue shaper 204. For example, the tissue displacing elements 206, 208, 210 of FIG. 35 may change radial orientation, displace tissue, and/or shift tissue within the tissue shaper 204 in any manner described with reference to FIGS. 1-34. Furthermore, the tissue shaper 204 of FIG. 35 (simplified for clarity) may be any of the tissue shapers described herein and all substitutions are hereby expressly incorporated. For example, the tissue shaper 4C of FIG. 34 may be used with the device 202 so that the first and second clamping elements 61B, 63B may be used to clamp tissue.

The tissue shaper 204 is oriented in the opposite direction from the tissue shapers of FIGS. 1-34 in that an open end 201 through which tissue is drawn is at a distal end rather than the proximal end of the tissue shaper 204. The tissue shaper 204 may be used anywhere in the stomach or esophagus but may be well suited to form tissue folds along the lesser curvature of the stomach at junction JN to the esophageal tract. Such a procedure may help treat GERD by bolstering, reinforcing, and/or tightening the area around the junction between the stomach and esophageal tract. Forming folds along this location may be conducted in association with procedures that create folds as described herein or the device itself may be used to form folds along the greater curvature side of the junction in the manner described herein. The tissue structures created along the lesser curvature side may be intended to interact with structures, such as a native or reconstructed flap, on the greater curvature side.

In one aspect, the tissue shaper 204 is positioned in the esophagus and stomach tissue is drawn into the tissue shaper with one or more of the tissue displacing elements 206, 208, 210 in any manner described in relation to FIGS. 1-34 which are incorporated here. For example, the tissue displacing elements 206, 208, 210 may be displaced stepwise, independently or simultaneously. After application of one or more fasteners, the resulting fold is released and falls back into the stomach so that part of fold opposes the flap on the greater curvature side. In one aspect of the invention, the fold is fastened on the lesser curvature side at least 1 cm, and may be at least 3 cm, above the junction between the esophageal tract and the stomach on the greater curvature side. Stated another way, the fold is formed within the esophagus so that when the fold is released the fold is positioned opposite a distal portion of the junction on the greater curvature side.

The tissue shaper 204 may be oriented so that a convex side CV of the fold is oriented radially inward (faces inward) relative to the esophagus. The convex shape may be naturally created by a convex shape TCS of the tissue shaper 204 when fasteners are applied as described above. Orienting the fold with the convex side TCS of the tissue shaper 204 facing inward may help displace the lesser curvature side closer to the greater curvature side thereby potentially improving the seal. Of course, the fold may be created in a conventional fashion with the convex side facing radially outward by rotating the device 180 degrees.

Referring to FIGS. 38-44, another device 300 for manipulating and fastening tissue is shown. The device 300 includes an elongate body 302 having a tissue grasper 304 with vacuum orifices 306 to grasp tissue along an outer surface 308 of the body 2. The tissue grasper 304 is described in greater detail below. A tissue shaper 308 has a shaft 309 that passes through a lumen 310 (see FIG. 43) in the tissue grasper 304. The shaft 309 of the tissue shaper 308 is aligned with the longitudinal axis LA of the tissue grasper and extends longitudinally from the tissue grasper so that the tissue grasper 304 and the tissue shaper 308 may be rotated relative to one another about a longitudinal axis LA (defined by the elongate body 302) and longitudinally translated as well. The modular design of the tissue grasper 304 and tissue shaper 308 allow any of the tissue shapers described herein to be used with any of the tissue graspers described herein and all combinations are expressly incorporated as can be appreciated by one of ordinary skill in the art.

The tissue shaper 308 has a mold 310 that is pivotally coupled to the shaft 309 at hinge 311. In this manner, the mold 310 also pivots relative to the elongate body 302 and the tissue grasper 304. Tissue is drawn into the mold 310 using a tissue displacing element 312 (not shown for clarity in other figures) having a helical coil 314 mounted to a wire 316 similar to those described above and incorporated here. The tissue shaper 308 forms a cavity 317 between the mold 310 and the shaft 309. The tissue shaper 308 may shape tissue in any other manner including a relatively static structure or a pair of jaws without departing from numerous aspects of the present invention. The mold 310 may pivot relative to the body 302 in any suitable manner such as those described in US Patent App. Nos. 2006/0116697, 2010/0222788, 2002/0082621, 2004/0138529 and 2011/0087198 which are incorporated hereby incorporated by reference. The mold 310, together with the tissue displacing element 312, the tissue grasper 304, and other mechanisms, work together to shape tissue into a desired shape in accordance with methods described below.

The tissue shaper 308 has a fastener guide 313 which may receive and guide a fastener 315 (see FIG. 47B), or other suitable fastener such as those described in U.S. Pat. No. 8,337,523 incorporated here by reference. The fastener 315, which may be used with all methods and tissue shapers of the present invention, is delivered on a stylet 321 and through a cannula 323 as shown in FIG. 47B. The fastener 315 has a first leg 327 mounted to the stylet 321. The first leg 327 has an elongate opening 325 and another elongate opening 333 for releasing the first leg 32. A second leg 329 trails the first leg 327 within the cannula 323. Of course, any other fastener may be used with the present invention without departing from the scope of the invention including staples, suture, a shaped implant and/or adhesive. Furthermore, the fasteners may be provided in a cassette or may be pre-loaded in the device.

The tissue shaper 308 also includes a first tissue shifting element 318 to shift tissue within the tissue shaper 308 on a radially inner side 320 (adjacent the elongate body) and a second tissue shifting element 322 to shift tissue on a radially outer side 324 (adjacent the pivoting mold). The first and second tissue shifting elements 318, 322 may be formed like a paddle 323 having integrally formed barbs 325 cut and formed from a plate of material but may also be a series of independent hooks, a helical coil or any other suitable structure. The second tissue shifting element 322 may include a space or slot therein (not shown) to receive the tissue displacing element 312 (see FIG. 38).

Figure 39:
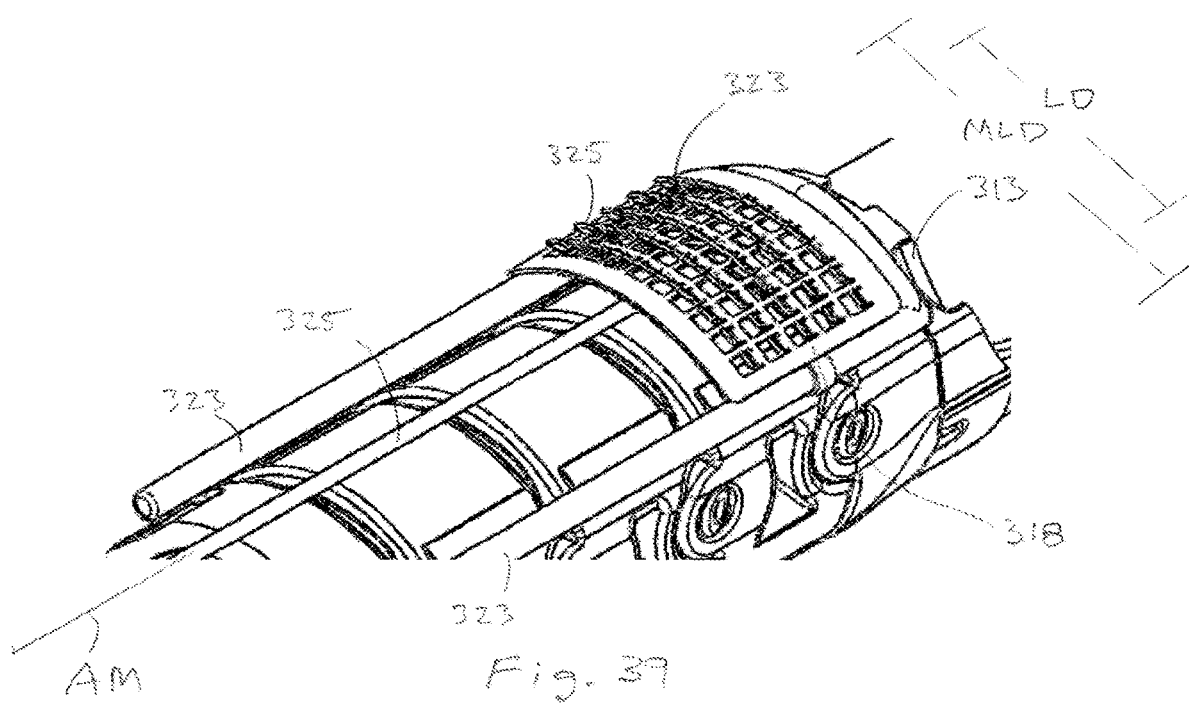
FIG. 39 shows a tissue shifting element.

The first and second tissue shifting elements 318, 322 are mounted on rails 323 that guide movement of the elements 318, 322. The rails 323 also bias the first and second tissue shifting elements 318, 322 to the position of FIG. 40. To this end, one or both of the rails 323 may be somewhat skewed so that the rails 323 diverge. Referring to FIG. 39, an actuating wire 325 moves the second tissue shifting element 322 to the position of FIG. 41. Doing so causes the rails 323 to spread apart somewhat. After shifting tissue, tension on the wire 325 is released so that the rails 323 are free to spread apart and move the first and second tissue shifting elements 318, 322 back to the position of FIG. 40.

Figure 41:
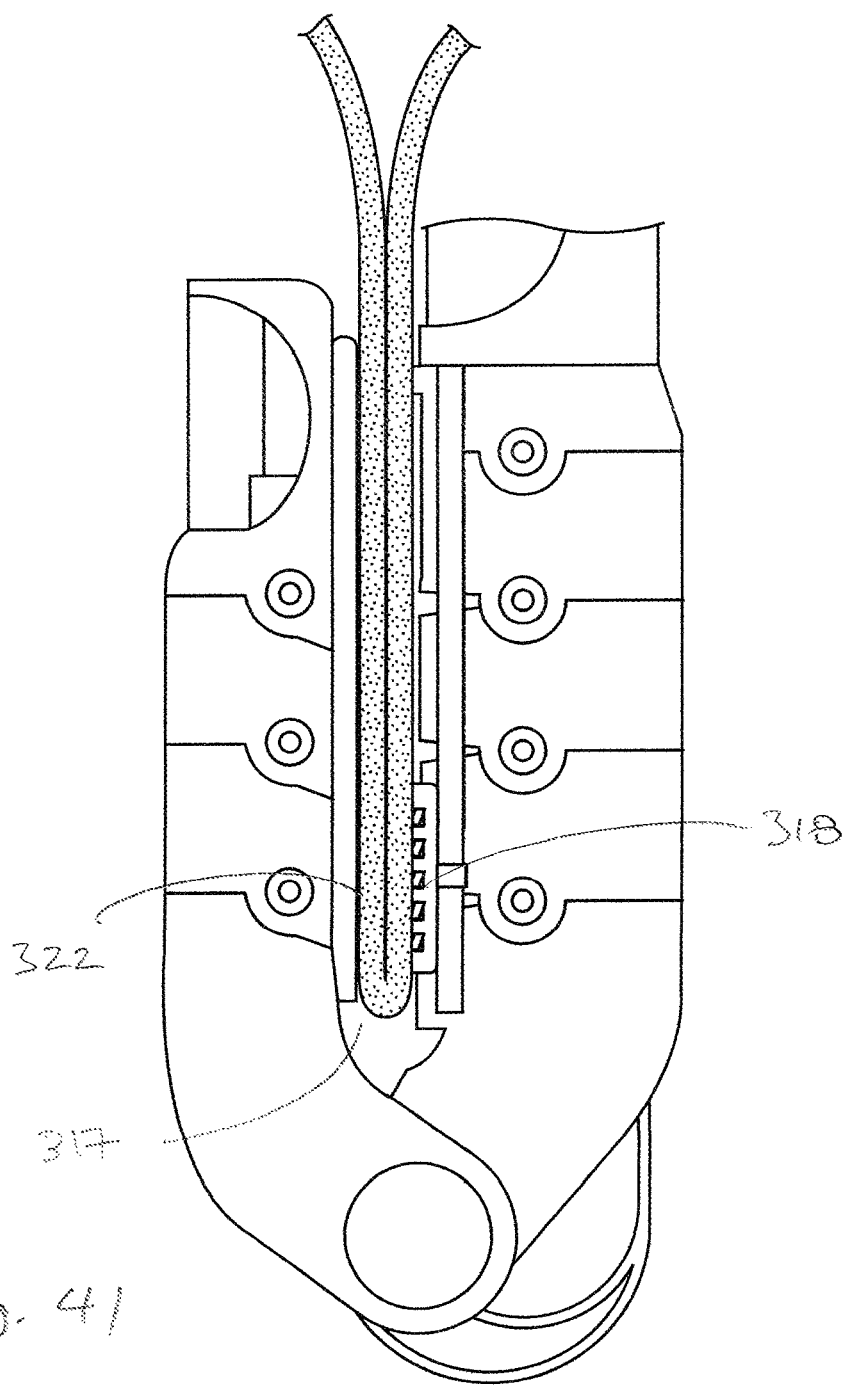
FIG. 41 shows the mold closed with the tissue shifting element moving more tissue into the tissue shaper.

The first and second tissue shifting elements 318, 322 may be independently operated or may be coordinated to displace tissue at the same time as shown in FIG. 41. The first and second tissue shifting elements are 318, 322 are relatively large compared to the tissue shaper 308 and may have a maximum lateral dimension LD which is at least 75% of a maximum lateral dimension of the mold MLD with the lateral dimension being measured in a direction transverse to the longitudinal axis LA and transverse to an axis of motion AM of the tissue shifting elements 318, 322.

Figure 40:
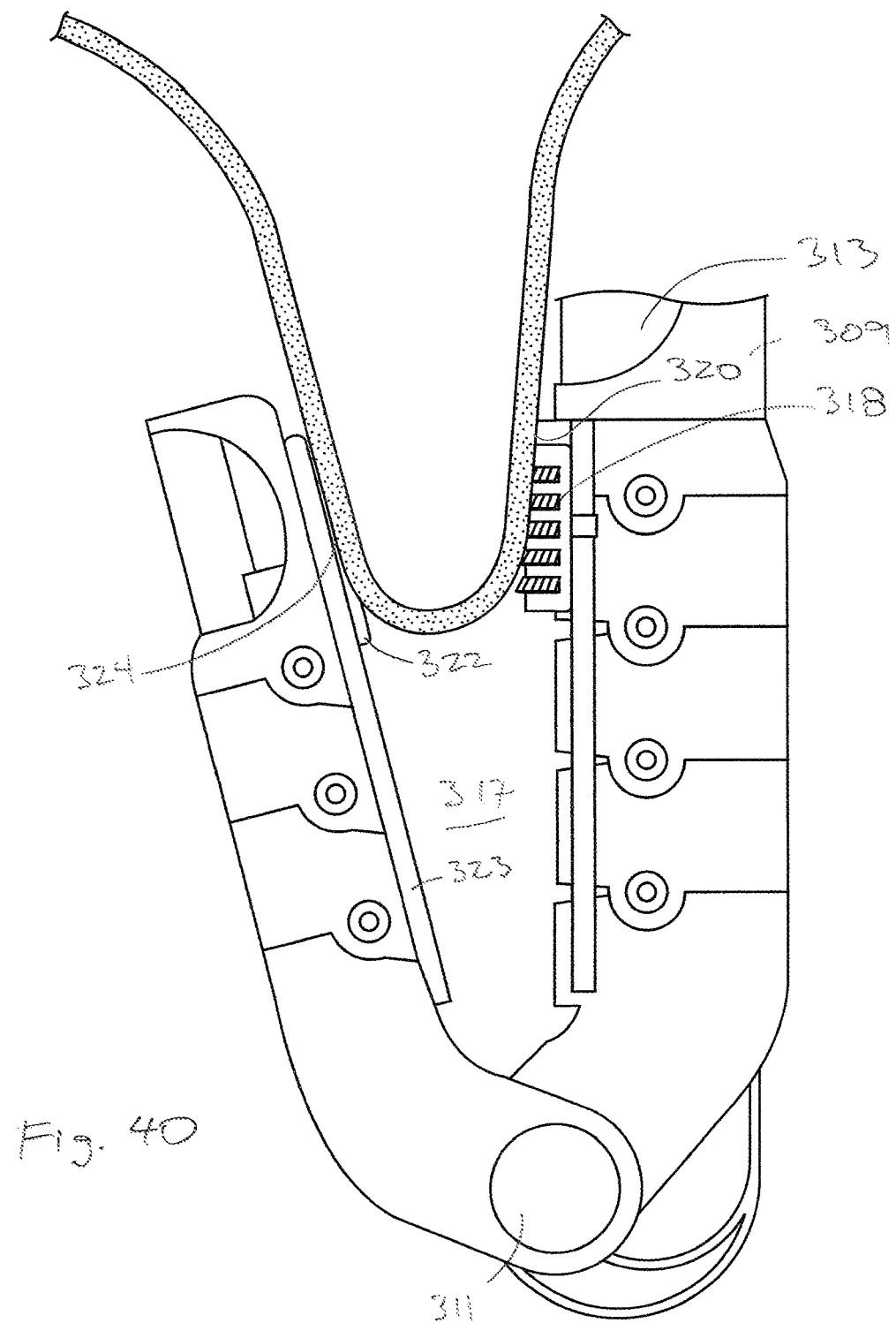
FIG. 40 shows a mold in a partially closed position.

When operating the tissue shifting elements 318, 322, the mold 310 is partially closed (compared to a fully closed position for fastening and manipulating tissue) so that the tissue layers are approximated and moderately compressed. The graphical depiction of FIG. 40 shows the layers separated for clarity and the jaws opened slightly larger than the partially closed condition. In this manner, the first and second tissue shifting elements 318, 322 are pressed into engagement with tissue while the tissue is held loosely enough to permit the tissue to slip further in the mold 310. The first and/or second tissue shifting elements 318, 322 are then moved to shift tissue further into the tissue shaper 304 thereby lengthening the fold.

The first and/or second tissue shifting elements 318, 322 may be used with all methods of the present invention to move tissue into the tissue shaper 308 prior to fastening even when not expressly mentioned with a particular method. The tissue grasper 304, or any of the other suitable tissue graspers described herein, may also be used to move tissue into the tissue shaper by moving the tissue grasper and tissue shaper toward one another (moving one or both). Similarly, in all methods of the present invention, even when not mentioned, any of the tissue graspers and tissue shapers may be moved together longitudinally to move more tissue into the mold and lengthen the fold. Finally, the terms "spread apart" or "moved together" as used herein refers to relative motion by moving one or both sides. When moving both sides, the sides may be moved independently (in either order or stepwise) or simultaneously. Use of the tissue grasper 304 and tissue shaper 308 is described below in connection with methods of the present invention.

Figure 42:
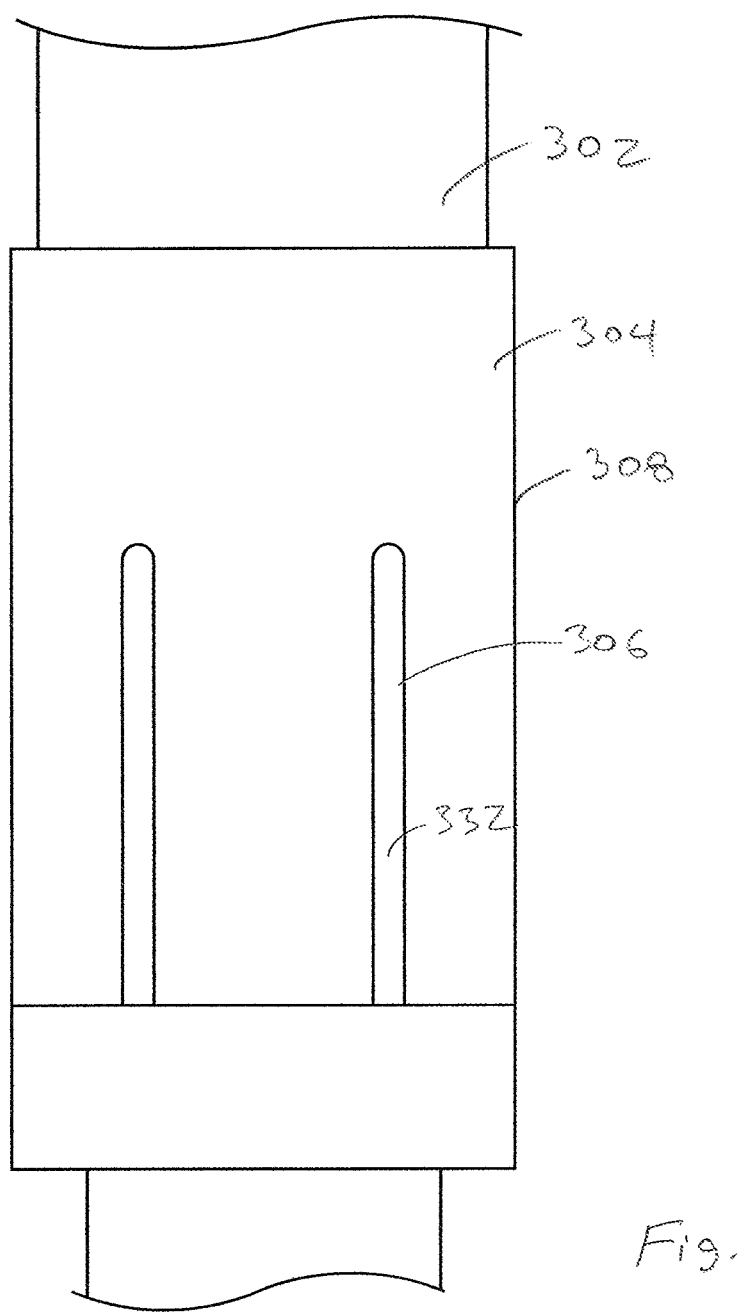
FIG. 42 shows a tissue grasper.
Figure 43:
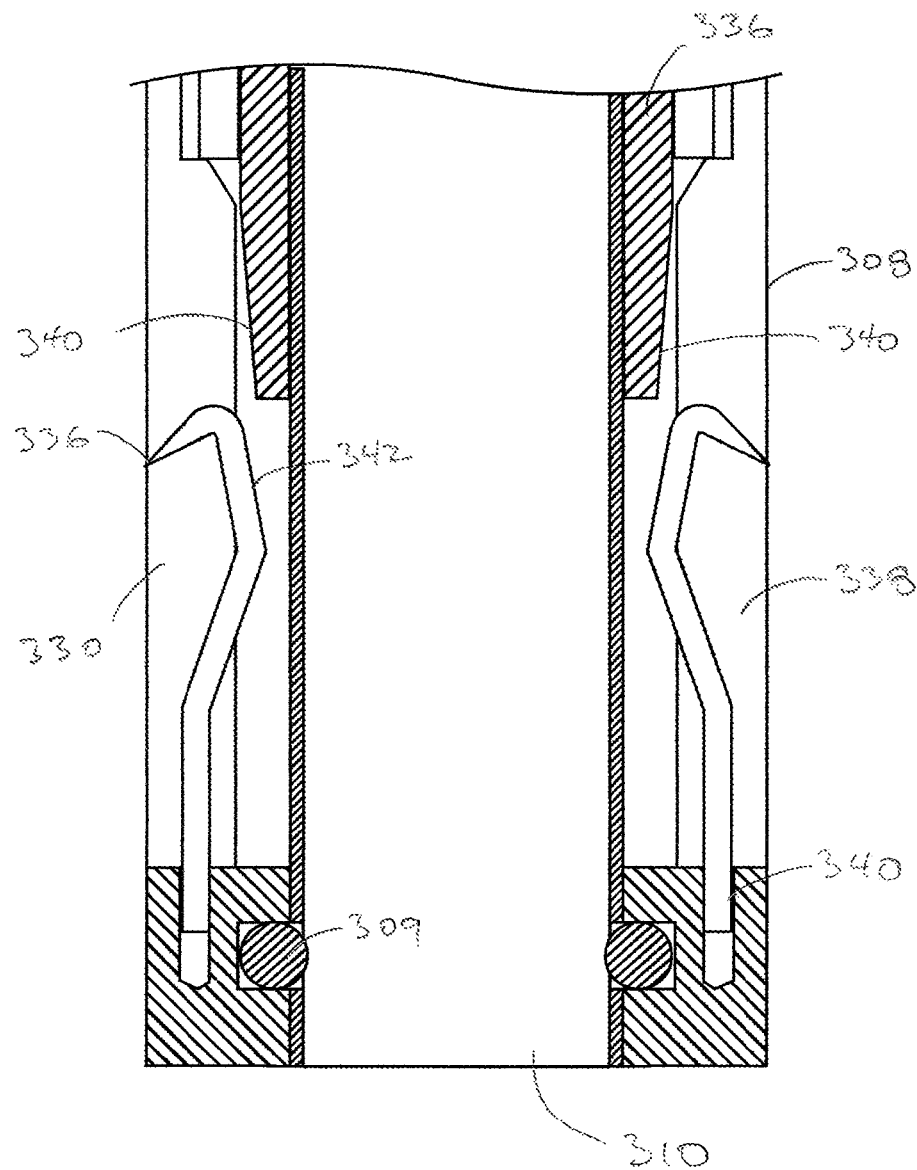
FIG. 43 is a cross-sectional view of the tissue grasper with tissue piercing elements in a stored position.
Figure 44:
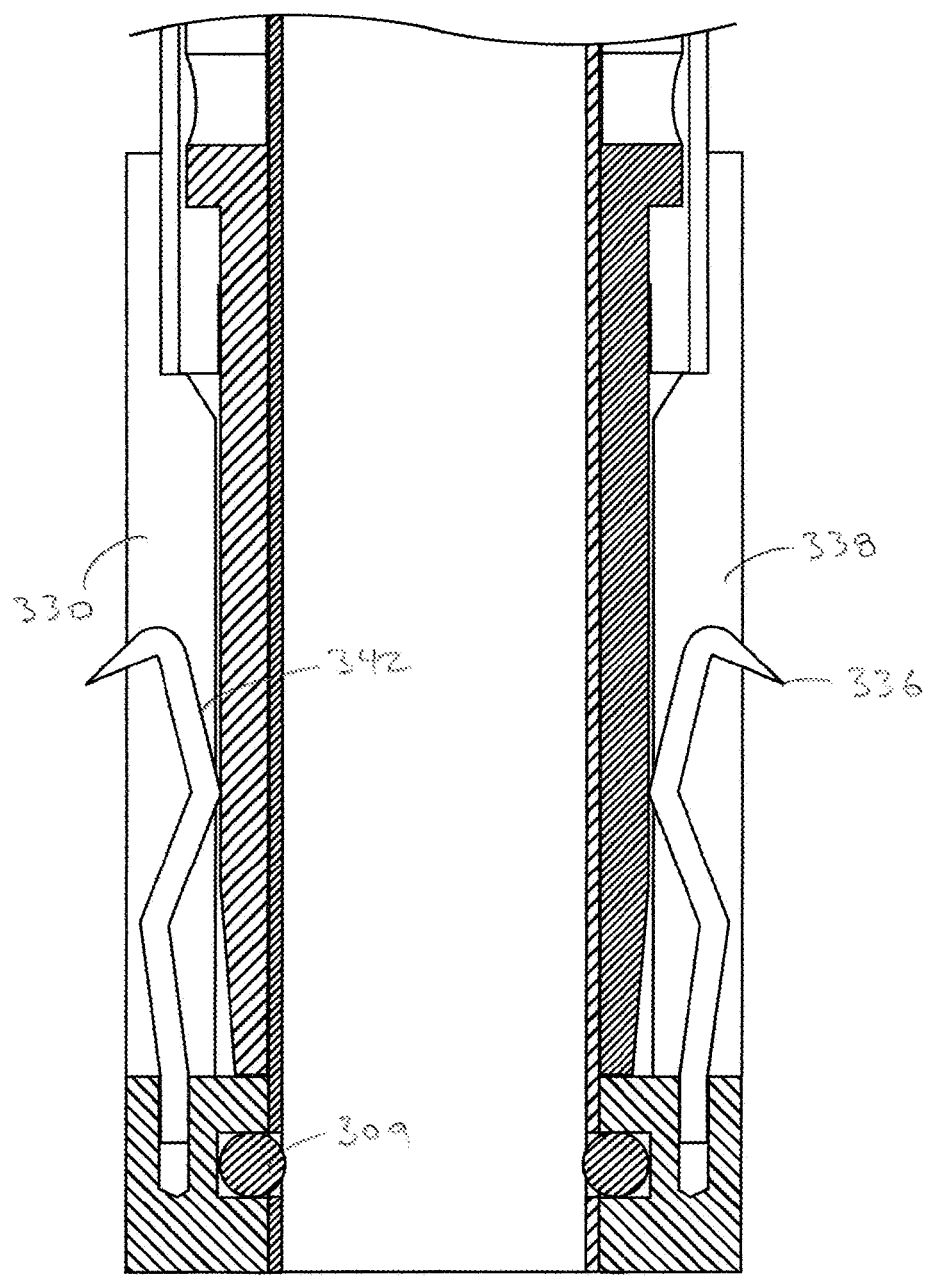
FIG. 44 is a cross-sectional view of the tissue grasper with tissue piercing elements in a working position.

Referring now to FIGS. 42-44, the tissue grasper 304 is now described. The vacuum orifices 306 on the outer surface 308 of the elongate body 302 adhere tissue to the body 2. The suction orifices 306 form a circumferential sealing surface 299 that forms a circumferential seal with tissue adjacent the elongate body 302 when suction is activated. A recess 330 extends from the vacuum orifice 306 in the outer surface 308. An o-ring 309 forms a seal around the tissue shaper 308 (removed from FIG. 43 for clarity). The vacuum orifices 306 may be round, oval, or any other suitable shape including an elongate slot 332 as shown. The shape may also be a compound shape such as a round opening superimposed on the slot 332.

Referring to FIGS. 43 and 44, a cross-sectional view of the slot 332 is shown. The tissue grasper 304 may have a tissue piercing element 334 in each recess 330 movable from the stored position of FIG. 43 to the working position of FIG. 44. The tissue piercing element 334 has a sharp tip 336 that preferably does not extend far out of the recess 330 when engaging tissue in the working position so that the piercing element 334 is less likely to harm tissue adjacent the target tissue. In a specific aspect, the tissue piercing element 334, and specifically the sharp tip 336, extends no more than 4 mm from the outer surface 308 of the body 302 in the working position and is positioned at or below the outer surface 308 in the stored position. The outer surface 308 of the body 302 is generally defined by the shape of the body 302, such as generally cylindrical and, thus, positioning the tissue piercing element 334 in the recess 330 shall be considered below the outer surface 308 even through the slot 332 is open.

The tissue piercing elements 334 are driven by an actuator 336 which may be a round collar 338 that simultaneously actuates all of the tissue piercing elements 334. The actuator 336 is advanced from the position of FIG. 43 to the position of FIG. 44 so that a first cam surface 340 on the collar 338 slides against a second cam surface 342 on the tissue piercing element 334 thereby moving the element 334 out of the recess to pierce tissue. The elongate slot 332 may help maintain alignment and orientation of the piercing element 334 as the piercing element 334 is deployed since the tissue piercing element slides against and is guided by sidewalls 338 of the slot 332. An advantage of providing the recess 330, such as the elongate slot 332, with the tissue piercing element 334 being advanced out of the recess 330 is that the use of suction prior to advancing the tissue piercing element 334 may help ensure that the tissue piercing element 334 engages a modest amount of tissue while limiting the extent that the piercing element 334 extends from the outer surface 308 of the body 302 to prevent damaging adjacent structures.

The tissue piercing element 334 may be generally directed in a distal direction so that the tissue piercing elements securely support distal displacement and rotation of the tissue grasper 304. Of course, any orientation may be used, such as radial or even extending generally proximally, without departing from the scope of the invention. The piercing element 334 has a fixed end 340, however, the piercing element 334 may also be pinned, captured by an elastic element or even captured without attachment, such as a block or pin movable within a groove. Furthermore, the piercing element 334 may be actuated in any suitable manner, such as pneumatic, a pull wire, or use of suction, without departing from the scope of the invention.

Figure 45:
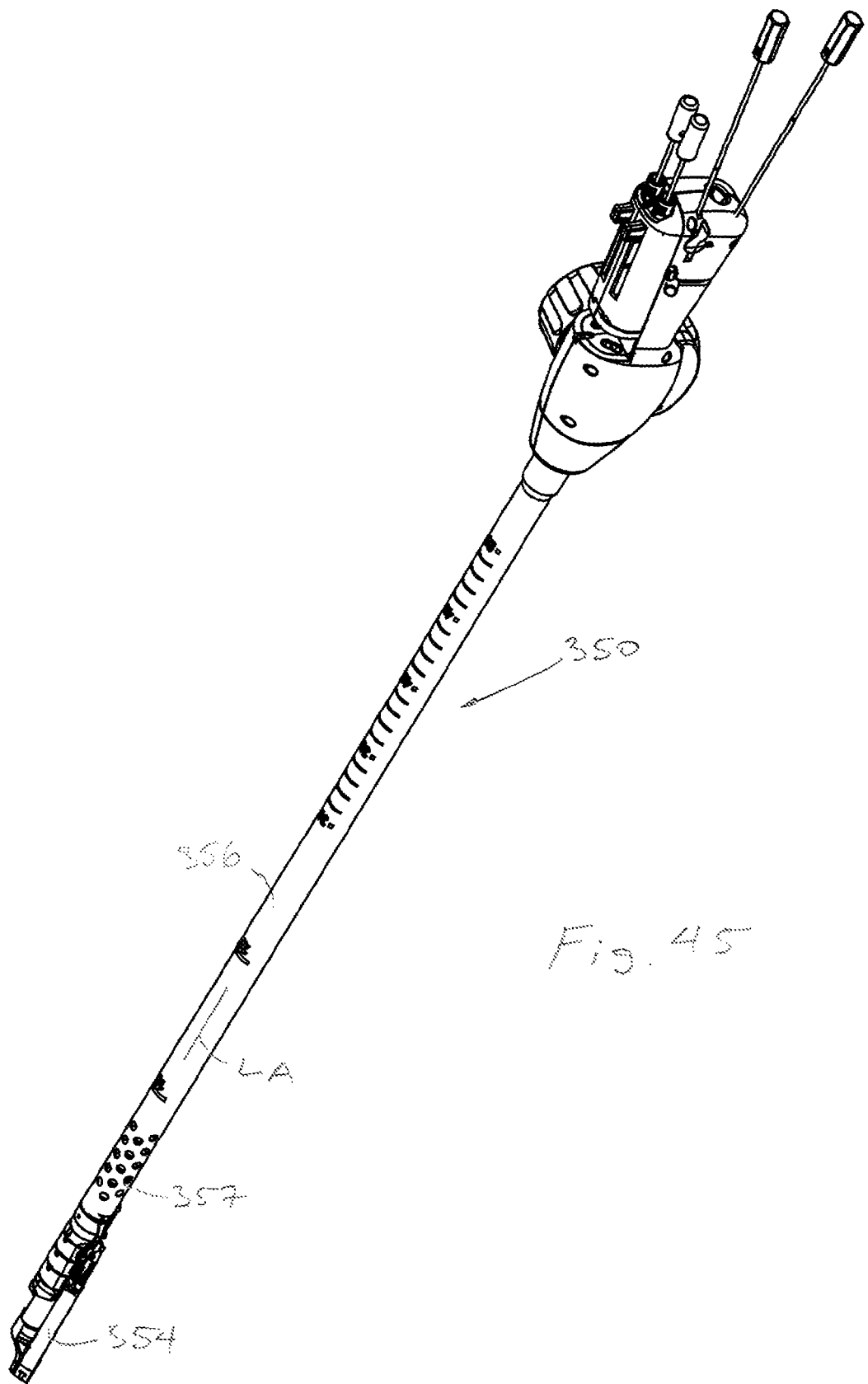
FIG. 45 shows another device for manipulating and fastening tissue.
Figure 46:
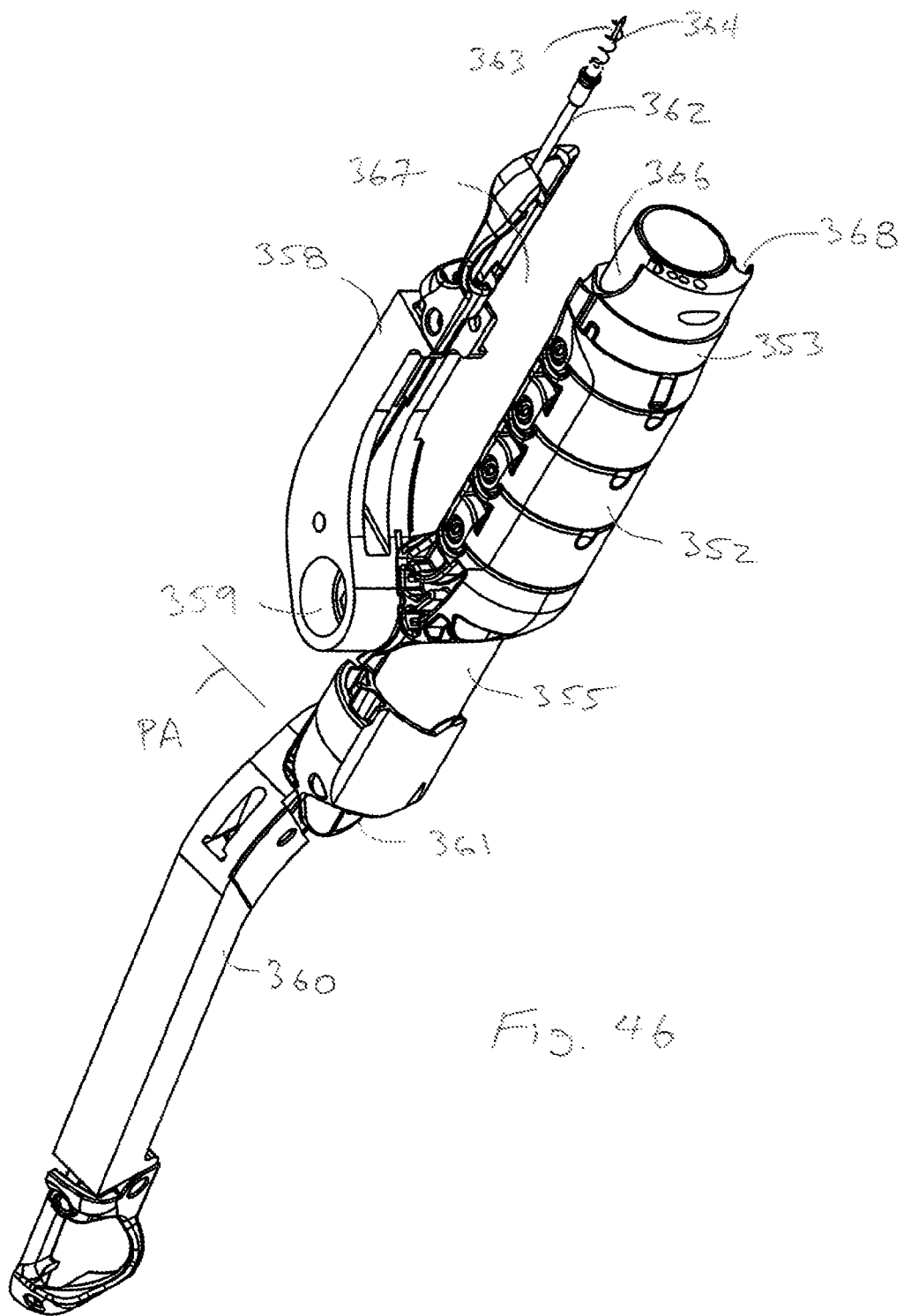
FIG. 46 shows a first tissue shaper closed and a second tissue shaper fully extended.
Figure 47:
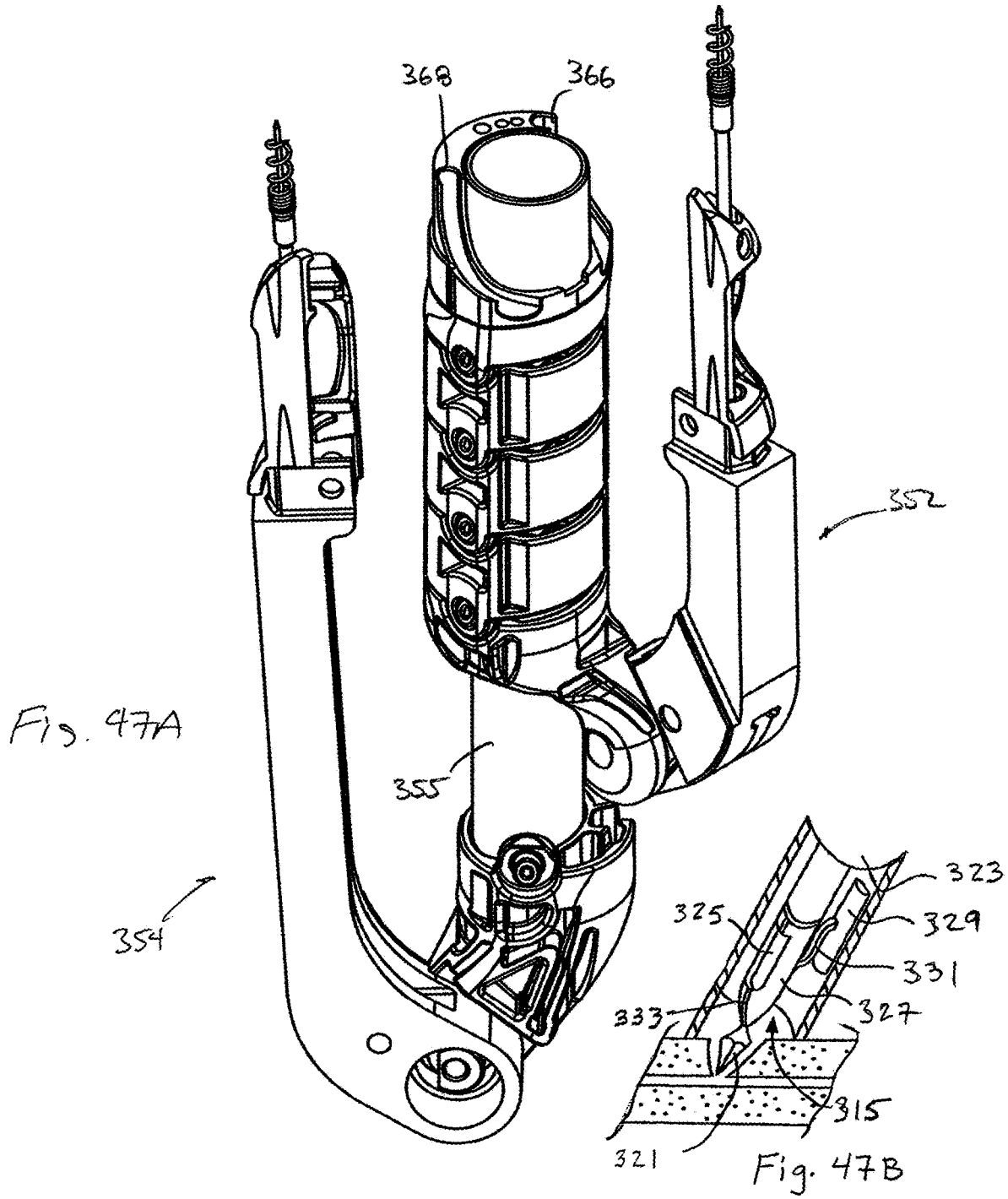
FIG. 47A shows the first and second tissue shapers in closed positions.
FIG. 47B shows a fastener.

Referring to FIGS. 45-47, another device 350 for grasping, displacing and fastening tissue is shown which includes a first tissue shaper 352 having a first shaft 353 and a second tissue shaper 354 having a second shaft 355 both extending through an elongate body 356 of a tissue grasper 357. The tissue grasper 357 may be any of the tissue graspers described herein for adhering tissue to the elongate body 356 as described below in connection with various methods of the present invention. The second shaft 355 extends through the first tissue shaper 352 so that the first and second tissue shapers 352, 354 are longitudinally translatable and rotatable relative to one another about a longitudinal axis LA. The longitudinal axis LA is generally defined by the shape of the elongate body 356 and it is understood that the elongate body 356 may be flexible and/or curved while still generally defining the longitudinal axis LA in all aspects of the present invention and for all embodiments described herein.

The first tissue shaper 352 has a first mold 358 pivotally coupled to the elongate body 356 and the second tissue shaper 354 has a second mold 360 which also pivots (and rotates) relative to the body 356. The first and second molds 358, 360 may be formed and actuated in any suitable manner as is known to those of ordinary skill in the art with each mold 358, 360 pivoting between the closed and fully extended positions of FIG. 47. Suitable mechanisms are well known in the art and include those described in the patent applications incorporated above. The first and second molds 358, 360 are pivotally coupled to the first and second shafts 353, 355 at distal ends 359, 361 of the shafts 353, 355. The first and second molds 358, 360 each pivot about an axis PV that is transverse to the longitudinal axis LA. The first tissue shaper 352 forms a first cavity 367 (into which stomach tissue is drawn using the first tissue displacing element 362) and the second tissue shaper 354 forms a second cavity 369 (into which stomach tissue is drawn using the second tissue displacing element 364). The first cavity 367 is formed between the first mold 358 and the first shaft 353 and the second cavity is formed between the second mold 360 and the first shaft 353.

The first tissue shaper 352 has a first tissue displacing element 362, such as a wire 363 and a helical coil 364, and the second tissue shaper 354 has a second tissue displacing element 364 each configured to draw tissue into the respective tissue shaper 352, 354. The tissue displacing elements 362, 364 may be initially guided by the molds 358, 360 and may be subsequently released as tissue is drawn into the respective tissue shaper 352, 354. The first tissue shaper 352 includes a first fastener guide 366 which guides fasteners, such as the fastener 315 of FIG. 47B, through tissue positioned in the first tissue shaper 362. A second fastener guide 368 is also coupled to the first tissue shaper 352 and delivers fasteners 315 to tissue held by the second tissue shaper 354. The second tissue shaper 354 aligns with the second fastener guide 368 at a fixed angular orientation relative to the first tissue shaper 352, such as 90 degrees, when fasteners 315 are applied to tissue in the second tissue shaper 354. Of course, the second tissue shaper 364 may also have a fastener lumen that rotates with the second tissue shaper 354 rather than the first tissue shaper 352. Alternatively, the second tissue shaper 354 may not include a fastener lumen or guide and all fasteners may be applied by the first tissue shaper 352 with the second tissue shaper 354 used to anchor, stretch and manipulate the tissue fold as described below. Use of the device 350 is described below in conjunction with methods of the present invention.

Figure 48:
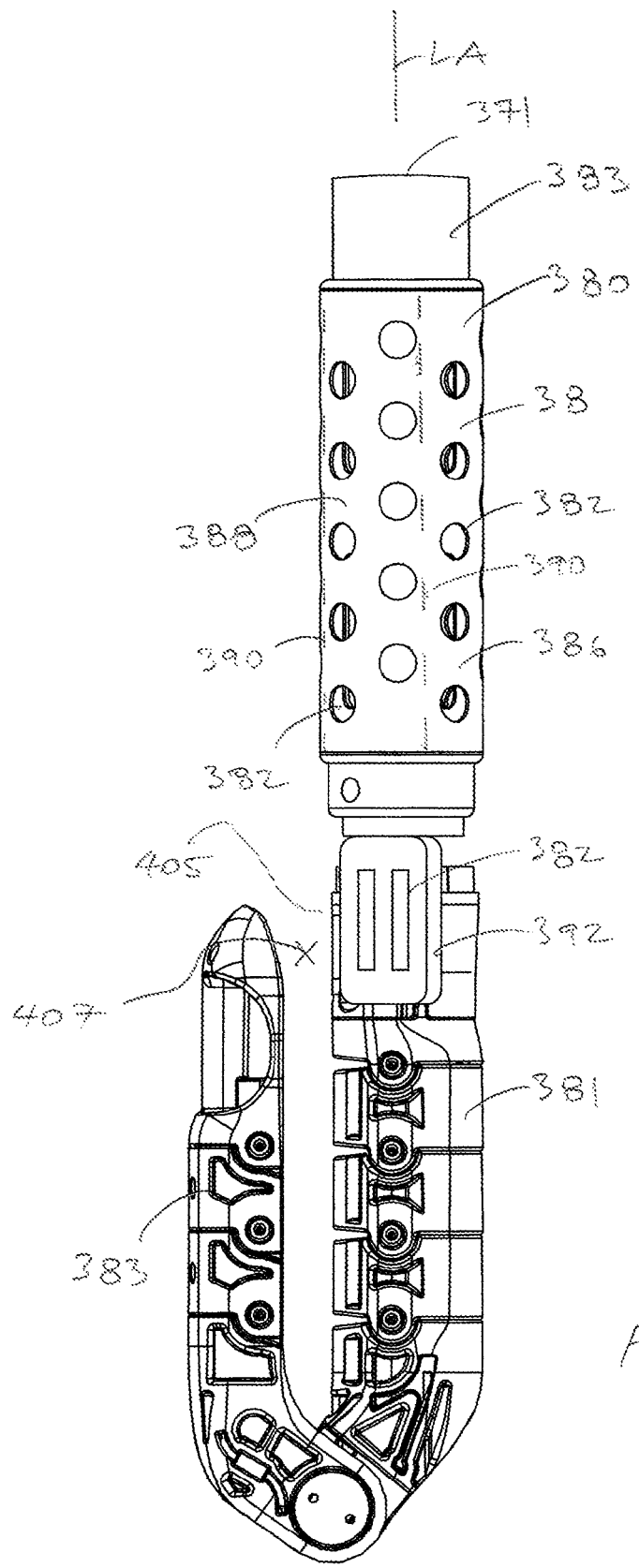
FIG. 48 shows another device for manipulating and fastening tissue.

Referring to FIG. 48, another tissue grasper 380 and tissue shaper 381 are shown. The tissue shaper 381 may be any of the tissue shapers described herein and the tissue shaper 381 has a single pivoting mold 383 for clarity. The tissue grasper 380 has a number of vacuum orifices 382 on the outer surface 381 of an elongate body 383 that defines a longitudinal axis LA. The vacuum orifices 382 adhere the elongate body 383 to the esophagus (or to stomach tissue previously manipulated as described herein). The tissue shaper 381 extends through a lumen 371 in the tissue grasper 380 so that the tissue shaper 381 is rotatable about the longitudinal axis LA and longitudinally translatable relative to the tissue grasper 380 for use as described below.

The tissue grasper 380 is divided into a number of sections. The tissue grasper 380 has a first section 386 and a second section 388 which may be independently activated and are separated at boundary 390. The first section 386 extends 270 degrees around the body 383 while the second section extends 90 degrees when viewed along the longitudinal axis LA. Together, the first and second sections 386, 388 provide a full circumferential sealing surface that adheres and seal with the esophagus for inflating and deflating the stomach as necessary and for manipulating the esophagus.

Figure 49:
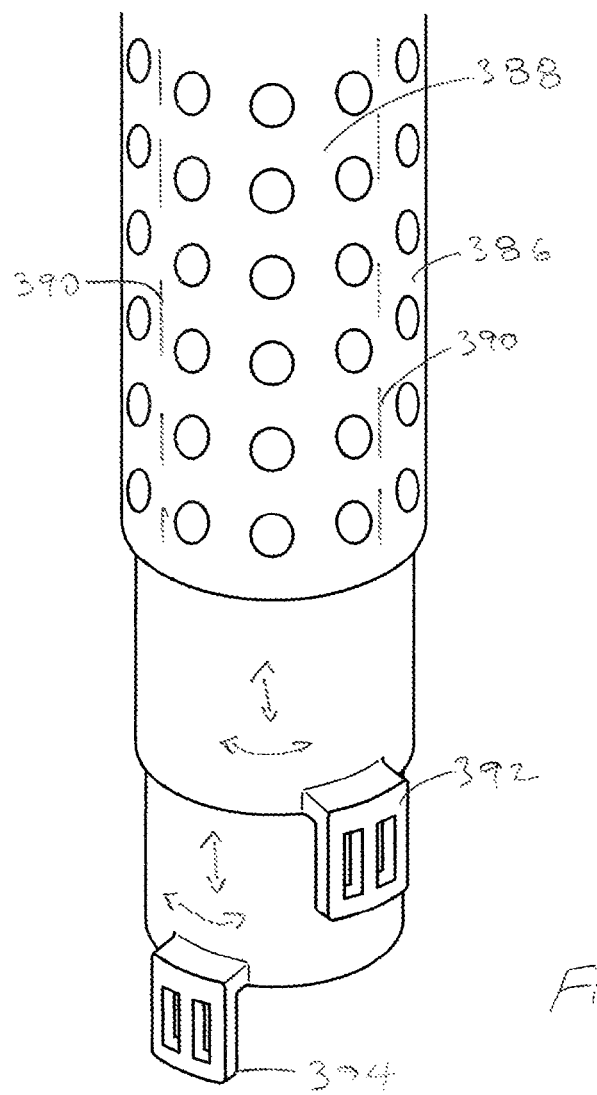
FIG. 49 shows the concentrically mounted sections of the tissue grasper.

The tissue grasper 380 also includes a third section 392 and a fourth section 394 (hidden in FIG. 48) which are independently rotatable about the longitudinal axis and longitudinally translatable relative to one another, to the tissue shaper 384, and to the first and second sections 386, 388 as shown by the diagram of FIG. 49. Referring to the cross-sectional view of FIG. 50, the third section 392, like the fourth section 394, may initially adhere to tissue with suction at the vacuum orifice 382 which leads to a recess 396. A tissue piercing element 398 having a sharp tip 397 is positioned in the recess 396 at or below the outer surface 381 when in the stored position similar to the tissue grasper of FIGS. 42-44. Furthermore, the recess 396 may be a slot 399 having sidewalls 401 that support movement of the tissue piercing element 398. The tissue piercing element 398 is moved to the working position by an actuator 400 having a pull wire 402 coupled to a wedge 404 that applies a force to move the tissue piercing element to a biased position. The sidewalls 401 of the slot 399 also support movement the wedge 404. The wedge 404 may be advanced for shallow penetration, such extending no more than 4 mm from the outer surface, when adjacent structures are potentially problematic and deeper penetration when no such structures are present and/or when full thickness control of a tissue layer is desired. The tissue piercing element 398 naturally moves back to the stored position and displaces the wedge 404 when tension is released on the pull wire 402.

In one aspect of the invention, the third and fourth sections 392, 394 may be positioned at the same longitudinal position relative to the elongate body 383 for manipulating tissue therebetween. For example, the third and fourth sections 392, 394 may be used to hold the site of a prior applied fastener, the end of the fold, or an intended fastener site among other uses. The third and fourth sections 392, 392 may also be positioned at the same longitudinal position to form a window 405 that may be positioned at a fastener application site 407 with the window 405 forming a gap between the third and fourth sections 392, 394. The third and fourth sections 392, 394, like the second section 388, may also act on a limited, defined portion of tissue and, as such, may extend less than 100 degrees around the body when viewed along the longitudinal axis.

The sections of the tissue grasper 380 which are not activated shall constitute a free section 399 that is free of attachments to tissue. As such, the tissue adjacent the free section is free to stretch or gather in accordance with methods described below. Thus, when the first section 386 is activated and the second section 388 is not, the second section 388 shall constitute the free section of the tissue grasper so that the free section extends about 90 degrees when viewed along the longitudinal axis. Stated another way, the tissue adjacent non-activated or free sections of the tissue grasper 380 are free of attachment and free to displace relative to the tissue grasper 380 even though another part of the tissue at the same longitudinal position is held by the tissue grasper. In one specific method described below, for example, the free section 399 is positioned between a previously applied fastener and the next intended fastener location. Finally, when the tissue grasper 380, or other tissue graspers described herein, is spread apart from another element or moved relative to another element, only the active parts of the tissue grasper 380 shall be considered. For example, the tissue grasper 380 may have only the third section 392 activated to adhere to tissue so that reference to position or reference to relative motion of the tissue grasper 380 shall be as to the third section 392 only.

The tissue graspers of the present invention are relatively simple structures which can be formed along the outer surface of the elongate bodies shown herein without excessive intrusion as can be encountered when a number of tools are used in the stomach as suggested by some approaches. Some prior art solutions suggest the use of numerous independent grasping jaws each having an independent shaft and pair of jaws operated within the stomach. In an aspect of the present invention, the tissue graspers are positioned on the outer surface of the elongate body which may be generally cylindrical. As such, the tissue graspers of the present invention provide the ability to manipulate tissue without requiring numerous instruments, and in particular numerous grasping jaws having independent shafts, extending into the stomach although aspects of the present invention, such as the following aspects related to reinforcing, may be practiced with any device include those with multiple grasping jaws having independent shafts.

Referring to FIGS. 51, 52, 53A, 53B, 54A and 54B, a reinforcing element 410 is shown to reinforce the stomach and folds formed in the stomach such as at anterior and posterior ends of the fold. The series of folds formed around the devices of the present invention typically do not extend fully around the esophagus and typically extend from 180 degrees to 270 degrees relative to the longitudinal axis of the elongate body (although more or less may be encountered, of course). As such, the pattern of fasteners (as discussed further below) created at an upper end of the series of folds may be characterized as C-shaped, U-shaped or horseshoe shaped at times.

The reinforcing element 410 is positioned to couple the posterior and anterior ends of the fold together. The reinforcing element 410 has a first side 413 and a second side 419 with each side being positioned adjacent an end of the fold. The reinforcing element 410 may include a first eyelet 412 sized and configured to receive a first fastener 315 and a second eyelet 414 sized and configured to receive a second fastener 315. In one aspect, the first and second sides 413, 419 are positioned on opposite sides of a boundary between the anterior and posterior sides. In this manner, the ends of the fold are anchored to each other thereby reducing slipping and distension. The reinforcing element 410 also may help to reduce the overall load on fasteners at the ends of the fold by absorbing some of the load that would otherwise be applied to the fasteners. Furthermore, the reinforcing element 410 may help create a more "rounded" shape that may distribute loads more evenly than C, U or horseshoe shaped patterns.

The reinforcing element 410 may include a polymer sheet 416 and a woven element 418 that reinforces the polymer 416. A raised lip 420 extends around the periphery of the reinforcing element 410 to help the reinforcing element 410 maintain shape although the reinforcing element 410 is preferably relatively flexible to conform to the stomach as necessary. The reinforcing element 410 may also simply include the woven element 418 with the fastener being driven through interstitial spaces 422 of the woven element 418. The reinforcing element 410 may also omit the eyelets 412, 414 with the fastener being driven directly through and penetrating the polymer sheet 416 during fastening. Fasteners may also be driven through the reinforcing element 410 between the eyelets 412, 414 to pierce the polymer sheet 416 and drive the fastener through the interstitial space 422 of the woven element 418.

Figure 38:
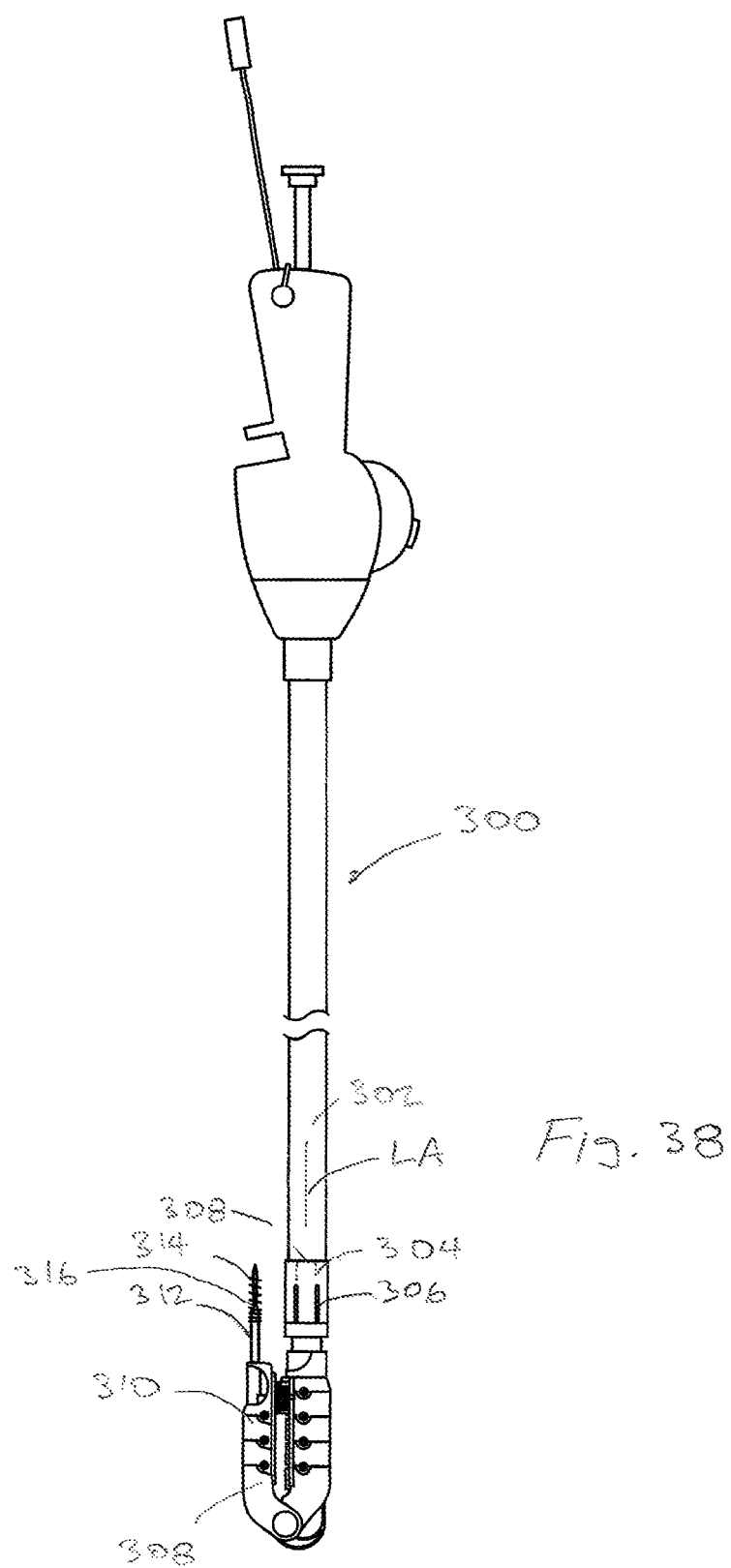
FIG. 38 shows another device for manipulating and fastening tissue.

Referring to FIGS. 53A and 53B, the reinforcing element 410 may be mounted to a tissue grasper 424 which may be any of the other tissue graspers described herein and all such combinations are expressly incorporated. A tissue shaper 425, which also may be any of the tissue shapers described herein, has a pivoting mold 427 coupled to a shaft 429. The shaft 429 extends through the tissue grasper 424 so that the tissue shaper 425 may be rotated and translated relative to the tissue grasper 424. The tissue shaper 425 also includes the tissue displacing element (as shown in FIG. 38) which is retracted and not visible in FIG. 53. The reinforcing element 410 may also be delivered on a separate delivery element from the tissue grasper 424 or may be mounted to the tissue shaper 425 without departing from numerous aspects of the invention.

A support collar 426 extends distally from the tissue grasper 424 and the reinforcing element 410 is positioned in a complementary shaped cavity 428 in the collar 426. The collar 426 also has openings 428 that align with the eyelets 412, 414 to guide the fastener through the eyelets 412, 414. The tissue grasper 424 and tissue shaper 425 are positioned in a fixed radial orientation to align the eyelets 412 with a fastener delivery guide 415. The collar 42 supports the reinforcing element 410 to expose the first and second sides 413, 419 (and specifically the first and second eyelets 412, 414) for application of a fastener. Since the tissue grasper 424 is used for delivering the reinforcing element 410, the tissue grasper 424 at times may constitute a delivery device 421 for the reinforcing element 410 but may include all features of the tissue grasper 424.

The tissue grasper 424 includes a first section 430, a second section 432 and a third section 434 similar to the tissue grasper of FIGS. 48 and 49. The first section extends 270 degrees while the second section extends 90 degrees relative to longitudinal axis LA. The support collar 426 may be centered on the second section 423 or the third section 434. The collar 426 supports the reinforcing element 410 while exposing the first and second sides 413, 419 for application of a fastener through the eyelets 412, 414.

The third section 434 is substantially the same as the tissue grasper of FIGS. 42-44 described above but extends only 90 degrees relative to the longitudinal axis LA. Referring to the cross-sectional views of FIGS. 54A and 54B, the third section 434 includes vacuum orifices 436 and a recess 438, such as an elongate slot 440 having sidewalls 442, and may include a tissue piercing element 444 positioned in each recess 438. An actuator 446 is used to move the tissue piercing element 444 in the same manner as the tissue grasper of FIGS. 42 and 43 described above and all aspects are incorporated here. The actuator 446 may also be used to release the reinforcing element 410 with further advancement of the actuator 446. The reinforcing element 410 is anchored to the support collar 426 with a suture 448 extending through the eyelets 412, 414 (or any other suitable part of the reinforcing element 410 such as through the woven material 418). The suture 448 extends through the collar 426 and is exposed in a trough 450. The actuator 444 has a tip 452 which extends into the trough 450 to sever the suture 448 thereby releasing the reinforcing element 410 as shown in FIG. 54B. A lock (not shown) may be provided to prevent inadvertent advancement of the actuator 446 and accidental release of the reinforcing element 410.

The ends of the fold may be anchored by positioning the second section 432 and/or the third section 434 adjacent one or both ends of the fold. In one method of deploying the reinforcing element 410, one side (or both sides) of the reinforcing element 410 is fastened to tissue simultaneous with formation of a fold. After fastening the reinforcing element 410 to stomach tissue, the reinforcing element 410 continues to be held by the tissue grasper 424 with the suture 448 and, as such, forms part of the tissue grasper 424 for rotating, stabilizing and/or otherwise manipulating tissue as desired. The reinforcing element 410 may also be fastened to tissue independent of forming a fold as discussed further below.

As mentioned above, the reinforcing element 410 may be used to secure the anterior and posterior ends of the fold together. Stated another way, the reinforcing element reinforces an area between adjacent folds and, specifically, may extend across the boundary between the anterior and posterior sides of the stomach along the lesser curvature side of the stomach and may be fastened on both the anterior and posterior sides.

In another aspect of using the reinforcing element 410, the final step in securing the reinforcing element 410 may be performed after forming all of the folds or concurrently with formation of the final fold. In this manner, the reinforcing element 410 may be positioned and tensioned as desired to relieve loads on previously placed fasteners. Stated another way, folds may be formed to create a partial circumferential pattern with the reinforcing element 410 bridging the gap in the partial circumferential pattern to form a complete circumferential pattern. The gap may be bridged with the reinforcing element 410 secured across the boundary between the anterior and posterior sides. Alternatively, the reinforcing element 410 may also be applied at areas other than the ends of the fold where high forces and/or stomach expansion is expected as described below.

The term pattern of fasteners as used herein shall be defined as the pattern created by those fasteners that communicate with adjacent fasteners to resist local deformation of the pattern. The posterior and anterior ends of the C, U or horseshoe shaped fastener pattern described herein are partial, rather than fully circumferential, since the anterior and posterior ends of the fold do not together resist local deformation of the pattern. Loads on the fastener at one end are not shared by the fastener at the other end due to physical constraints of the stomach in this region. The physical constraints in this region also limit the ability to form a fold that prevents creating a full circumferential pattern.

Referring now to FIGS. 46, 47 and 53, the tissue grasper 424 of FIG. 53 (together with the reinforcing element 410) may be substitute for the tissue grasper 357 for use with the first and second tissue shapers 352, 354 of FIGS. 47 and 48 for use as now described. The second tissue shaper 354 is aligned with one of the two eyelets 412, 414 and positioned at an end of the fold (anterior or posterior). The second tissue shaper 354 then applies a fastener through one of the eyelets 412. The first tissue shaper 352 is then positioned near the next intended fastener site. Stomach tissue is then drawn into the first tissue shaper 352 using the first tissue displacing element 362. The first tissue shaper 352 and the reinforcing element 410 are then spread apart prior to fastening with the end of the fold held by the reinforcing element 410 and the tissue grasper. Alternatively, the first tissue shaper 352 and the reinforcing element 410 may also be moved together (rather than spread apart) depending on the particular anatomy and desired direction of wrap. The other end of the reinforcing element 410 may also be attached in a similar manner to complete the circumferential pattern across the anterior/posterior boundary as described above with or without formation of a fold.

Figure 55:
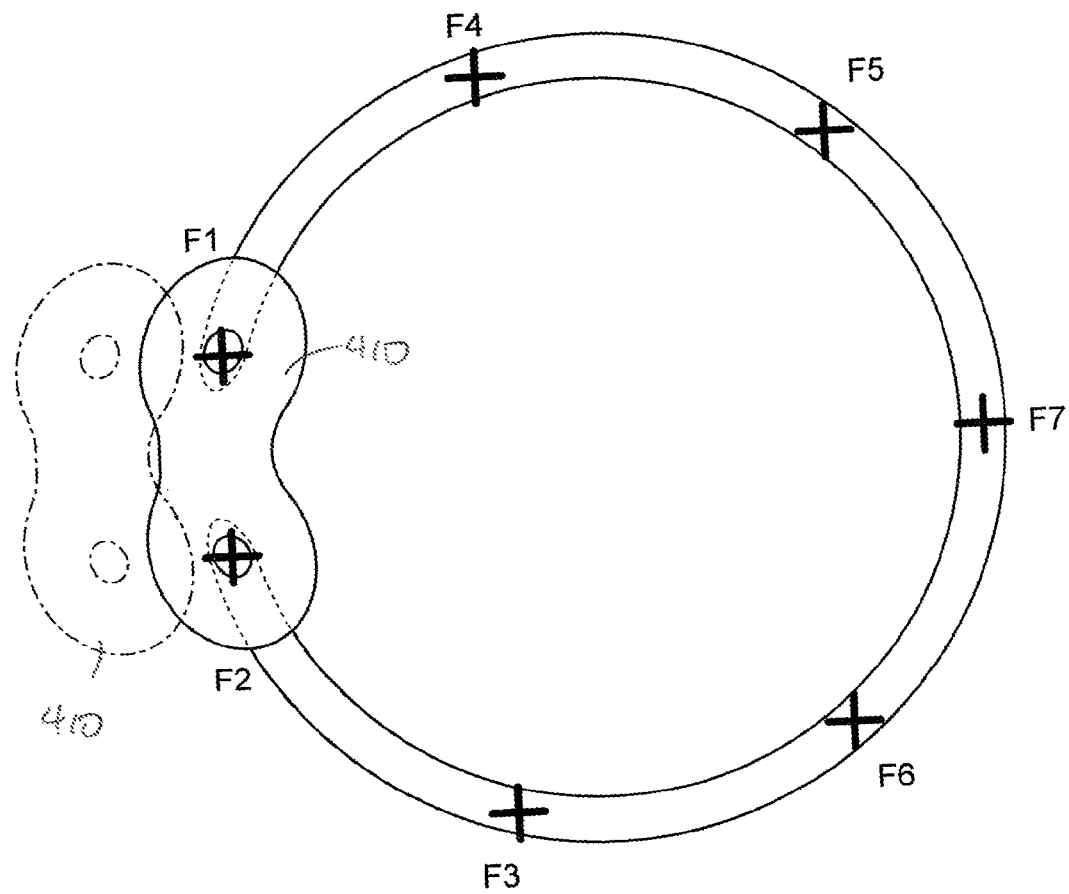
FIG. 55 is a diagram of a fold with the reinforcing element extending from the anterior side to the posterior side at the ends of the fold.

Use of the devices described above and further methods of the present invention are now described. For the purpose of illustrating the present invention, FIG. 55 is a simplified diagram of one application of the present invention, namely, forming a series of folds to create the junction between the esophageal tract and the stomach using stomach tissue. Various related methods and devices are described in U.S. Pat. No. 7,942,887 that is hereby incorporated by reference. Each fastener F1-F7 is applied to create a fold with the folds being formed continuously with one another. Each fold is created by using one of the tissue displacing elements disclosed herein to draw tissue toward and into one of the tissue shapers described herein followed by application of a fastener to hold the fold. The reinforcing element 410 is depicted between fasteners F1 and F2 for use as described above and incorporated here for all methods. Although fasteners F2 and F1 are shown deployed, they may be deployed later (such as last in the fastener pattern) or in any other suitable manner. The reinforcing element 410 is also shown in dotted line separated from the fasteners that form the folds to represent attachment of the reinforcing element 410 independent of creating a fold.

The folds may be formed continuously with previously formed folds so that a combined fold progress around the device. Fasteners F1-F7 may be placed in any order and the particular order described is only for the purpose of illustration. Furthermore, more (or fewer) fasteners may be used in varying patterns also without departing from the present invention.

Figure 56:
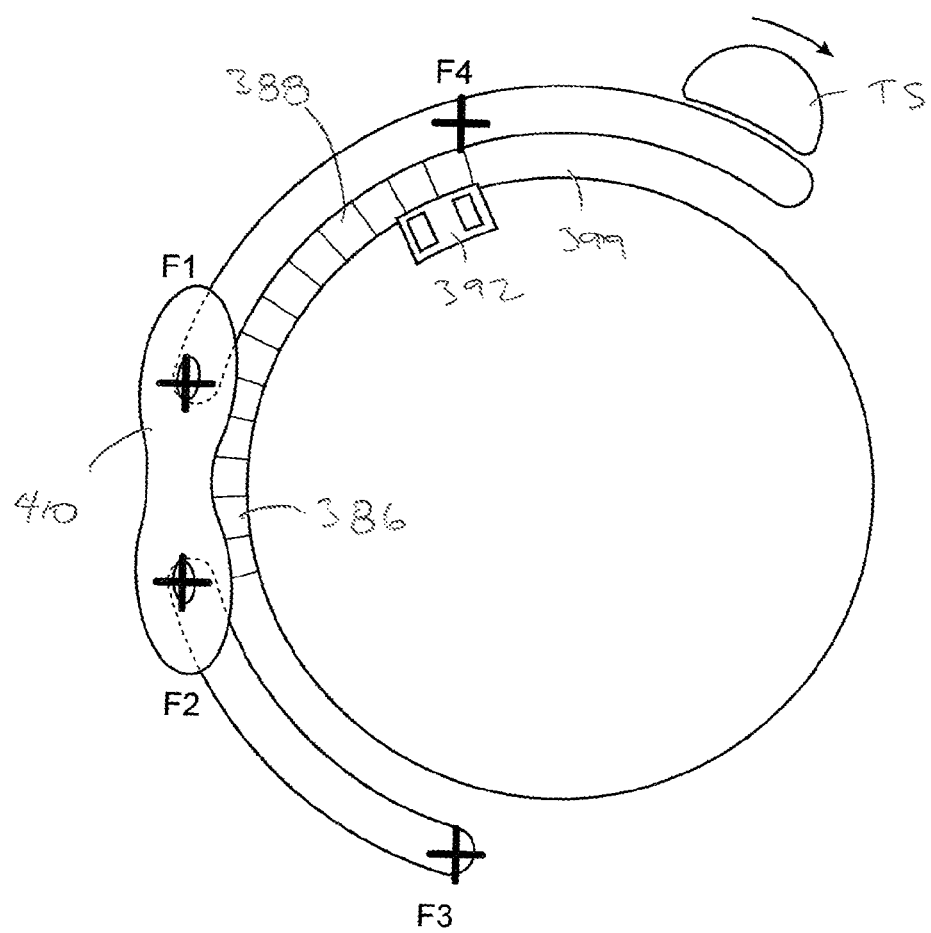
FIG. 56 is a diagram illustrating methods of the present invention.

Referring to FIG. 56, a graphical depiction of the combined fold progressing with fasteners F1-F4 previously applied to form two separate folds progressing from the anterior and posterior ends. Methods in accordance with the present invention are now described with reference to application of fastener F5 and formation of the fold at F5. Use of a tissue shaper TS, which may be any of the tissue shapers described herein, and a tissue grasper TG, which also may also be any of the tissue graspers described herein, is described. The orientation of various devices, elements and aspects of the present invention are typically described with reference to viewing along the longitudinal axis and, as such, refer to angular orientations relative to the longitudinal axis. Thus, when it is stated that a prior placed fastener (such as F4) is positioned between the tissue shaper TS and the tissue grasper TG the position refers to the angular orientation when viewed along the longitudinal axis. As such, the tissue shaper TS and tissue grasper TG may be spread apart (or moved together) in accordance with the present invention by rotating one or both even though the tissue shaper TS and tissue grasper TG act at different longitudinal positions so long as the intended relative motion is imparted and results in the tissue being spread apart (or moved together). Finally, when describing motion of the tissue shaper TS, the tissue shaper TS may hold tissue with the tissue engaging element, the mold, or both.

In one aspect of the present invention, the tissue grasper TG and tissue shaper TS may be spread apart to tighten the fold and wrap the fold around the body of the tissue grasper TG and the shaft of the tissue shaper TS to create a desirable shape. The tissue shaper TS and tissue grasper TG may be spread apart in any manner by rotating one or both (independently, in either order, or simultaneously). When the tissue grasper 380 of FIG. 48 is used, one section, such as the second section 388, may be activated while the other side (such as the first section 386) is not so that the non-activated section constitutes the free section 399. The second section 388 may be positioned relative to the tissue shaper TS to preferentially tighten a specific location or region. For example, the second section 388 may be placed so that the free section 399 of the tissue grasper 380 is positioned between the prior placed fastener F4 and the tissue shaper TS so that this tissue is free to displace and stretch (or be gathered) as desired in this region. The second section 388 may, of course, be placed closer to other prior placed fasteners, such as near F2, to tighten and stretch a larger region. In this manner, the tissue shaper TS is spread apart from the prior placed fastener F4 on one side while the tissue grasper TG is spread apart from the prior placed fastener on the other side (when viewed along the longitudinal axis). In this manner, the tissue is wrapped, tightened and/or shaped as desired. If the tissue grasper 380 is used, the third section 392 (or the fourth section 394) may also be used to control tissue. For example, the third section 392 may be positioned to hold the prior placed fastener F4 to spread apart the tissue shaper TS from the prior placed fastener F4.

As mentioned above, the tissue grasper TG and tissue shaper TS may also be moved toward one another longitudinally to move tissue into the tissue shaper TS before fastening. Moving the tissue grasper TG and tissue shaper TS toward one another may be performed before applying the fastener in all methods of the present invention whether or not expressly described. Furthermore, the tissue shifting element of FIGS. 39-41 may also be incorporated into any of tissue shapers TS, and in particular any pivoting mold described herein to further shift tissue into the tissue shaper TS also in connection with all methods described herein prior to fastening.

Figure 57:
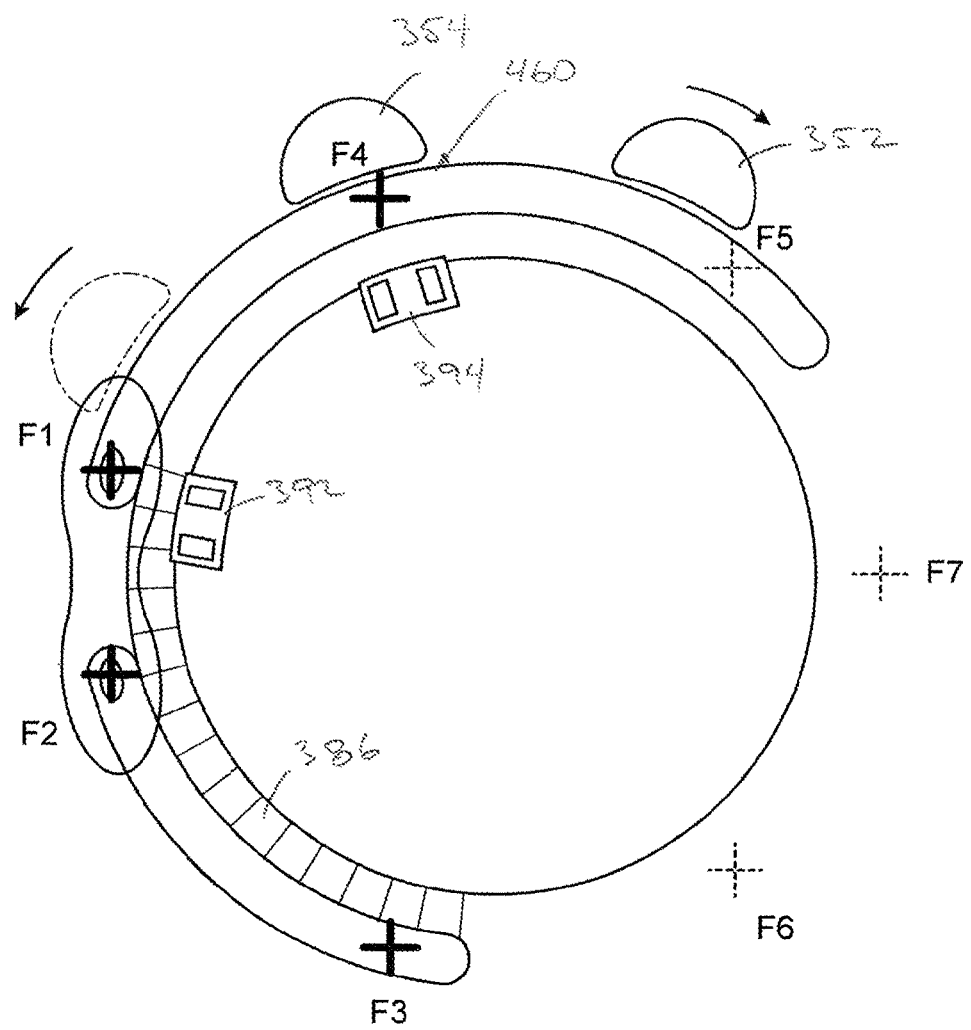
FIG. 57 is another diagram depicting methods of the present invention.

Referring to FIG. 57, another method is depicted in connection with the device having the first and second tissue shapers 352, 354 of FIGS. 45-47 used with the tissue grasper 380 of FIGS. 48-50. Tissue is drawn into the first tissue shaper 352 using the first tissue displacing element 362. The second tissue shaper 354 holds the previously formed fold at F4 and the first and second tissue shapers 352, 354 are then spread apart. To this end, the second tissue shaper 354 may hold the prior formed fold at a control location 460, such as near F4, to locally tighten the fold between F4 and F5 or nearer to F1 to tighten the entire prior formed fold. The control location 460 is positioned between the first tissue shaper 352 and the end of the fold (at F1). The first tissue shaper 352 is preferably rotated away from the second tissue shaper 354 to tighten and wrap the fold and to create the desired geometry. Any one of the first, second, third or fourth sections of the tissue grasper 350 may also be positioned to be spread apart from the second tissue shaper thereby wrapping and tightening the fold on both sides of the second tissue shaper 354. For example, the third section 392 is shown at the end of the fold, the fourth section 394 grasping tissue at the prior fastener F4 and the second section 386 positioned across the anterior/posterior boundary and grasping both the anterior and posterior ends of the fold.

Still referring to FIG. 57, another method is now described. The tissue shaper 352 is used to displace tissue and form the fold in anticipation of fastening at F5. The control location 460 lies between the tissue shaper TS and the end of the fold and may be positioned at the prior fastener F4. The control location 460 may also be controlled by the third section 392 of the tissue grasper 380 (rather than the second tissue shaper 354 as described above). The reinforcing element 410 and/or the fourth section 394 of the tissue grasper 380 may be placed near the end of the fold to spread apart more of the previously formed fold. In this manner, the fold is controlled at numerous locations; the leading edge of the fold, the end of the fold and a control location intermediate of the leading edge and end. An advantage of this method is that the tissue can be controlled with the first, second, third and fourth sections which may provide advantages over more complex systems having multiple jaws.

Figure 58:
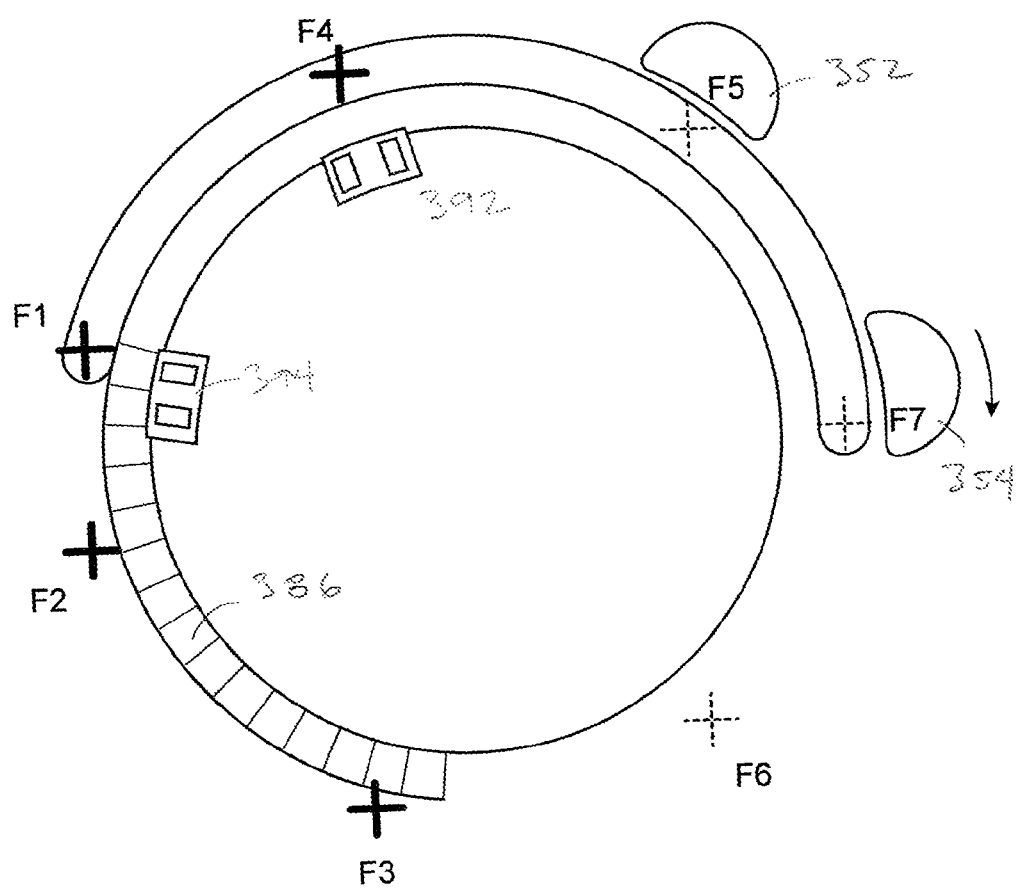
FIG. 58 is still another diagram of methods of the present invention.

In still another method of using the first and second tissue shapers 352, 354 with the tissue grasper 380 of FIGS. 48-50, the second tissue shaper 354 may be used to form a fold ahead of the anticipated fastening site for the first tissue shaper 352 at F5 or, stated another way, the fold is fastened at an intermediate position of fold progression as shown in FIG. 58 rather than at the leading edge. The first tissue shaper 352 may initially form a fold in preparation for application of fastener F5. The second tissue shaper 354 is then used to continue formation of the fold prior to application of fastener F5. By displacing tissue with the second tissue displacing element 364 ahead of the first tissue shaper 352, the load on fastener F5 may be reduced somewhat before fastening. This procedure may be preferable when high forces are encountered and/or expected due to likely stomach expansion.

The first and second tissue shapers 352, 354 may also be spread apart to further tighten the tissue around the intended fastener site F5 before applying fastener F5. At this time, the first mold 358 may be open or partially open to permit the tissue to slip somewhat within the first mold 358 while the first tissue displacing element 362 continues to securely hold the tissue in the first tissue shaper 352. The second tissue shaper 354 may continue to hold the tissue after application of fastener F5 and may apply fastener F7 without releasing the tissue so that relief of loads at F5 is maintained. Fastener F7 is applied by moving the first tissue shaper 352 to align the second fastener guide 368 with the second tissue shaper 354 and fastener F7 may be applied with the second tissue shaper 354. Alternatively, the first tissue shaper 352 may simply be moved adjacent the second tissue shaper 352 to apply fastener F7 without releasing the tissue held by the second tissue shaper 354. Any one of the first, second, third and fourth sections 386, 388, 392, 394 of the tissue grasper 380 may also be used to tighten and wrap tissue. For example, the third section 392 is positioned may be spread apart from the first tissue shaper 352 on one side while the second tissue shaper 354 is spread apart from the first tissue shaper 352 on the other side. The above described method may then be repeated by rotating the first tissue shaper 352 past the second tissue shaper 354 and repeating.

Still another method of the present invention is now described. Upon completion of all folds, the stomach may tend to apply forces on the fold that spread the fasteners apart undesirably. In one aspect of the present method, tissue is moved from the radially inner layer or side to the radially outer layer or side of the fold. In this manner, forces imparted by the fold may be resisted by the radially inner layer. Stated another way, tissue is moved from the inner layer to the outer layer so that excess tissue is provided in the radially outer layer relative to the radially inner layer.

The following method is described in connection with the tissue grasper 380 and any of the tissue shapers described herein such as the tissue shaper 308. Upon application of the prior placed fastener F4, control of the fold at F4 is maintained with the third section 392 at a controlled position relative to the prior placed fastener F4 such as directly above fastener F4. Application of the tissue grasper 380 at the prior fastener F4 also holds the fold in position for further manipulation.

Figure 59:
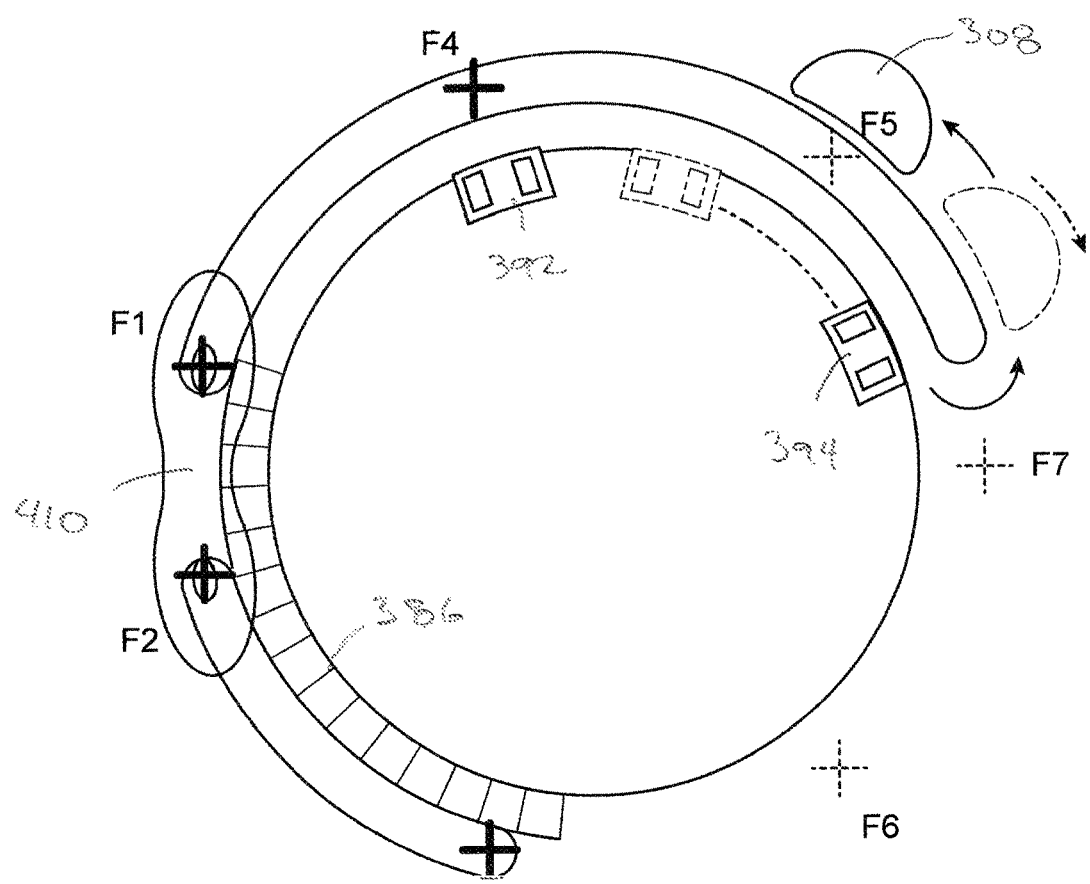
FIG. 59 illustrates shifting tissue from the radially inner side to the radially outer side.

The tissue shaper 308 (and in particular the tissue displacing element 312) is then used to start another fold in anticipation of placing fastener F5 in the direction of fold progression as shown in dotted-line position of FIG. 59. The tissue shaper 308 may be rotated beyond the intended fastener site at F5 without fully retracting the tissue displacing element 312 so that the stomach tissue begins to wrap around device near the third section 392 of the tissue grasper 308. The fourth section 394 of the tissue grasper 380 is then positioned at the dotted-line position between the tissue shaper 308 and the prior placed fastener F4 and activated to grasp the radially inner layer at a positioned spaced apart from the prior fastener F4. The prior fastener F4 and the fourth section 394 are then spread apart to apply tension to the radially inner layer between the fourth section 394 and the prior fastener F4 thereby potentially reducing excess tissue on the radially inner side. Tension is maintained on this portion of tissue until fastener F5 is applied. Manipulating tissue in this manner may also tend to move tissue from the radially inner side to the radially outer side.

The tissue displacing element 312 may then be retracted further and rotated back toward the intended fastener site for F5 (if necessary) while continuing to spread apart tissue on the radially inner side stepwise or simultaneously. Of course, rotation past the intended fastener site and stepwise counter-rotation may not be necessary depending upon the physical characteristics of the stomach tissue and fold shape. The fastener F5 is then applied along the stretched portion of the radially inner layer at a position between the fourth section 394 and the prior placed fastener F4. During this process, the tissue grasper 380 may rotate past one another as shown in FIG. 59.

Figure 60:
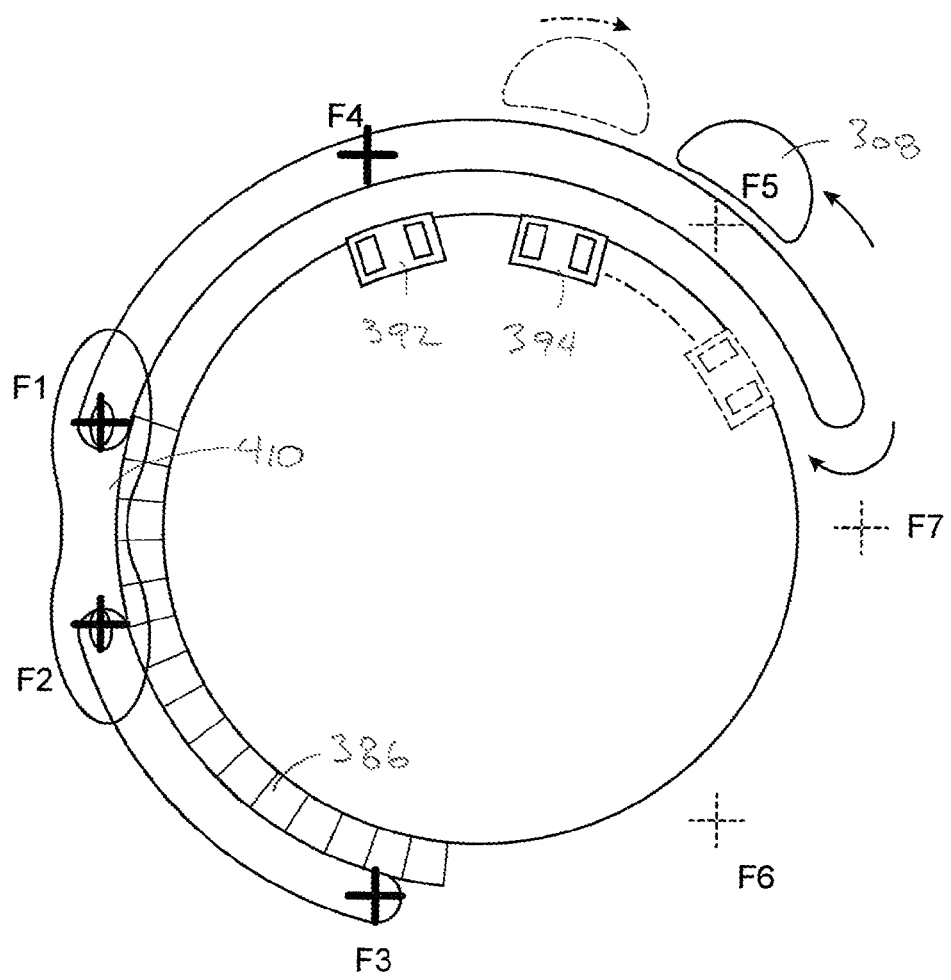
FIG. 60 illustrates shifting tissue from the radially outer side to the radially inner side.

Referring to FIG. 60, another method is depicted which shifts tissue from the radially outer side to the radially inner side. The third section 392 is used to control the tissue adjacent the prior fastener F4 and is positioned just above the fastener F4 before releasing the fold after application of F5. The tissue shaper 308 then displaces tissue into the stomach to begin the next fold. In doing so, the tissue shaper 308 forms the radially inner and outer layers. The fourth section 394 is engaged with the radially inner layer at the dotted-line position of FIG. 60 and is then moved toward the prior fastener F4 to shift tissue from the radially inner layer to the radially outer layer. The tissue shaper 308 may also be moved from the dotted line position toward F7 to further shift tissue from the radially outer layer to the radially inner layer. The tissue shaper 308 is then moved into position to apply fastener F5. The tissue shaper 308 and the fourth section 394 of the tissue grasper 380 may rotate past one another during this process.

In another method in accordance with the present invention, the reinforcing element 410 may be used to reinforce the radially inner side after moving tissue from the radially inner side to the outer side. In this manner, loads on the folds may be directed to the radially inner layer if desirable by shifting tissue to the radially outer side and, further, the radially inner side may be supported by the reinforcing element 410. The reinforcing element 410 is shown extending between F4 and F5 and may be applied simultaneous with one or both of the fasteners F4 and F5 or independently as discussed above and incorporated here. The reinforcing element 410 may also be applied to the radially outer layer using a separate device to reinforce the area where tissue was shifted from the radially outer side to the radially inner side.

The tissue shapers and tissue graspers of the present invention have been described in relation to tissue manipulation aspects of various procedures, however, the tissue shapers and tissue graspers will include other features such as those described in the material incorporated by reference herein. For example, the tissue shapers and/or tissue graspers include an endoscope lumen to receive an endoscope (or may have an integrated visualization device), and one or more lumens for insufflating and desufflating the stomach as is known in the art.

Although the term fold is used herein to describe the two layer structures of the present invention, the fold is substantially formed in accordance with many methods and devices of the present invention by simply displacing the tissue displacing element. Some unsuccessful prior art solutions attempt to fold the esophagus and stomach together which is often not possible when the esophagus has shortened due to disease progression. Displacement of the tissue into the stomach substantially forms the fold in that the two sides are brought into contact with one another typically with only the tissue displacing element even without the tissue shapers of the present invention. The tissue shapers of the present invention primarily form the tissue into a desired shape prior to fastening rather than folding the tissue layers together.

Finally, although the terms first, second, third and fourth have been applied to the various aspects of the devices for clarity, such as the first, second, third and fourth sections of the tissue grasper 380, it is understood, and particularly for the purpose of defining the claims, that any of the enumerated elements may constitute a "first" or "second" section for claim purposes. For example, claims defining the third and fourth sections of tissue grasper 380 may be identified as the "first" and "second" sections in the claims.

The present invention has been described with respect to the preferred embodiment, however, it is understood that numerous modifications could be made without departing from the scope of the present invention. For example, the tissue shaper 4 may be omitted or could be a user actuated structure without departing from the scope of the present invention.

What is claimed is:

1. A method of forming a fold in the stomach continuous with a prior fold formed in the stomach, comprising the steps of:
providing a device including a tissue grasper having an elongate body and a tissue shaper coupled to the elongate body, the elongate body defining a longitudinal axis and having an outer surface, the tissue grasper having a plurality of vacuum orifices positioned on the outer surface, the plurality of vacuum orifices configured to form a sealing surface to adhere tissue to the elongate body using suction;
engaging a first portion of stomach tissue with a tissue engaging element;
drawing the tissue toward the tissue shaper;
applying a first fastener through the tissue drawn to the tissue shaper to form a first fold;
engaging a second portion of stomach tissue with the tissue engaging element;
displacing the second portion of stomach adjacent to and continuous with the first fold, the second portion of stomach tissue forming a radially inner layer and a radially outer layer;
applying the tissue grasper at a location between the first fastener and the tissue shaper when viewed along the longitudinal axis, the tissue grasper grasping the radially inner layer of the second portion of stomach tissue;
spreading the tissue grasper apart from the first fastener while the tissue grasper grasps the radially inner layer thereby applying tension to tissue between the first fastener and the tissue grasper;
positioning the tissue shaper between the first fastener and the tissue grasper when viewed along the longitudinal axis;
fastening the second portion of stomach tissue together with a second fastener to form a second fold;
securing a reinforcing element to the first fold and the second fold to thereby bridge a gap between the first fold and the second fold; and
wherein the positioning step and the spreading step are carried out so that the tissue grasper moves past the tissue shaper when viewed along the longitudinal axis.

2. The method of claim 1, wherein:
the spreading step is carried out to apply tension to tissue between the first fastener and the tissue grasper; and
the fastening step is carried out while tension on the tissue is maintained by the tissue grasper.

3. The method of claim 1, wherein:
the providing step is carried out with the plurality of vacuum orifices forming a circumferential sealing surface.

4. The method of claim 1, wherein:
the tissue grasper having a free section positioned between the tissue grasper and the first fastener when viewed along the longitudinal axis, the free section being free of attachment to the second portion of stomach tissue.

5. The method of claim 1, wherein:
the fastening step is carried out by positioning the second fastener between the tissue grasper and the first fastener when viewed along the longitudinal axis.

6. The method of claim 1, wherein;
the forming the second fold and displacing steps are carried out at least in part simultaneously.

7. The method of claim 1, wherein:
the fastening step is carried out with the second portion of stomach tissue being held by the tissue shaper and the tissue grasper, the tissue grasper holding the radially inner layer and applying tension to tissue between the tissue grasper and the first fastener.

8. The method of claim 1, further comprising the step of:
securing the reinforcing element to the radially inner layer at a position to reinforce the radially inner layer between the first and second fasteners.

9. The method of claim 8, wherein:
the securing step for securing the reinforcing element is carried out simultaneously with the applying the tissue grasper step so that the second fastener secures the reinforcing element to tissue.

10. The method of claim 8, wherein:
the securing step is carried out simultaneously with the fastening step, the reinforcing element having a second side attached to stomach tissue with the second fastener.

11. The method of claim 8, wherein:
the securing step is carried out after the applying the tissue grasper step and after the fastening step, the securing step being carried out by attaching a first side of the reinforcing element adjacent the first fastener and a second side of the reinforcing element adjacent the second fastener.

12. The method of claim 8, wherein:

the securing step is completed while tension is applied to the reinforcing element from the spreading step.

* * * * *